US006833366B1

(12) United States Patent
Rogers et al.

(10) Patent No.: US 6,833,366 B1
(45) Date of Patent: Dec. 21, 2004

(54) DIHYDROSTILBENE ALKANOIC ACID DERIVATIVES

(75) Inventors: Thomas Rogers, Ballwin, MO (US); Michael Clare, Skokie, IL (US); Hwang-Fun Lu, Manchester, MO (US); Mark Russell, Grunee, IL (US); James W. Malecha, Libertyville, IL (US); Ish Kumar Khanna, Libertyville, IL (US); Thomas Penning, Elmhurst, IL (US); Srinivasan Raj Nagarajan, Chesterfield, MO (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 10/657,932

(22) Filed: Sep. 9, 2003

Related U.S. Application Data

(62) Division of application No. 09/882,137, filed on Jun. 15, 2001, now Pat. No. 6,720,315.
(60) Provisional application No. 60/211,780, filed on Jun. 15, 2000.

(51) Int. Cl.$^7$ ...................... A61K 31/33; A61K 31/435; A61K 31/44; C07D 213/50
(52) U.S. Cl. ...................... 514/183; 514/253; 514/277; 514/336; 514/349; 514/351; 514/357; 546/1; 546/304; 546/339; 546/329
(58) Field of Search ................................. 514/183, 253, 514/277, 336, 349, 351, 357; 546/1, 304, 339, 329

(56) References Cited

U.S. PATENT DOCUMENTS 5,919,792 A * 7/1999 Duggan et al. ............. 514/300

FOREIGN PATENT DOCUMENTS

| EP | 0 694 543 | 1/1996 | ......... C07D/413/04 |
|---|---|---|---|
| WO | WO 93/12796 | 7/1993 | ......... A61K/31/415 |
| WO | WO 98/31359 | 7/1998 | ......... A61K/31/18 |
| WO | WO 99/05107 | 2/1999 | ......... C07D/211/72 |
| WO | WO 99/15508 | 4/1999 | ......... C07D/239/02 |
| WO | 9952896 | * 10/1999 | |
| WO | WO 99/52896 | 10/1999 | ......... C07D/401/12 |

OTHER PUBLICATIONS

Berge et al., Pharmaceutical Salts, *J. Pharm. Sci.*, vol. 66(1), pp. 1–19, Jan. 1977.
Vu et al., Angiogenic Activity in Injured Rat Corneas as Assayed on the Chick Chorioallantoic Membrane, *Lab Invest.*, vol. 53(3), pp. 311–319, 1985.
Robertson et al., A Quantitative in Vivo Mouse Model Used to Assay Inhibitors of Tumor–induced Angiogenesis, *Cancer Res.*, vol. 51, pp. 1339–1344, Feb. 1991.

Ribatti et al., New Model for the Study of Angiogenesis and Antiangiogenesis in the Chick Embryo Chorioallantoic Membrane: The Gelatin Sponge/Chorioallatoic Membrane Assay, *J. Vasc. Res.*, vol. 34, pp. 455–463, Nov–Dec. 1997.
Carcellar et al., Synthesis and Structure–Activity Relationships of 1–Acyl–4–((–2–methyl–3–pyridyl)cyanomethyl)piperazines as PAF Antagonists, *J. Med. Chem.*, vol. 36, pp. 2984–2997, 1993.
Miller, W. H. et al., Discovery of Orally Active Nonpeptide Vitronectin Receptor Antagonists Based on a 2–Benzazepine Gly–Asp Mimetic, *J. Med. Chem.*, vol. 43, pp. 22–26, 2000.
Pytela et al., Arginine–Glycine–Aspartic Acid Adhesion Receptors, *Methods in Enzymology*, vol. 144, pp. 475–489, 1987.
Yatohgo et al., Novel Purification of Vitronectin for Human Plasma by Heparin Affinity Chromatography, *Cell Structure and Function*, vol. 13, pp. 281–292, 1988.
Charo et al., Inhibition of Fibrinogen Binding to GP IIb–IIIa by a GP IIIa Peptide, *J. Biol. Chem.*, vol. 266(3), pp. 1415–1421, Jan. 1991.
Niiya et al., Increased Surface Expression of the Membrane Glycoprotein IIb/IIa Complex Induced by Platelet Activation. Relationship to the Binding of Fibrinogen and Platelet Aggregration, *Blood*, vol. 70(2), pp. 475–483, Aug. 1987.
Zucker, Platelet Aggregation Measured by the Photometric Method, *Methods in Enzymology*, vol. 169, pp. 117–133, 1989.
Carron et al., A peptidomimetic antagonist of the integrin alpha(v)beta3 inhibits Leydig cell tumor growth and the development of hypercalcemia of malignancy, *Cancer Res.*, vol. 58(9), pp. 1930–1935, 1998.
Lark et al., Antagonism of the Osteoclast Vitronectin Receptor with an Orally Active Nonpeptide Inhibitor Prevents Cancellous Bone Loss in the Ovariectomized Rat, *J. Bone Miner. Res.*, vol. 16(2), pp. 319–327, 2001.
Healy et al., Angiogenesis: a new theory for endometriosis, *Hum. Repdoductive Update*, vol. 4(5), pp. 736–740, 1998.
Cheresh., Structure, function and biological properties of integrin $\alpha_v\beta_3$ and $\alpha_v\beta_5$ in ocular neovascular diseases, *Proc. Natl. Acad. Sci.*, vol. 93, pp. 9764–9769, Sep. 1996.
Badger et al., Disease–Modifying Activity of SB 273005, an Orally Active, Nonpeptide $\alpha_v\beta_3$ (Vitronectin Receptor) Antagonist, in Rat Adjuvant–Induced Arthritis, *Arthritis & Rheum.*, vol. 44(1), pp. 128–137, Jan. 2001.
Brown et al., Stimulation of migration of human aortic smooth muscle cells by vitronection: implications for atherosclerosis, *Cardiovascular Res.*, vol. 28, pp. 1815–1820, 1994.
Seftor et al., Role of the $\alpha_v\beta_3$ integrin in human melanoma cell invasion, *Proc. Natl. Acad. Sci. USA*, vol. 89, pp. 1557–1561, Mar. 1992.
Montgomery et al., Integrin $\alpha_v\beta_3$ rescues melanoma cells from apoptosis in three–dimensional dermal collagen, *Proc. Natl. Acad. Sci. USA*, vol. 91, pp. 8856–8860, Sep. 1994.
Brooks et al., Integrin $\alpha_v\beta_3$ Antagonists Promote Tumor Regression by Inducing Apoptosis of Angiogenic Blood Vessels, *Cell*, vol. 79, pp. 1157–1164, Dec. 1994.
Adamis et al., Increased Vascular Endothelial Growth Factor Levels in the Vitreous of Eyes with Proliferative Diabetic Retinopathy, *Amer. J. Opthal.*, vol. 118, pp. 445–450, Oct. 1994.

Peacock et al., Angiogenesis Inhibition Suppresses Collagen Arthritis, *J. Exp. Med.*, vol. 175, pp. 1135–1138, Apr. 1992.

Brooks et al., Requirement of Vascular Integrin $\alpha_v\beta_3$ for Angiogenesis, *Science*, vol. 264, pp. 569–571.

Sato et al., Echistatin Is a Potent Inhibitor of Bone Resorption in Culture, *J. Cell. Biol.*, vol. 111, pp. 1713–1723, Oct. 1990.

Fisher et al., Inhibition of Osteoclastic Bone Resorption in Vivo by Echistatin, an "Arginyl–Glycly–Aspartyl" (RGD)–Containing Protein, *Endocrinology*, vol. 132(3), pp. 1411–1413, 1993.

Choi et al., Inhibition of neointimal hyperplasia by blocking $\alpha_v\beta_3$ integrin with a small peptide antagonist GpenGRGD-SPCA, *J. Vasc. Surg.*, vol. 19(1), pp. 125–134.

White, Integrins as virus receptors, *Current Biology*, vol. 3(9), pp. 596–599, 1993.

Friedlander et al., Definition of Two Angiogenic Pathways by Distinct $\alpha_v$ Integrins, *Science*, vol. 270, pp. 1500–1502, Dec. 1995.

\* cited by examiner

*Primary Examiner*—Richard L. Raymond
*Assistant Examiner*—Sudhaker B. Patel
(74) *Attorney, Agent, or Firm*—Rachel A. Polster; Harness, Dickey & Pierce

(57) ABSTRACT

The present invention relates to a class of compounds represented by the Formula 1.

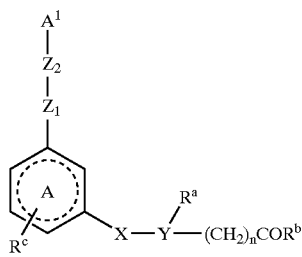

or a pharmaceutically acceptable salt thereof, pharmaceutical compositions comprising compounds of the Formula 1, and methods of selectively inhibiting or antagonizing the $\alpha_v\beta_3$ and/or the $\alpha_v\beta_5$ integrin.

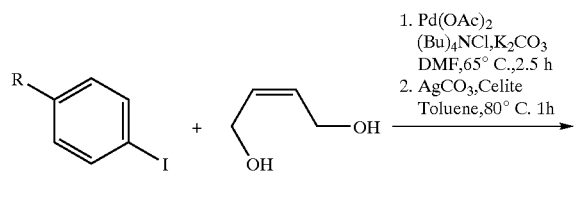

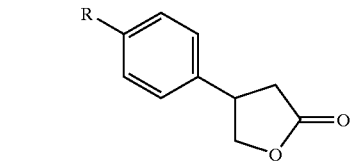

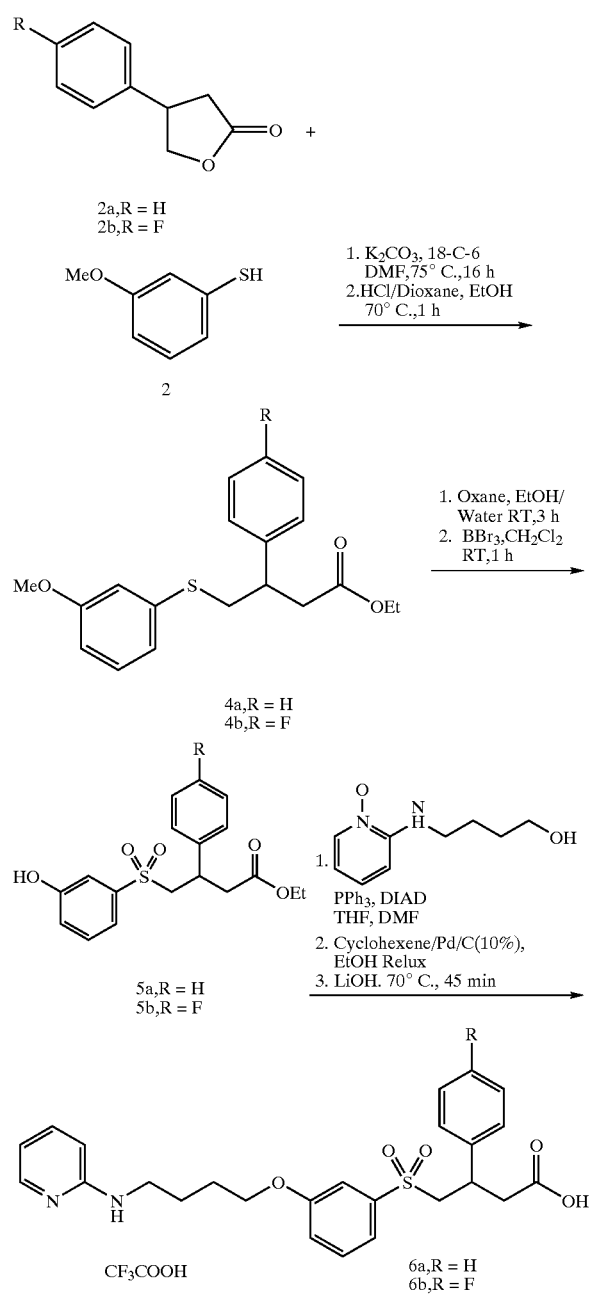

16 Claims, No Drawings

DIHYDROSTILBENE ALKANOIC ACID DERIVATIVES

This application is a divisional application of U.S. application Ser. No. 09/882,137 filed Jun. 15, 2001, now U.S. Pat. No. 6,720,315 allowed, which claims priority from U.S. Provisional Application Ser. No. 60/211,780, filed Jun. 15, 2000, now abandoned.

FIELD OF THE INVENTION

The present invention relates to pharmaceutical agents (compounds) which are $\alpha_v\beta_3$ and/or $\alpha_v\beta_5$ integrin antagonists and as such are useful in pharmaceutical compositions and in methods for treating conditions mediated by $\alpha_v\beta_3$ and/or $\alpha_v\beta_5$ integrins.

BACKGROUND OF THE INVENTION

The integrin $\alpha_v\beta_3$ (also known as vitronectin receptor), is a member of the integrin family of heterodimeric transmembrane glycoprotein complexes that mediate cellular adhesion events and signal transduction processes. Integrin $\alpha_v\beta_3$ is expressed in number of cell types and has been shown to mediate several biologically relevant processes, including adhesion of osteoclasts to the bone matrix, vascular smooth muscle cell migration and angiogenesis.

The integrin avb3 has been shown to play a role in various conditions or disease states including tumor metastasis, solid tumor growth (neoplasia), osteoporosis (Ross, et al., *J. Biol, Chem.,* 1987, 262, 7703), Paget's disease, humoral hypercalcemia of malignancy (Carron et al., *Cancer Res.* 1998, 58, 1930), osteopenia (Lark et al., *J Bone Miner Res.* 2001, 16, 319), endometriosis (Healy et al., *Hum. Reproductive Update,* 1998, 4, 736), angiogenesis, including tumor angiogenesis (Cheresh, *Cancer Metastasis Rev.,* 1991, 10, 3–10 and Brooks, et al., *Cell,* 1994, 79, 1157), retinopathy including macular degeneration (Friedlander et al., *Proc. Natl. Acad. Sci USA* 1996, 93, 9764), arthritis, including rheumatoid arthritis (Badger et al., *Arthritis Rheum,* 2001, 44, 128), periodontal disease, psoriasis and smooth muscle cell migration (e.g. restenosis and artherosclerosis, (Brown et al., *Cardiovascular Res.,* 1994, 28, 1815). The compounds of the present invention are $\alpha_v\beta_3$ antagonists and can be used, alone or in combination with other therapeutic agents, in the treatment or modulation of various conditions or disease states described above. Additionally, it has been found that such agents would be useful as antivirals, antifungals and antimicrobials The integrin $\alpha_v\beta_5$ plays a role in neovascularization. Therefore the compounds of this invention which act as antagonists of the $\alpha_v\beta_5$ integrin will inhibit neovascularization and will be useful for treating and preventing angiogenesis metastasis, tumor growth, macular degeneration and diabetic retionopathy.

It has been shown that the $\alpha_v\beta_3$ integrin and other $\alpha_v$ containing integrins bind to a number of Arg-Gly-Asp (RGD) containing matrix macromolecules. Compounds containing the RGD sequence mimic extracellular matrix ligands so as to bind to cell surface receptors. However, it is also known that RGD peptides in general are non-selective for RGD dependent integrins. For example, most RGD peptides which bind to $\alpha_v\beta_3$ also bind to $\alpha_v\beta_5$, $\alpha_v\beta_1$ and $\alpha_{IIb}\beta_3$. Antagonism of platelet $\alpha_{IIb}\beta_3$ (also known as the fibrinogen receptor) is known to block platelet aggregation in humans. In order to avoid bleeding side-effects when treating the conditions or disease states associated with the integrin $\alpha_v\beta_3$, it would be beneficial to develop compounds which are selective antagonists of $\alpha_v\Theta_3$ as opposed to $\alpha_{IIb}\beta_3$.

Certain compounds of this invention antagonize both the $\alpha_v\beta_5$ and the $\alpha_v\beta_3$ receptor and therefore are referred to as "mixed $\alpha_v\beta_5/\alpha_v\beta_3$ antagonists" or "dual $\alpha_v\beta_3/\alpha_v\beta_5$ antagonists". Such dual or mixed antagonists are useful for treating or preventing angiogenesis, tumor metastasis, tumor growth, diabetic retinopathy, macular degeneration, atherosclerosis and osteoporosis. The compounds of the present invention further show greater selectivity for the $\alpha_v\beta_3$ and/or $\alpha_v\beta_5$ integrin than for the $\alpha_v\beta_6$ integrin. It has been found that the selective antagonism of the $\alpha_v\beta_3$ integrin is desirable in that the $\alpha_v\beta_6$ integrin may play a role in normal physiological processes of tissue repair and cellular turnover that routinely occur in the skin and pulmonary tissue. Therefore, compounds of the present invention which selectively inihibit the $\alpha_v\beta_3$ integrin as opposed to the $\alpha_v\beta_6$ integrin have reduced side-effects associated with inhibtion of the $\alpha_v\beta_6$ integrin.

The compounds of this invention are therefore 1) $\alpha_v\beta_3$ integrin antagonists; or 2) $\alpha_v\beta_5$ integrin antagonists; or 3) mixed or dual $\alpha_v\beta_3/\alpha_v\beta_5$ antagonists. The present invention includes compounds which inhibit the respective integrins and also includes pharmaceutical compositions comprising such compounds. The present invention further provides for methods for treating or preventing conditions mediated by the $\alpha_v\beta_3$ and/or $\alpha_v\beta_5$ receptors in a mammal in need of such treatment comprising administering a therapeutically effective amount of the compounds of the present invention and pharmaceutical compositions of the present invention. Administration of such compounds and compositions of the present invention inhibits angiogenesis, tumor metastasis, tumor growth, osteoporosis, Paget's disease, humoral hypercalcemia of malignancy, retinopathy, macular degeneration, arthritis, periodontal disease, smooth muscle cell migration, including restenosis and artherosclerosis, and viral diseases.

Tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor.

Seftor et al. (Proc. Natl. Acad. Sci. USA, Vol. 89 (1992) 1557–1561) have shown that the $\alpha_v\beta_3$ integrin has a biological function in melanoma cell invasion. Montgomery et al., (Proc. Natl. Acad. Sci. USA, Vol. 91 (1994) 8856–60) have demonstrated that the integrin $\alpha_v\beta_3$ expressed on human melanoma cells promotes a survival signal, protecting the cells from apoptosis. Mediation of the tumor cell metastatic pathway by interference with the $\alpha_v\beta_3$ integrin cell adhesion receptor to impede tumor metastasis would be beneficial.

Brooks et al. (Cell, Vol. 79 (1994) 1157–1164) have demonstrated that antagonists of $\alpha_v\beta_3$ provide a therapeutic approach for the treatment of neoplasia (inhibition of solid tumor growth) since systemic administration of $\alpha_v\beta_3$ antagonists causes dramatic regression of various histologically distinct human tumors.

The compounds of the present invention are useful for the treatment, including prevention of angiogenic disorders. The term angiogenic disorders include conditions involving abnormal neovascularization. The growth of new blood vessels, or angiogenesis, also contributes to pathological conditions such as diabetic retinopathy including macular degeneration (Adamis et al., Amer. J. Ophthal., Vol. 118, (1994) 445–450) and rheumatoid arthritis (Peacock et al., J. Exp. Med., Vol. 175, (1992), 1135–1138). Therefore, $\alpha_v\beta_3$ antagonists would be useful therapeutic agents for treating such conditions associated with neovascularization (Brooks et al., Science, Vol. 264, (1994), 569–571).

It has been reported that the cell surface receptor $\alpha_v\beta_3$ is the major integrin on osteoclasts responsible for attachment to bone. Osteoclasts cause bone resorption and when such bone resorbing activity exceeds bone forming activity it leads to an increased number of bone fractures, incapacitation and increased mortality. Antagonists of $\alpha_v\beta_3$ have been shown to be potent inhibitors of osteoclastic activity both in vitro [Sato et al., J. Cell. Biol., Vol. 111 (1990) 1713–1723] and in vivo [Fisher et al., Endocrinology, Vol. 132 (1993) 1411–1413]. Antagonism of $\alpha_v\beta_3$ leads to decreased bone resorption and therefore restores a normal balance of bone forming and resorbing activity. Thus it would be beneficial to provide antagonists of osteoclast $\alpha_v\beta_3$ which are effective inhibitors of bone resorption and therefore are useful in the treatment or prevention of osteoporosis.

The role of the $\alpha_v\beta_3$ integrin in smooth muscle cell migration also makes it a therapeutic target for prevention or inhibition of neointimal hyperplasia which is a leading cause of restenosis after vascular procedures (Choi et al., J. Vasc. Surg. Vol. 19(1) (1994) 125–34). Prevention or inhibition of neointimal hyperplasia by pharmaceutical agents to prevent or inhibit restenosis would be beneficial.

White (Current Biology, Vol. 3(9)(1993) 596–599) has reported that adenovirus uses $\alpha_v\beta_3$ for entering host cells. The integrin appears to be required for endocytosis of the virus particle and may be required for penetration of the viral genome into the host cell cytoplasm. Thus compounds which inhibit $\alpha_v\beta_3$ would find usefulness as antiviral agents.

M. C. Friedlander, et al., Science, 270, 1500–1502 (1995) disclose that a monoclonal antibody for $\alpha_v\beta_5$ inhibits VEFG-induced angiogenesis in the rabbit cornea and the chick chorioallantoic membrane model.

SUMMARY OF THE INVENTION

The present invention relates to a class of compounds represented by the Formula 1.

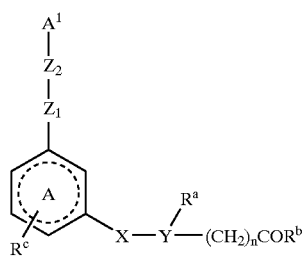

or a pharmaceutically acceptable salt thereof, wherein

is a 4–8 membered monocyclic or a 7–11 membered bicyclic ring, optionally containing 1 to 4 heteroatoms, selected from the group consisting of O, N or S; optionally saturated or unsaturated, optionally substituted with one or more substituent selected from the group consisting of alkyl, haloalkyl, aryl, heteroaryl, halogen, alkoxyalkyl, aminoalkyl, hydroxy, nitro, alkoxy, hydroxyalkyl, thioalkyl, amino, alkylamino, arylamino, alkylsulfonamide, acyl, acylamino, sulfone, sulfonamide, allyl, alkenyl, methylenedioxy, ethylenedioxy, alkynyl, carboxamide, cyano, and —(CH$_2$)$_n$COR wherein n is 0–2 and R is hydroxy, alkoxy, alkyl or amino;

$A^1$ is a 5–9 membered monocyclic or 7–14 membered polycyclic heterocycle of the formula

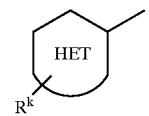

containing at least one nitrogen atom and optionally 1 to 4 heteroatoms or groups selected from O, N, S, SO$_2$ or CO; optionally saturated or unsaturated; optionally substituted by one or more $R^k$ selected from the group consisting of hydroxy, alkyl, alkoxy, alkoxyalkyl, thioalkyl, haloalkyl, cyano, amino, alkylamino, halogen, acylamino, sulfonamide and —COR wherein R is hydroxy, alkoxy, alkyl or amino;

include the following heterocyclic ring systems containing at least one nitrogen atom:

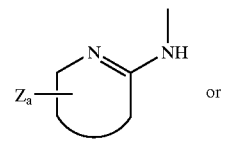

B2

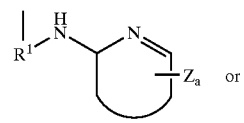

B3

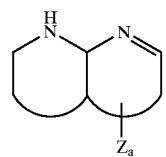

B4 wherein $Z_a$ is H, alkyl, alkoxy, hydroxy, amine, alkylamine, dialkylamine, carboxyl, alkoxycarbonyl, hydroxyalkyl, halogen or haloalkyl and $R^1$ is H, alkyl, alkoxyalkyl, acyl, haloalkyl or alkoxycarbonyl. More specifically some examples of embodiments include pyridylamino, imidazolylamino, morpholinopyridine, tetrahydronaphthyridine, oxazolylamino, thiazolylamino, pyrimidinylamino, quinoline, isoquinoline, tetrahydroquinoline, imidazopyridine, benzimidazole, pyridone or quinolone.

The following heteroaryls include the ring systems described above.

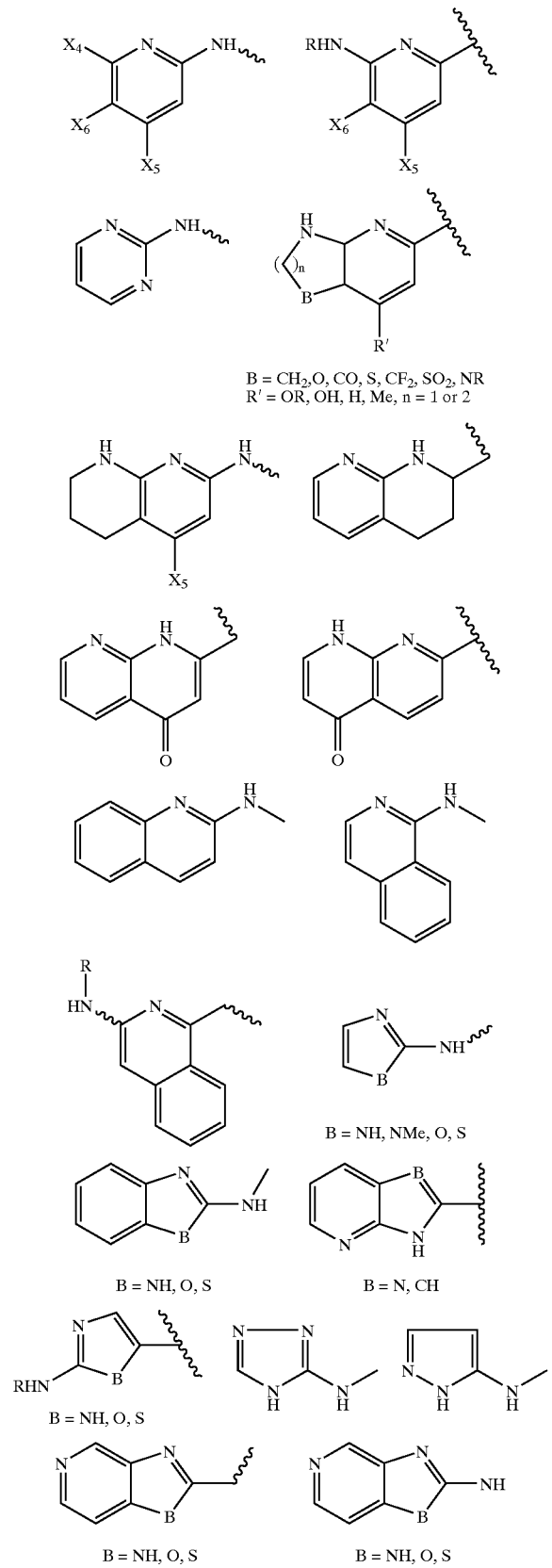
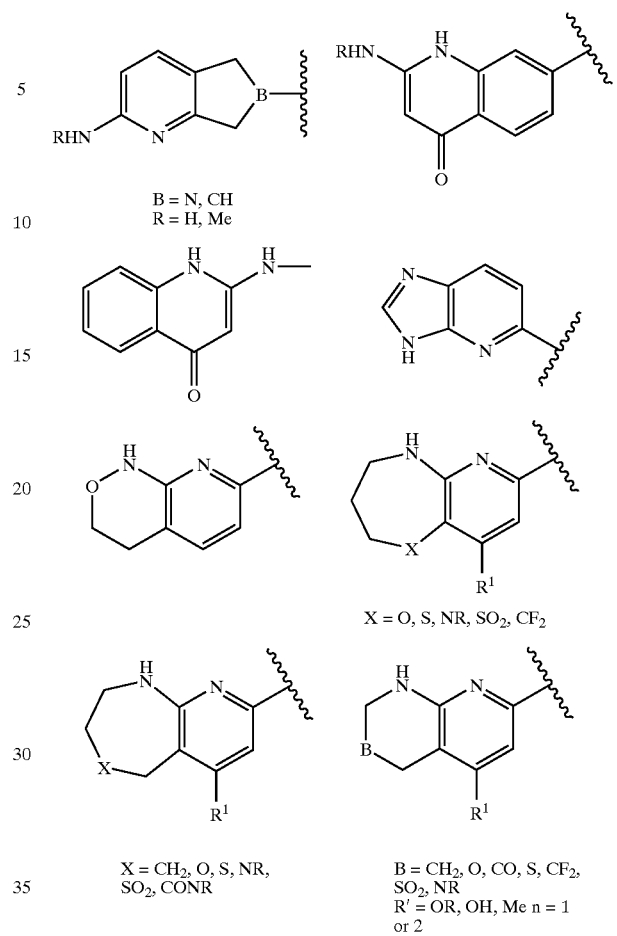

For the pyridyl derived heterocycle, the substituents $X_4$ and $X_5$ are selected from the group consisting of H, alkyl, branched alkyl, alkylamino, alkoxyalkylamino, haloalkyl, thioalkyl, halogen, amino, alkoxy, aryloxy, alkoxyalkyl, hydroxy, cyano or acylamino groups. In another embodiment of the invention, the substituents $X_4$ and $X_5$ can be methyl, methoxy, amine, methylamine, trifluoromethyl, dimethylamine, hydroxy, chloro, bromo, fluoro and cyano. $X_6$ may preferentially be H, alkyl, hydroxy, halogen, alkoxy and haloalkyl. Alternately, the pyridyl ring can be fused with a 4–8 membered ring, optionally saturated or unsaturated. Some examples of these ring systems include tetrahydronaphthyridine, quinoline, tetrahydroquinoline, azaquinoline, morpholinopyridine, imidazopyridine and the like. The monocyclic ring systems such as imidazole, thiazole, oxazole, pyrazole, and the like, may contain an amino or alkylamino substituent at any position within the ring.

In another embodiment of the present invention, when $Z_1$ of Formula I is CO or $SO_2$, the linkage $A^1$—$Z_2$ of Formula I includes the heterocycle derived ring systems such as: pyridine, imidazole, thiazole, oxazole, benzimidazole, imidazopyridine and the like.

Other heterocycles for $A^1$—$Z_2$ of the present invention include

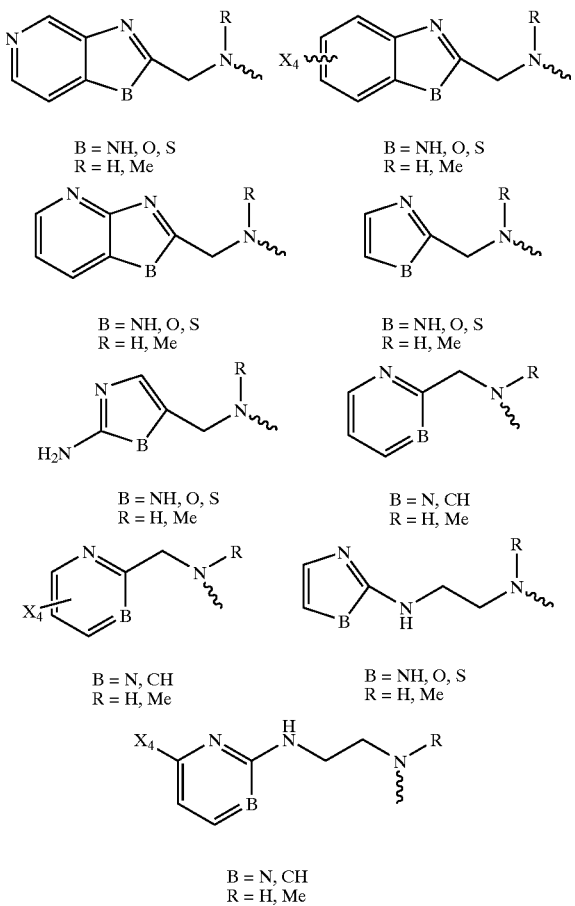

wherein $X_4$ is as defined above.
or $A^1$ is

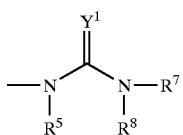

wherein $Y^1$ is selected from the group consisting of N—$R^2$, O and S;

$R^2$ is selected from the group consisting of H; alkyl; aryl; hydroxy; alkoxy; cyano; alkenyl; alkynyl; amido; alkylcarbonyl; arylcarbonyl; alkoxycarbonyl; aryloxycarbonyl; haloalkylcarbonyl; haloalkoxycarbonyl; alkylthiocarbonyl; arylthiocarbonyl; acyloxymethoxycarbonyl;

$R^2$ taken together with $R^7$ forms a 4–12 membered dinitrogen containing heterocycle optionally substituted with one or more substituent selected from the group consisting of lower alkyl, thioalkyl, alkylamino, hydroxy, keto, alkoxy, halo, phenyl, amino, carboxyl or carboxyl ester, and fused phenyl;

or $R^2$ taken together with $R^7$ forms a 4–12 membered heterocycle containing one or more heteroatom selected from O, N and S optionally unsaturated;

or $R^2$ taken together with $R^7$ forms a 5 membered heteroaromatic ring fused with a aryl or heteroaryl ring;

$R^7$ (when not taken together with $R^2$) and $R^8$ are independently selected from the group consisting of H; alkyl; alkenyl; alkynyl; aralkyl; amino; alkylamino; hydroxy; alkoxy; arylamino; amido, alkylcarbonyl, arylcarbonyl; alkoxycarbonyl; aryloxy; aryloxycarbonyl; haloalkylcarbonyl; haloalkoxycarbonyl; alkylthiocarbonyl; arylthiocarbonyl; acyloxymethoxycarbonyl; cycloalkyl; bicycloalkyl; aryl; acyl; benzoyl;

or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H and alkyl;

or

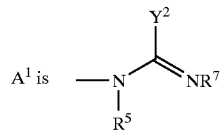

wherein $Y^2$ is selected from the group consisting of alkyl; cycloalkyl; bicycloalkyl; aryl; monocyclic heterocycles;

$Z_1$ is selected from the group consisting of $CH_2$, $CH_2O$, O, NH, CO, S, SO, CH(OH) and $SO_2$;

$Z_2$ is a 1–5 carbon linker optionally containing one or more heteroatom selected from the group consisting of O, S and N; alternatively $Z_1$–$Z_2$ may further contain a carboxamide, sulfone, sulfonamide, alkenyl, alkynyl, or acyl group;

wherein the carbon and nitrogen atoms of $Z_1$–$Z_2$ are optionally substituted by alkyl, alkoxy, thioalkyl, alkylsulfone, aryl, alkoxyalkyl, hydroxy, alkylamino, heteroaryl, alkenyl, alkynyl, carboxyalkyl, halogen, haloalky or acylamino;

n is an integer 0, 1 or 2;

$R^c$ is selected from the group consisting of hydrogen; alkyl; halogen, hydroxy, nitro, alkoxy, amino, haloalkyl, aryl, heteroaryl, alkoxyalkyl, aminoalkyl, hydroxyalkyl, thioalkyl, alkylamino, arylamino, alkylsulfonylamino, acyl, acylamino, sulfonyl, sulfonamide, allyl, alkenyl, methylenedioxy, ethylenedioxy, alkynyl, alkynylalkyl, carboxy, alkoxycarbonyl, carboxamido, cyano, and —$(CH_2)_n$COR wherein n is 0–2 and R is selected from hydroxy, alkoxy, alkyl and amino;

X is selected from the group consisting of —$CHR^e$—, —$NR^f$—, —O—, —S—, —$SO_2$—, and CO wherein $R^e$ is H, lower alkyl, alkoxy, cycloalkyl, alkoxyalkyl, hydroxy, alkynyl, alkenyl, haloalkyl, thioalkyl or aryl; wherein when $R^e$ is hydroxy the hydroxy can optionally form a lactone with the carboxylic acid function of the chain; wherein $R^f$ is selected from the group consisting of H, alkyl, aryl, benzyl and haloalkyl;

Y is selected from the group consisting of —$CR^g$— or —N— wherein $R^g$ is selected from the group consisting of H, alkyl, haloalkyl, alkoxyalkyl, alkynyl, aryl, heteroaryl, aralkyl, hydroxy, alkoxy, and carboxyalkyl;

optionally the group X-Y can contain a moiety selected from the group consisting of acyl, alkyl, sulfonyl, amino, ether, thioether, carboxamido, sulfonamido and olefin;

$R^b$ is $X_2$—$R^h$ wherein $X_2$ is selected from the group consisting of O, S and $NR^j$ wherein $R^h$ and $R^i$ are independently selected from the group consisting of H, alkyl, aryl, aralkyl, acyl, and alkoxyalkyl; and $R^a$ is selected from the group consisting of hydrogen, alkyl, alkenyl, alkoxyalkyl, hydroxyalkyl, alkynyl, alkynylalkyl, alkenylalkyl, haloalkyl, aryl, heteroaryl, aralkyl, heteroaralkyl, cycloalkyl, carboxyl, amino, alkylamino, alkoxycarbonyl, carboxamido, hydroxy, cyano, alkoxy, thioalkyl, acyclamino, sulfonylamino, alkylsulfonyl, and —$(CH_2)_n$ $COR^b$ wherein n is 0–2 and $R^b$ is as defined above.

It is another object of the invention to provide pharmaceutical compositions comprising compounds of the Formula 1. Such compounds and compositions are useful in selectively inhibiting or antagonizing the $\alpha_v\beta_3$ and/or $\alpha_v\beta_5$ integrins and therefore in another embodiment the present invention relates to a method of selectively inhibiting or antagonizing the $\alpha_v\beta_3$ and/or $\alpha_v\beta_5$ integrin. The invention further involves treating or inhibiting pathological conditions associated therewith such as osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, periodontal disease, psoriasis, smooth muscle cell migration and restenosis in a mammal in need of such treatment. Additionally, such pharmaceutical agents are useful as antiviral agents, and antimicrobials. The compounds of the present invention may be used alone or in combination with other pharmaceutical agents.

DETAILED DESCRIPTION

The present invention relates to a class of compounds represented by the Formula 1, described above.

In another embodiment of the present invention

is aryl, heteroaryl or fused aryl optionally substituted by one or more substituents selected from lower alkyl, halogen, alkoxy, hydroxy, cyano, amino, alkylamino, dialkylamino or methylsulfonamide.

Other embodiments of

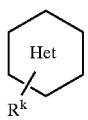

include the following heterocyclic ring systems containing at least one nitrogen atom:

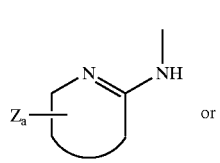

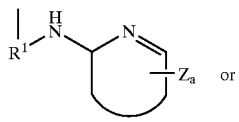

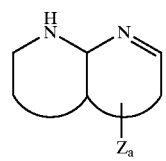

wherein $Z^a$ is H, alkyl, alkoxy, hydroxy, amino, alkylamino, dialkylamino, carboxyl, alkoxycarbonyl, hydroxyalkyl, halogen or haloalkyl and R is H, alkyl, alkoxyalkyl, acyl, haloalkyl or alkoxycarbonyl. More specifically some preferred embodiments include pyridylamino, imidazolylamino, oxazolylamino, thiazolylamino, pyrimidinylamino, quinoline, isoquinoline, tetrahydroquinoline, imidazopyridine, benzimidazole, pyridone or quinolone.

The following heteroaryls include the ring systems described above.

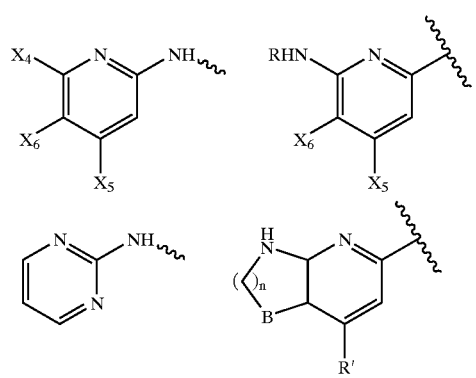

B = $CH_2$, O, CO, S, $CF_2$, $SO_2$, NR
R' = OR, OH, H, Me n = 1 or 2

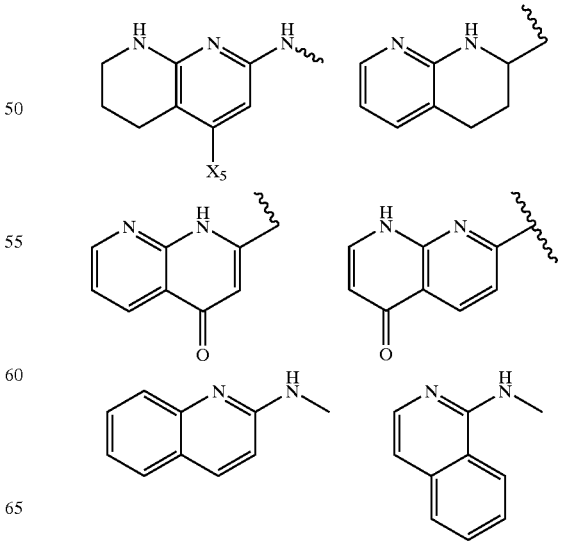

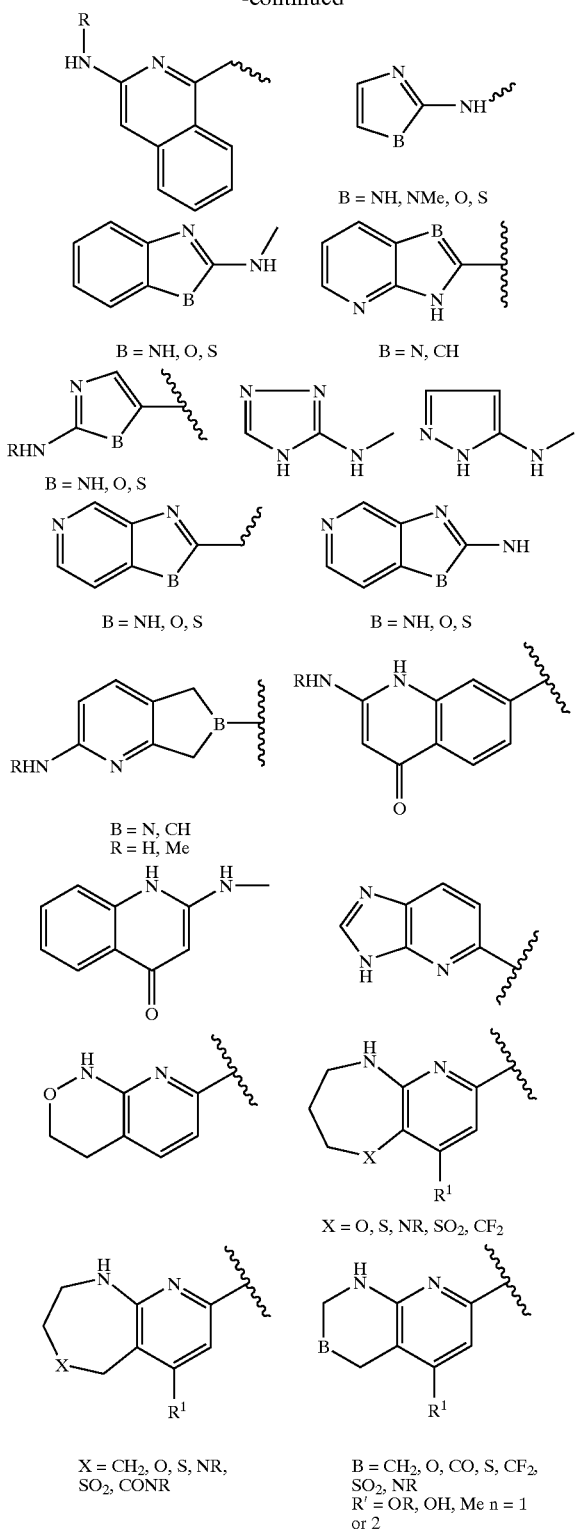

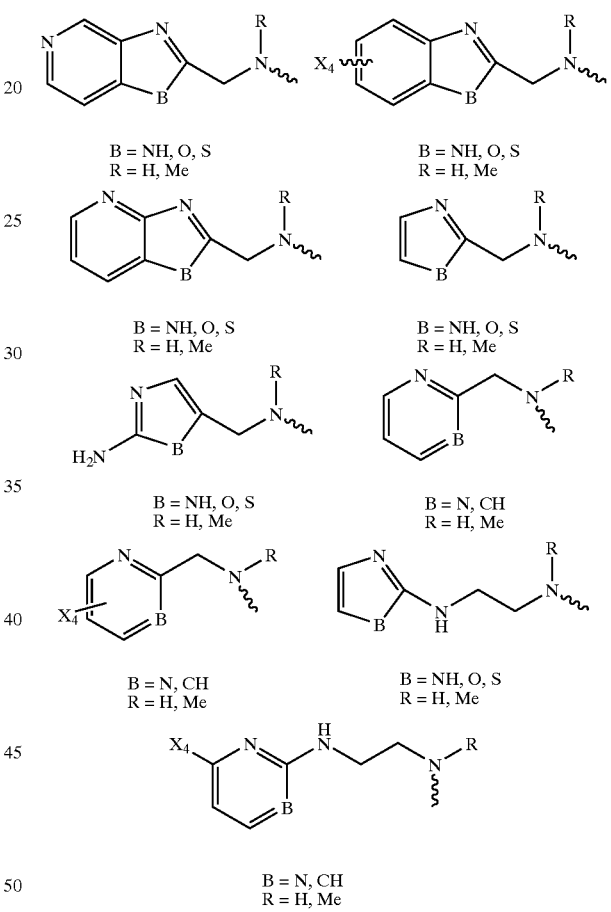

For the pyridyl derived heterocycle, the substituents $X_4$ and $X_5$ are preferentially H, alkyl, branched alkyl, alkylamino, alkoxyalkylamino, haloalkyl, thioalkyl, halogen, amino, alkoxy, aryloxy, alkoxyalkyl, hydroxy, cyano or acylamino groups. In another embodiment of the invention, the substituents $X_4$ and $X_5$ can be methyl, methoxy, amine, methylamine, trifluoromethyl, dimethylamine, hydroxy, chloro, bromo, fluoro and cyano. $X_6$ may preferentially be H, alkyl, halogen, alkoxy or haloalkyl. Alternately, the pyridyl ring can be fused with a 4–8 membered ring, optionally saturated or unsaturated. Some examples of these ring systems include quinoline, tetrahydroquinoline, azaquinoline, imidazopyridine and the like. The monocyclic ring systems such as imidazole, thiazole, oxazole, and the like, may contain an amino or alkylamino substituent at any position within the ring.

In another embodiment of the present invention, when $Z_1$ of Formula 1 is CO or $SO_2$, the linkage A—$Z_2$ of Formula 1 preferentially includes the following heterocycle derived ring systems: pyridine, imidazole, thiazole, oxazole, benzimidazole, imidazopyridine and the like.

Other heterocycles for $A^1$—$Z_2$ of the present invention include wherein $X_4$ is as defined above.

The substituent $R^c$ is preferably alkyl, halogen, alkoxy, hydroxy, haloalkyl, cyano, a carboxyl derivative or methyl sulfonamide. $R^e$ is preferably H, methyl, hydroxy or methoxy and $R^f$ is preferably H or alkyl.

X-Y is preferentially selected from the group consisting of —$CHR^e$—CH—, —$CHR^e$N—, —CO—$CR^g$—, —$NR^f$CH—, —$CR^e$=C—, —$OCR^g$—, —$SCR^g$—, —$SO_2$—$CR^g$— or —$SO_2$N— wherein $R^e$, $R^f$ and $R^g$ are as defined above.

In another embodiment, $R^a$ is an aryl or a heteroaryl group selected from phenyl, benzofuran, benzothiophene, indole, quinoline, isoquinoline, benzimidazole, benzoxazole, 1,3-benzodioxole, 1,4-benzodioxane, benzopyran, quinolone, imidazopyridine, tetrahydroquinoline, benzotriazole, dihydroindole, dihydrobenzofuran, furan, thiophene, phenyl, oxazole, thiazole, isoxazole, pyrazole, imidazole, pyrrole, pyridine, pyrimidine, pyridone, triazole, thiadiazole and the like. The aryl system can be optionally substituted at one or more position with alkyl, alkoxy, hydroxy, cyano, halogen or haloalkyl. In another embodiment of the present invention, $R^a$ may be an amine, alkylamine, acylamine, aminosulfone ($NHSO_2R$), arylamine, alkoxyalkylamine, aralkylamine, or heterocyclic amine.

The invention further relates to pharmaceutical compositions containing therapeutically effective amounts of the compounds of Formula 1.

The invention also relates to a method of selectively inhibiting or antagonizing the $\alpha_v\beta_3$ integrin and/or the $\alpha_v\beta_5$ integrin and more specifically relates to a method of inhibiting bone resorption, periodontal disease, osteoporosis, humoral hypercalcemia of malignancy, Paget's disease, tumor metastasis, solid tumor growth (neoplasia), angiogenesis, including tumor angiogenesis, retinopathy including macular degeneration and diabetic retinopathy, arthritis, including rheumatoid arthritis, smooth muscle cell migration and restenosis by administering a therapeutically effective amount of a compound of the Formula 1 to achieve such inhibition together with a pharmaceutically acceptable carrier.

The following is a list of definitions of various terms used herein:

As used herein, the terms "alkyl" or "lower alkyl" refer to a straight chain or branched chain hydrocarbon radicals having from about 1 to about 10 carbon atoms, and more preferably 1 to about 6 carbon atoms. Examples of such alkyl radicals are methyl, ethyl, n-propyl, isopropyl, n-butyl, isobutyl, sec-butyl, t-butyl, pentyl, neopentyl, hexyl, isohexyl, and the like.

As used herein the terms "alkenyl" or "lower alkenyl" refer to unsaturated acyclic hydrocarbon radicals containing at least one double bond and 2 to about 6 carbon atoms, which carbon-carbon double bond may have either cis or trans geometry within the alkenyl moiety, relative to groups substituted on the double bond carbons. Examples of such groups are ethenyl, propenyl, butenyl, isobutenyl, pentenyl, hexenyl and the like.

As used herein the terms "alkynyl" or "lower alkynyl" refer to acyclic hydrocarbon radicals containing one or more triple bonds and 2 to about 6 carbon atoms. Examples of such groups are ethynyl, propynyl, butynyl, pentynyl, hexynyl and the like.

The term "cycloalkyl" as used herein means saturated or partially unsaturated cyclic carbon radicals containing 3 to about 8 carbon atoms and more preferably 4 to about 6 carbon atoms. Examples of such cycloalkyl radicals include cyclopropyl, cyclopropenyl, cyclobutyl, cyclopentyl, cyclohexyl, 2-cyclohexen-1-yl, and the like.

The term "aryl" as used herein denotes aromatic ring systems composed of one or more aromatic rings. Preferred aryl groups are those consisting of one, two or three aromatic rings. The term embraces aromatic radicals such as phenyl, pyridyl, naphthyl, thiophene, furan, biphenyl and the like.

As used herein, the term "cyano" is represented by a radical of the formula 3

The terms "hydroxy" and "hydroxyl" as used herein are synonymous and are represented by a radical of the formula 4

The term "lower alkylene" or "alkylene" as used herein refers to divalent linear or branched saturated hydrocarbon radicals of 1 to about 6 carbon atoms.

As used herein the term "alkoxy" refers to straight or branched chain oxy containing radicals of the formula $-OR^{20}$, wherein $R^{20}$ is an alkyl group as defined above. Examples of alkoxy groups encompassed include methoxy, ethoxy, n-propoxy, n-butoxy, isopropoxy, isobutoxy, sec-butoxy, t-butoxy and the like.

As used herein the terms "arylalkyl" or "aralkyl" refer to a radical of the formula 5

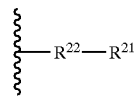

wherein $R^{21}$ is aryl as defined above and $R^{22}$ is an alkylene as defined above. Examples of aralkyl groups include benzyl, pyridylmethyl, naphthylpropyl, phenethyl and the like.

As used herein the term "nitro" is represented by a radical of the formula 5

As used herein the term "halo" or "halogen" refers to bromo, chloro, fluoro or iodo.

As used herein the term "haloalkyl" refers to alkyl groups as defined above substituted with one or more of the same or different halo groups at one or more carbon atom. Examples of haloalkyl groups include trifluoromethyl, dichloroethyl, fluoropropyl and the like.

As used herein the term "carboxyl" or "carboxy" refers to a radical of the formula —COOH.

As used herein the term "carboxyl ester" refers to a radical of the formula $-COOR^{23}$ wherein $R^{23}$ is selected from the group consisting of H, alkyl, aralkyl or aryl as defined above.

As used herein the term "carboxyl derivative" refers to a radical of the formula 7

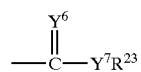

wherein $Y^6$ and $Y^7$ are independently selected from the group consisting of O, N or S and $R^{23}$ is selected from the group consisting of H, alkyl, aralkyl or aryl as defined above.

As used herein the term "amino" is represented by a radical of the formula —NH$_2$.

As used herein the term "alkylsulfonyl" or "alkylsulfone" refers to a radical of the for

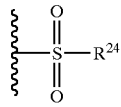

formula 6 wherein $^{24}$ is alkyl as defined above.

As used herein the term "alkylthio" refers to a radical of the formula —SR$^{24}$ wherein R$^{24}$ is alkyl as defined above.

As used herein the term "sulfonic acid" refers to a radical of the

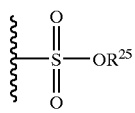

formula7 wherein R$^{25}$ is alkyl as defined above.

As used herein the term "sulfonamide" or "sulfonamido" refers to a radical of the formula

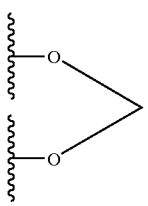

8wherein R$^7$ and R$^8$ are as defined above.

As used herein the term "fused aryl" refers to an aromatic ring such as the aryl groups defined above fused to one or more phenyl rings. Embraced by the term "fused aryl" is the radical naphthyl and the like.

As used herein the terms "monocyclic heterocycle" or "monocyclic heterocyclic" refer to a monocyclic ring containing from 4 to about 12 atoms, and more preferably from 5 to about 10 atoms, wherein 1 to 3 of the atoms are heteroatoms selected from the group consisting of oxygen, nitrogen and sulfur with the understanding that if two or more different heteroatoms are present at least one of the heteroatoms must be nitrogen. Representative of such monocyclic heterocycles are imidazole, furan, pyridine, oxazole, pyran, triazole, thiophene, pyrazole, thiazole, thiadiazole, and the like.

As used herein the term "fused monocyclic heterocycle" refers to a monocyclic heterocycle as defined above with a benzene fused thereto. Examples of such fused monocyclic heterocycles include benzofuran, benzopyran, benzodioxole, benzothiazole, benzothiophene, benzimidazole and the like.

As used herein the term "methylenedioxy" refers to the radical and the term "ethylenedioxy" refers to the radical

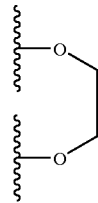

As used herein the term "4–12 membered dinitrogen containing heterocycle refers to a radical of the formula

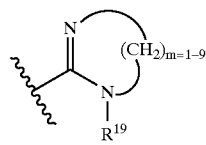

wherein m is 1 or 2 and R$^{19}$ is H, alkyl, aryl, or aralkyl and more preferably refers to 4–9 membered ring and includes rings such as imidazoline.

As used herein the term "5-membered optionally substituted heteroaromatic ring" includes for example a radical of the formula

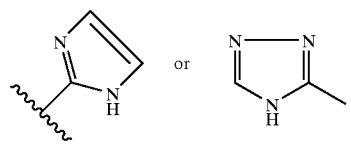

and "5-membered heteroaromatic ring fused with a phenyl" refers to such a "5-membered heteroaromatic ring" with a phenyl fused thereto. Representative of such 5-membered heteroaromatic rings fused with a phenyl is benzimidazole.

As used herein the term "bicycloalkyl" refers to a bicyclic hydrocarbon radical containing 6 to about 12 carbon atoms which is saturated or partially unsaturated.

As used herein the term "acyl" refers to a radical of the formula

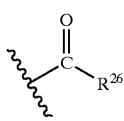

12 wherein R$^{26}$ is alkyl, alkenyl, alkynyl, aryl or aralkyl and optionally substituted thereon as defined above. Encompassed by such radical are the groups acetyl, benzoyl and the like.

As used herein the term "thio" refers to a radical of the formula 13

As used herein the term "sulfonyl" refers to a radical of the formula

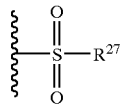

14 $R^{27}$ is alkyl, aryl or aralkyl as defined above.

As used herein the term "haloalkylthio" refers to a radical of the formula —S—$R^{28}$ wherein $R^{28}$ is haloalkyl as defined above.

As used herein the term "aryloxy" refers to a radical of the formula

wherein $R^{29}$ is aryl as defined above.

As used herein the term "acylamino" refers to a radical of the formula

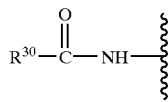

wherein $R^+$ is alkyl, aralkyl or aryl as defined above.

As used herein the term "amido" refers to a radical of the formula

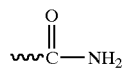

16.

As used herein the term "alkylamino" refers to a radical of the formula —$NHR^{32}$ wherein $R^{32}$ is alkyl as defined above.

As used herein the term "dialkylamino" refers to a radical of the formula —$NR^{33}R^{34}$ wherein $R^{33}$ and $R^{34}$ are the same or different alkyl groups as defined above.

As used herein the term "trifluoromethyl" refers to a radical of the formula

As used herein the term "trifluoroalkoxyl" refers to a radical of the formula

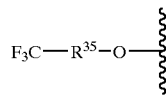

18 wherein $R^{35}$ is a bond or an alkylene as defined above.

As used herein the term "alkylaminosulfonyl" or "aminosulfonyl" refers to a radical of the formula19

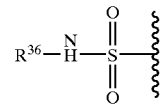

wherein $R^{36}$ is alkyl as defined above.

As used herein the term "alkylsulfonylamino" or "alkylsulfonamide" refers to a radical of the formula20

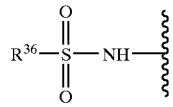

wherein $R^{36}$ is alkyl as defined above.

As used herein the term "trifluoromethylthio" refers to a radical of the formula

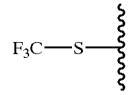

21

As used herein term "trifluoromethylsulfonyl" refers to a radical of the formula

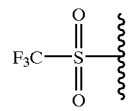

22.

As used herein the term "4–12 membered mono-nitrogen containing monocyclic or bicyclic ring" refers to a saturated or partially unsaturated monocyclic or bicyclic ring of 4–12 atoms and more preferably a ring of 4–9 atoms wherein one atom is nitrogen. Such rings may optionally contain additional heteroatoms selected from nitrogen, oxygen or sulfur. Included within this group are morpholine, piperidine, piperazine, thiomorpholine, pyrrolidine, azacycloheptene and the like.

As used wherein the term "benzyl" refers to the radical

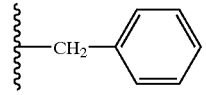

23.

As used herein the term "phenethyl" refers to the radical

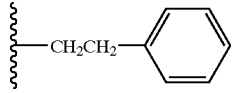

24.

As used herein the term "4–12 membered mono-nitrogen containing monosulfur or monooxygen containing heterocyclic ring" refers to a ring consisting of 4 to 12 atoms and more preferably 4 to 9 atoms wherein at least one atom is a nitrogen and at least one atom is oxygen or sulfur. Encompassed within this definition are rings such as thiazoline and the like.

As used herein term "arylsulfonyl" or "arylsulfone" refers to a radical of the formula 25

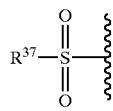

wherein $R^{37}$ is aryl as defined above.

As used herein the terms "alkylsulfoxide" or "arylsulfoxide" refer to radicals of the formula

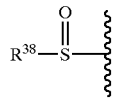

26 wherein $R^{38}$ is, respectively, alkyl or aryl as defined above.

As used herein the term "arylthio" refers to a radical of the formula 27

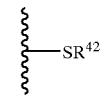

wherein $R^{42}$ is aryl as defined above.

As used herein the term "monocyclic heterocycle thio" refers to a radical of the formula

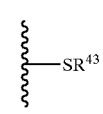

28 wherein $R^{43}$ is a monocyclic heterocycle radical as defined above.

As used herein the terms "monocyclic heterocycle sulfoxide" and "monocyclic heterocycle sulfone" refer, respectively, to radicals of the formula 29 30

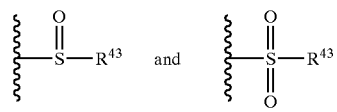

wherein $R^{43}$ is a monocyclic heterocycle radical as defined above.

As used herein the term "alkylcarbonyl" refers to a radical of the formula

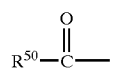

31 wherein $R^{50}$ is alkyl as defined above.

As used herein the term "arylcarbonyl" refers to a radical of the formula

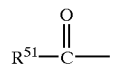

32 wherein $R^{51}$ is aryl as defined above.

As used herein the term "alkoxycarbonyl" refers to a radical of the formula

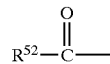

33 wherein $R^{52}$ is alkoxy as defined above.

As used herein e term "aryloxycarbonyl" refers to a radical of the formula

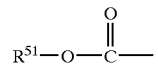

34 wherein $R^{51}$ is aryl as defined above.

As used herein term "haloalkylcarbonyl" refers to a radical of the formula

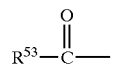

35 wherein $R^{53}$ is haloalkyl as defined above.

As used herein the term "haloalkoxycarbonyl" refers to a radical of the formula

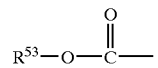

36 wherein $R^{53}$ is haloalkyl as defined above.

As used herein the term "alkylthiocarbonyl" refers to a radical of the formula

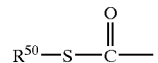

37 wherein $R^{50}$ is alkyl as defined above.

As used herein the term "arylthiocarbonyl" refers to a radical of the formula

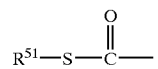

38 wherein $R^{51}$ is aryl as defined above.

As used herein the term "acyloxymethoxycarbonyl" refers to a radical of the formula

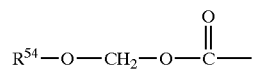

39 wherein $R^{54}$ is acyl as defined above.

As used herein the term "arylamino" refers to a radical of the formula $R^{51}$—NH— wherein $R^{51}$ is aryl as defined above.

As used herein the term "acyloxy" refers to a radical of the formula $R^{55}$—O— wherein $R^{55}$ is acyl as defined above.

As used herein the term "alkenylalkyl" refers to a radical of the formula $R^{50}$—$R^{57}$— wherein $R^{50}$ is an alkenyl as defined above and $R^{57}$ is alkylene as defined above.

As used herein the term "alkenylene" refers to a linear hydrocarbon radical of 1 to about 8 carbon atoms containing at least one double bond.

As used herein the term "alkoxyalkyl" refers to a radical of the formula $R^{56}$—$R^{57}$— wherein $R^{56}$ is alkoxy as defined above and $R^{57}$ is alkylene as defined above.

As used herein the term "alkynylalkyl" refers to a radical of the formula $R^{59}—R^{60}—$ wherein $R^{59}$ is alkynyl as defined as above and $R^{60}$ is alkylene as defined as above.

As used herein the term "alkynylene" refers to divalent alkynyl radicals of 1 to about 6 carbon atoms.

As used herein the term "allyl" refers of a radical of the formula $—CH_2CH=CH_2$.

As used herein the term "aminoalkyl" refers to a radical of the formula $H_2N—R^{61}$ wherein $R^{61}$ is alkylene as defined above.

As used herein the term "benzoyl" refers to the aryl radical $C_6H_5—CO—$.

As used herein the term "carboxamide" or "carboxamido" refer to a radical of the formula $—CO—NH_2$.

As used herein the term "carboxyalkyl" refers to a radical $HOOC—R^{62}—$ wherein $R^{62}$ is alkylene as defined as above.

As used herein the term "carboxylic acid" refers to the radical $—COOH$.

As used herein the term "ether" refers to a radical of the formula $R^{63}—O—$ wherein $R^{63}$ is selected from the group consisting of alkyl, aryl and heteroaryl.

As used herein the term "haloalkylsulfonyl" refers to a radical of the formula

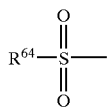

wherein the $R^{64}$ is haloalkyl as defined above.

As used herein the term "heteroaryl" refers to an aryl radical contain at least one heteroatom.

As used herein the term "hydroxyalkyl" refers to a radical of the formula $HO—R^{65}—$ wherein $R^{65}$ is alkylene as defined above.

As used herein the term "keto" refers to a carbonyl group joined to 2 carbon atoms.

As used herein the term "lactone" refers to an anhydro cyclic ester produced by intramolecular condensation of a hydroxy acid with the elimination of water.

As used herein the term "olefin" refers to an unsaturated hydrocarbon radical of the type $C_nH_{2n}$.

As used herein the term "sulfone" refers to a radical of the formula $R^{66}—SO_2—$.

As used herein the term "thioalkyl" refers to a radical of the formula $R^{77}—S—$ wherein $R^{77}$ is alkyl as defined above.

As used herein the term "thioether" refers to a radical of the formula $R^{78}—S—$ wherein $R^{78}$ is alkyl, aryl or heteroaryl.

As used herein the term "trifluoroalkyl" refers to an alkyl radical as defined above substituted with three halo radicals as defined above.

The term "composition" as used herein means a product which results from the mixing or combining of more than one element or ingredient.

The term "pharmaceutically acceptable carrier", as used herein means a pharmaceutically acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The following is a list of abbreviations and the corresponding meanings as used interchangeably herein:

$^1$H-NMR=proton nuclear magnetic resonance
AcOH=acetic acid
Ar=Argon
BOC=tert-butoxycarbonyl
BuLi=butyl lithium
Cat.=catalytic amount
$CH_2Cl_2$=dichloromethane
$CH_3CN$=acetonitrile
$CH_3I$=iodomethane
CHN analysis=carbon/hydrogen/nitrogen elemental analysis
CHNCl analysis=carbon/hydrogen/nitrogen/chlorine elemental analysis
CHNS analysis=carbon/hydrogen/nitrogen/sulfur elemental analysis
DEAD=diethylazodicarboxylate
DIAD=diisopropylazodicarboxylate
DI water=deionized water
DMA=N,N-dimethylacetamide
DMAC=N,N-dimethylacetamide
DMF=N,N-dimethylformamide
EDC=1-(3-dimethylaminopropyl)-3-ethylcarbodiimide hydrochloride
Et=ethyl
Eti=ethyl iodide
$Et_2O$=diethyl ether
$Et_3N$=triethylamine
EtOAc=ethyl acetate
EtOH=ethanol
FAB MS=fast atom bombardment mass spectroscopy
g=gram(s)
HCl=hydrochloric acid
HOBT=1-hydroxybenzotriazole hydrate
hplc=high performance liquid chromatography
HPLC=high performance liquid chromatography
i-Pr=iso propyl
i-Prop=iso propyl
$K_2CO_3$=potassium carbonate
KF=potassium fluoride
$KMnO_4$=potassium permanganate
KOH=potassium hydroxide
KSCN=potassium thiocyanate
L=Liter
LiOH=lithium hydroxide
Me=methyl
MeOH=methanol
mg=milligram
$MgSO_4$=magnesium sulfate
ml=milliliter
mL=milliliter
MS=mass spectroscopy
NaH—sodium hydride
$NaHCO_3$=sodium bicarbonate
NaOH=sodium hydroxide
NaOMe=sodium methoxide NH$_4^+$HCO$_2$=ammonium formate
NH$_4$OH=ammonium hydroxide
NMR=nuclear magnetic resonance
Pd=palladium
Pd/C=palladium on carbon
Ph=phenyl
psi=pressure per square inch
Pt=platinum
Pt/C=platinum on carbon
RP HPLC=reverse phase high performance liquid chromatography
RT=room temperature
t-BOC=tert-butoxycarbonyl
TFA=trifluoroacetic acid
THF=tetrahydrofuran
TLC—thin layer chromatography
TMS=trimethylsilyl
Δ=heating the reaction mixture The compounds as shown above can exist in various isomeric forms and all such isomeric forms are meant to be included. Tautomeric forms are also included as well as pharmaceutically acceptable salts of such isomers and tautomers.

In the structures and formulas herein, a bond drawn across a bond of a ring can be to any available atom on the ring.

The term "pharmaceutically acceptable salt" refers to a salt prepared by contacting a compound of Formula 1 with an acid whose anion is generally considered suitable for human consumption. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid. Representative salts include the following: acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylgucamine ammonium salt, oleate, oxalate, pamoate (embonate), palmitate, pantothenate, phosphate/disphosphate, polygalacturonate, salicylate, stearate, sulfate, subacetate, succinate, tannate, tartrate, teociate, tosylate, triethiodide and valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. All of the pharmacologically acceptable salts may be prepared by conventional means. (See Berge et al., *J Pharm. Sci.,* 66(1), 1–19 (1977) for additional examples of pharmaceutically acceptable salts.)

The compounds of the present invention can have chiral centers and occur as racemates, racemic mixtures, diastereomeric mixtures, and as individual diastereomers or enantiomers, with all isomeric forms included in the present invention. Therefore, where a compound is chiral, the separate enantiomers or diastereomers, substantially free of the other, are included within the scope of the present invention; further included are all mixtures of the enantiomers or diastereomers. Also included within the scope of the invention are polymorphs, or hydrates or other modifiers of the compounds of invention.

The present invention includes within its scope prodrugs of the compounds of this invention. In general, such prodrugs will be functional derivatives of the compounds of this invention which are readily convertible in vivo into the required compound. For example, prodrugs of a carboxylic acid may include an ester, an amide, an ortho-ester, or heterocycles such as tetrazole. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

For the selective inhibition or antagonism of $\alpha_v\beta_3$ and/or $\alpha_v\beta_5$ integrins, compounds of the present invention may be administered orally, parenterally, or by inhalation spray, or topically in unit dosage formulations containing conventional pharmaceutically acceptable carriers, adjuvants and vehicles. The term parenteral as used herein includes, for example, subcutaneous, intravenous, intramuscular, intrasternal, transmuscular infusion techniques or intraperitonally.

The compounds of the present invention are administered by any suitable route in the form of a pharmaceutical composition adapted to such a route, and in a dose effective for the treatment intended. Therapeutically effective doses of the compounds required to prevent or arrest the progress of or to treat the medical condition are readily ascertained by one of ordinary skill in the art using preclinical and clinical approaches familiar to the medicinal arts.

Accordingly, the present invention provides a method of treating conditions mediated by selectively inhibiting or antagonizing the $\alpha_v\beta_3$ and/or $\alpha_v\beta_5$ cell surface receptor which method comprises administering a therapeutically effective amount of a compound selected from the class of compounds depicted in the above formulas, wherein one or more compound is administered In association with one or more non-toxic, pharmaceutically acceptable carriers and/or diluents and/or adjuvants (collectively referred to herein as "carrier" materials) and if desired other active ingredients. More specifically, the present invention provides a method for selective inhibition of the $\alpha_v\beta_3$ and/or $\alpha_v\beta_5$ cell surface receptors with a reduced $\alpha_v\beta_6$ inhibition. Most preferably the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating retinopathy including macular degeneration and diabetic retinopathy, inhibiting arthritis, psoriasis and periodontal disease, and inhibiting smooth muscle cell migration including restenosis.

Based upon standard laboratory experimental techniques and procedures well known and appreciated by those skilled in the art, as well as comparisons with compounds of known usefulness, the compounds of Formula 1 can be used in the treatment of patients suffering from the above pathological conditions. One skilled in the art will recognize that selection of the most appropriate compound of the invention is within the ability of one with ordinary skill in the art and will depend on a variety of factors including assessment of results obtained in standard assay and animal models.

Some in vivo models of angiogenesis include the CAM (chick chorioallantoic membrane) assay (Vu et al., *Lab Invest.* 1985, 53, 4), the gelatin sponge/chorioallantoic membrane assay (Ribatti et al., *J. Vasc. Res.* 1997, 34, 6), the rabbit corneal micropocket assay () and the insertion of tumor cells in mice (Robertson et al., *Cancer Res.* 1999, 51, 1339). For a review of angiogenesis assays, see Auerbach et al., Pharmacol Ther 1991, 51, 1.

Treatment of a patient afflicted with one of the pathological conditions comprises administering to such a patient an amount of compound of the Formula 1 which is therapeutically effective in controlling the condition or in prolonging the survivability of the patient beyond that expected in the absence of such treatment. As used herein, the term "inhibition" of the condition refers to slowing, interrupting, arresting or stopping the condition and does not necessarily indicate a total elimination of the condition. It is believed that prolonging the survivability of a patient, beyond being a significant advantageous effect in and of itself, also indicates that the condition is beneficially controlled to some extent.

As stated previously, the compounds of the invention can be used in a variety of biological, prophylactic or therapeutic areas. It is contemplated that these compounds are useful in prevention or treatment of any disease state or condition wherein the $\alpha_v\beta_3$ and/or $\alpha_v\beta_5$ Integrin plays a role.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 1.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100, 200 and 500 milligrams of the active ingredient for the symptomatic adjustment of the dosage to the patient to be treated. A medicament typically contains from about 0.01 mg to about 500 mg of the active ingredient, preferably, from about 1mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittant throughout the dosage regiment.

For administration to a mammal in need of such treatment, the compounds in a therapeutically effective amount are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulphuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The pharmaceutical compositions useful in the present invention may be subjected to conventional pharmaceutical operations such as sterilization and/or may contain conventional pharmaceutical adjuvants such as preservatives, stabilizers, wetting agents, emulsifiers, buffers, etc.

The general synthetic sequences for preparing the compounds useful in the present invention are outlined in SCHEMES 1–8. Both an explanation of, and the actual procedures for, the various aspects of the present invention are described where appropriate. The following Schemes and Examples are intended to be merely illustrative of the present invention, and not limiting thereof in either scope or spirit. Those with skill in the art will readily understand that known variations of the conditions and processes described in the Schemes and Examples can be used to synthesize the compounds of the present invention.

SCHEME 1

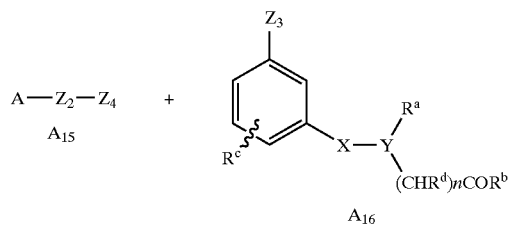

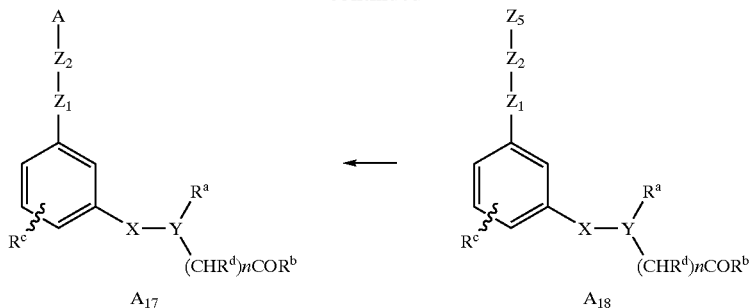

Scheme 1

The compounds of formula $A_{17}$ are generally prepared by reacting an intermediate of formula $A_{16}$ with a compound of the formula $A_{15}$. For example, when $Z_3$ is OH, SH or NHR, $A_{16}$ may be alkylated with $A_{15}$ ($Z_4$=Br or OMs) using a base such as sodium hydride or potassium hydride preferably in a solvent such as dimethylsulfoxide or DMF. These reactions may preferentially be carried at 0° C. to approximately 40° C. Alternatively, when $Z_3$ and $Z_4$ are both OH, the ether formation to product $A_{17}$ may be accomplished by using Mitsunobu reaction. This reaction may preferentially be carried out using a triarylphosphine such as triphenylphoshine, and azodicarboxylate, such as diethyl azodicarboxylate, di-tert-butyl azodicarboxylate, di-isopropyl azodicarboxylate, in solvents such as DMF, methylene chloride, THF and the like. When $Z_3$ carries a carboxylic acid or a sulfonic acid and $Z_4$ is an amine, the standard coupling conditions may be used to synthesize the carboxamide (CONH) or the sulfonamide ($SO_2NH$) containing $A_{17}$ compounds.

Alternately, the compounds of formula $A_{17}$ may be prepared by starting with compounds of general formula $A_{18}$. For example, when $Z_5$ in $A_{18}$ is $NH_2$, cyclic or acyclic guanidino containing compounds of formula $A_{17}$ may be synthesized by adopting the methodologies discussed in e. g. U.S. Pat. No. 5,852,210 or U.S. Pat. No. 5,773,646. Similarly, compounds of formula $A_{18}$ ($Z_5$=$NH_2$) may be treated with appropriately substituted heteroaromatic systems, such as 2-chloropyridine Noxide or 2-fluoropyridine, to give the compounds $A_{17}$. This reaction may preferentially be carried out by refluxing the intermediate $A_{18}$ and a 2-fluoropyridine, or 2-chloropyridine N-oxide, in solvents such as tert-butyl alcohol or tert-amyl alcohol in the presence of base, such as sodium bicarbonate, sodium carbonate, potassium carbonate or potassium bicarbonate. When compounds of the formula $A_{17}$ contain N-oxide e.g., pyridine N-oxide, the deoxygenation is carried out using e.g., transfer hydrogenation conditions (cyclohexene/Pd on carbon) or ammonium formate and Pd on carbon. The hydrolysis of the resulting ester may be carried out using an aqueous base, such as sodium hydroxide, lithium hydroxide or potassium hydroxide in solvents such as methanol, ethanol or THF.

Compounds of the general formula $A_{15}$, $A_{16}$, $A_{18}$ may be prepared by methodologies discussed in SCHEMES 2–8 below.

SCHEME 2

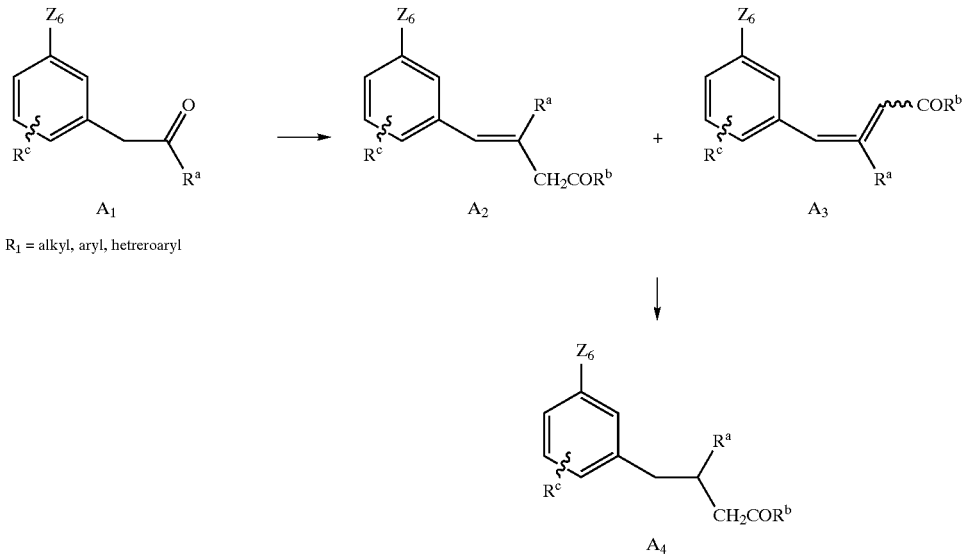

$R_1$ = alkyl, aryl, hetreroaryl

Scheme 2

Compounds of the formula $A_4$ may be prepared by starting with benzyl ketones $A_1$. Using Wittig or Horner-Emmons reaction, the compound $A_1$ is converted to the olefin containing intermediates $A_2$ and $A_3$. This reaction is carried out using a trialkyl phosphonoacetate, such as triethyl phosphonoacetate, trimethyl phosphonoacetate, and using a base such as sodium hydride, sodium methoxide, sodium ethoxide. This reaction is generally done at low temperatures (0–30° C.) and using THF or DMF as solvents. The isomeric mixtures of olefin containing compounds are hydrogenated using Pd on carbon or Pt on carbon as catalyst. This reduction is carried out under pressure of hydrogen (preferably 5–60 psi) to give the desired intermediate $A_4$. The intermediates $A_{2-A4}$ are processed to the compounds of Formula 1 using the synthetic transformations outlined in Scheme 1.

SCHEME 3

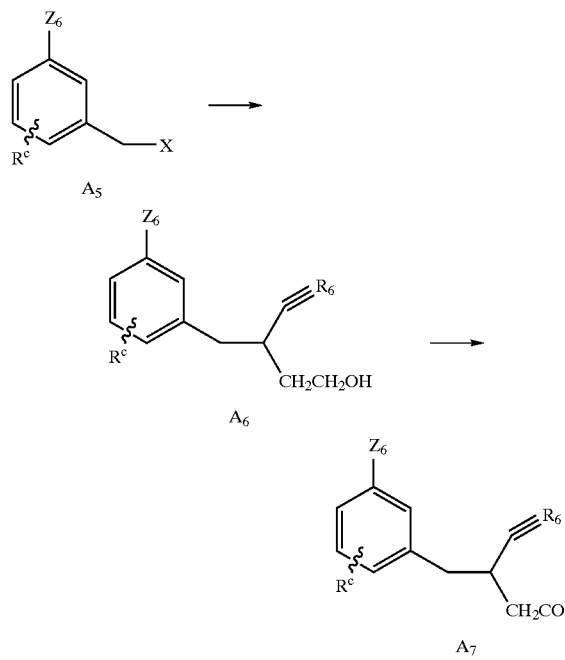

Scheme 3

Compounds of formula $A_7$ where $R_1$ is a substituted alkyne may be prepared using the methodology outlined in Scheme 3. Reaction of 4-pentyn-1-ol with substituted benzyl bromide in ethereal solvents such as THF, diethyl ether, dimethoxyethane and using a base such as tert-butyl lithium at low temperatures (preferably −30 to −78° C.) gives the intermediate $A_6$. Oxidation of the alcohol $A_6$ using e. g., Jones reagent or 2,2-tetramethylpiperidinyl-1-oxy and bleach gives the intermediate $A_7$. The preparative oxidation conditions described in literature (e.g., Tetrahedron 52, 11463, 1996; J. Org. Chem. 64, 2564, 1999) may be used to convert intermediate $A_6$ to $A_7$. When $R_6=SiMe_3$, the intermediate $A_6$ may be desilylated (using e.g., KF, DMF, $H_2O$) and coupled using Heck reaction to give aryl or heteroaryl ($R_6=Ar$) substituted $A_7$.

The intermediates $A_7$ are processed to the compounds of Formula 1 by using the synthetic transformations outlined in Scheme 1.

SCHEME 4

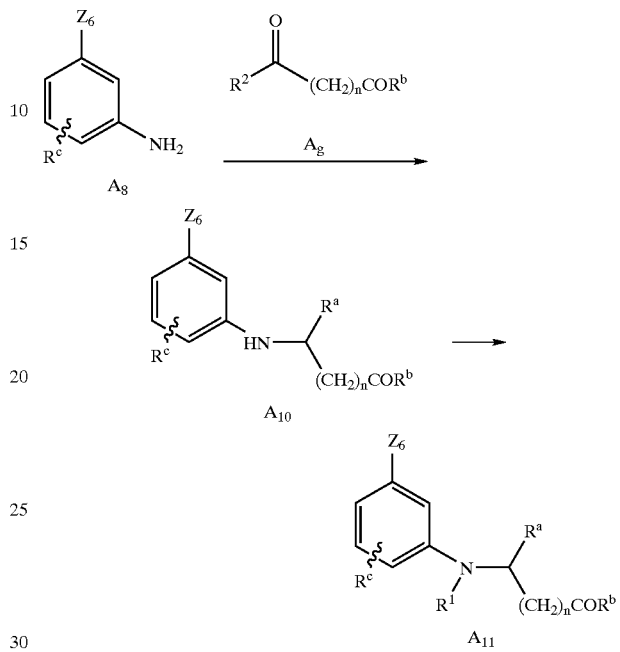

Scheme 4

Compounds of Formula 1 wherein X is nitrogen may be prepared as shown in general Scheme 4. Reductive amination of aniline $A_8$ with the appropriate keto-ester $A_9$ (e. g., ethyl acetoacetate or ethyl benzoylacetate) gives the intermediate $A_{10}$. This reduction is preferentially carried out using e. g., sodium cyanoborohydride in alcoholic solvents such as methanol or ethanol. The methodology described in J. Med. Chem., 36, 2984, 1993 may be utilized for this reaction. Alkylation of $A_{10}$ using suitable base (e. g., potassium carbonate or diisopropylethylamine) and alkyl or acyl halide gives $A_{11}$.

The intermediates $A_{10}$ and $A_{11}$ are processed to the compounds of Formula 1 using the synthetic transformations outlined in Scheme 1

SCHEME 5

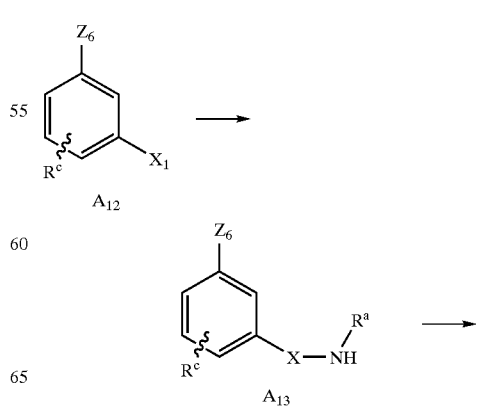

-continued

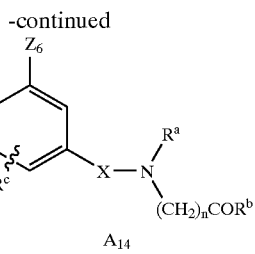

A$_{14}$

X$_1$ = COCl, SO$_2$Cl, CHO,

Scheme 5

Compounds of Formula 1, wherein X-Y is an amide, sulfonamide or alkylamine may be prepared as shown in general Scheme 5. Reaction of the substituted benzoyl chloride or aryl sulfonyl chloride (A$_{12}$, X$_1$=COCl, SO$_2$Cl), with alkyl or arylamine in the presence of a suitable base such as triethylamine gives the intermediate A$_{13}$. Similarly starting with substituted benzaldehyde (X$_1$=CHO), reductive amination with substituted aniline gives the intermediate A$_{13}$. The reductive amination may be carried out using the conditions discussed in Scheme 4. Alkylation of A$_{13}$ with e. g., ethyl bromoacetate in the presence of a suitable base, such as potassium carbonate, diisopropylethylamine, sodium hydride, gives the desired intermediate A$_{14}$.

Intermediates A$_{14}$ are processed to the compounds of Formula 1 using synthetic transformations outlined in Scheme 1.

The substituent Z$_6$ in Schemes 2–5 may be Z$_3$, protected Z$_3$ or converted to Z$_3$ by synthetic transformations. The reaction sequence may be modified using conventional reagents and methodologies depending upon the properties and reactivity of Z$_6$.

SCHEME 6

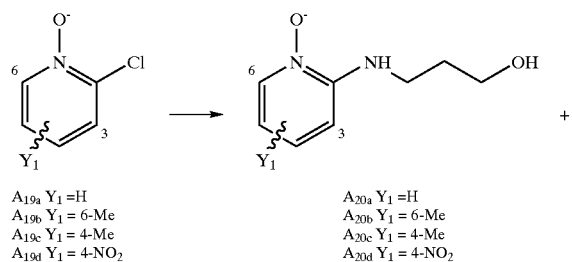

A$_{19a}$ Y$_1$ =H
A$_{19b}$ Y$_1$ = 6-Me
A$_{19c}$ Y$_1$ = 4-Me
A$_{19d}$ Y$_1$ = 4-NO$_2$

A$_{20a}$ Y$_1$ =H
A$_{20b}$ Y$_1$ = 6-Me
A$_{20c}$ Y$_1$ = 4-Me
A$_{20d}$ Y$_1$ = 4-NO$_2$

+

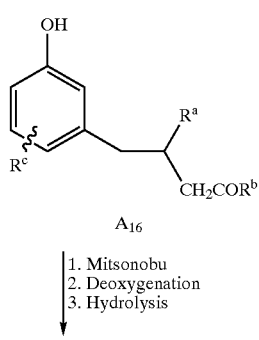

A$_{16}$

1. Mitsonobu
2. Deoxygenation
3. Hydrolysis

↓

-continued

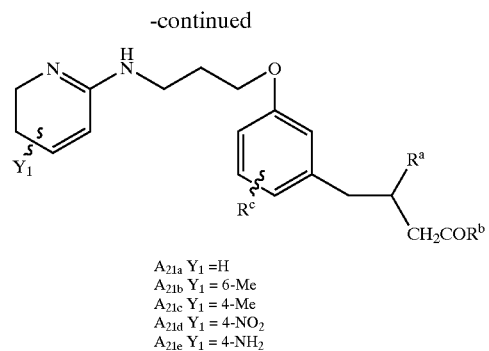

A$_{21a}$ Y$_1$ =H
A$_{21b}$ Y$_1$ = 6-Me
A$_{21c}$ Y$_1$ = 4-Me
A$_{21d}$ Y$_1$ = 4-NO$_2$
A$_{21e}$ Y$_1$ = 4-NH$_2$

Scheme 6

The compounds of Formula 1, wherein A is substituted pyridyl may be prepared by using the methodology set forth in the general synthetic Scheme 6. For example, reaction of substituted 2-halopyridine N-oxide (such as A$_{19a}$–A$_{19d}$) with e. g. 3-aminopropanol gives the intermediates A$_{20a}$–A$_{20d}$. This reaction may preferentially be carried out by refluxing the intermediate 2-halopyridine N-oxide, such as 2-chloropyridine N-oxide in solvents such as tert-butyl alcohol, or tert-amyl alcohol in the presence of a base such as sodium bicarbonate, sodium carbonate, potassium carbonate, or potassium bicarbonate. The preparative conditions described in WO 99/15508 (PCT US 98/19466) may be used for this transformation.

Coupling of the intermediates A$_{20a}$–A$_{20d}$ with A$_{16}$ (as obtained in Schemes 2 and 3) using Mitsunobu reaction gives the compounds containing the ether link. This reaction may preferentially be carried out using a triarylphosphine, such as triphenylphoshine and a dialkylazodicarboxylate, such as diethyl azodicarboxylate, di-tert-butyl azodicarboxylate, or di-iso-propyl azodicarboxylate in solvents such as DMF, methylene chloride, or THF.

N-deoxygenation of resulting intermediates followed by hydrolysis of the ester gives the target compounds (A$_{21a}$–A$_{21d}$). Reduction of the N-oxide bond may be accomplished using e. g., transfer hydrogenation (cyclohexene/Pd on carbon) or ammonium formate and Pd on carbon. The nitro group in A$_{21d}$ may be hydrogenated using Pd on carbon or Pt on carbon as catalysts. This transformation may be carried out using solvents such as methanol, ethanol or THF. The hydrolysis of the ester group may be carried using an aqueous base, such as sodium hydroxide, lithium hydroxide or potassium hydroxide in solvents such as methanol, ethanol or THF.

Compounds of the Formula 1 containing heterocycles other than pyridyl can also be prepared using the methodology of Scheme 6 above. For example, reacting 2-bromopyrimidine or 1-chloroisoquinoline N-oxide with 3-aminopropanol gives the analogous intermediates as obtained in Step 1. The resulting intermediates could be elaborated as in Scheme 6 to give the pyrimidine and isoquinoline containing target compounds

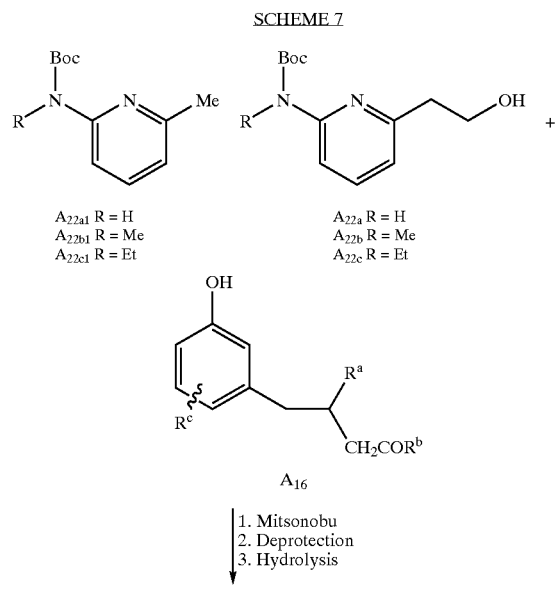

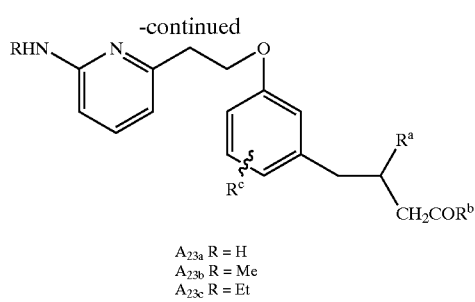

Scheme 7

Compounds of Formula 1 containing 6-amino substituents may be prepared as shown in Scheme 7. The intermediates $A_{22b}$ can be prepared as described in J. Med. Chem. 43, 22–26, 2000. Boc-protected 2-amino picoline $A_{22a1}$ or its ethylated product $A_{22c1}$ are elaborated to $A_{22a}$ and $A_{22c}$ as shown for example $A_{22b}$ in J. Med. Chem. 43, 22–26, 2000. The ethylated intermediate $A_{22c1}$ may be prepared from $A_{22a1}$ by alkylation using e.g. EtI and a base such as potassium carbonate or cesium carbonate. This reaction may preferably be carried out in polar solvents such as dimethylformamide, or dimethylacetamide. Mitsunobu reaction of $A_{16}$ with $A_{22a}$–$A_{22c}$ as discussed in Scheme 6, gives the compounds containing the phenol ether. Removal of the Boc group using e. g., trifluoroacetic acid in solvents such as dichloromethane, followed by hydrolysis of the ester group as described in Scheme 6 above gives the target compounds ($A_{23a}$–$A_{23c}$).

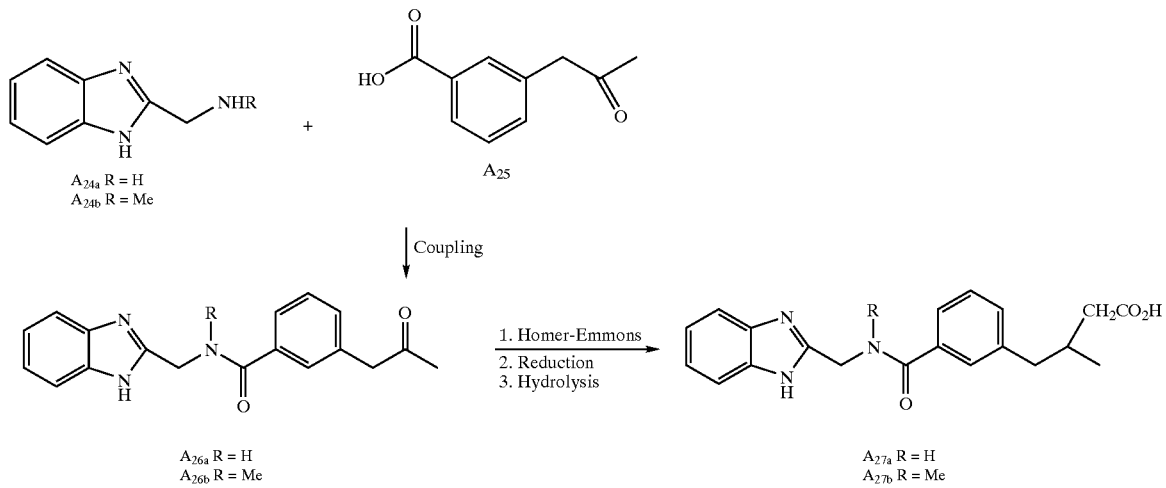

Scheme 8

Compounds of Formula 1, wherein $Z_f$ is CO can be prepared as illustrated in Scheme 8. The starting material $A_{24a}$ can be purchased commercially and $A_{24b}$ can be prepared as described in J. Med. Chem 36, 320–330, 1993. Coupling of $A_{24a}$ or $A_{24b}$ with $A_{25}$ using reagents such as isobutyl chloroformate, EDC, or HOBT gives the amide containing intermediates $A_{26a}$ and $A_{26b}$. Reaction of benzyl ketone $A_{26a}$ and $A_{26b}$ with a trialkyl phosphonoacetate, such as triethyl phosphonoacetate, trimethyl phosphonoacetate using a base (e. g., sodium hydride, sodium methoxide, sodium ethoxide) gives the alkene intermediates as discussed in Scheme 2. The isomeric mixtures of olefin containing compounds are hydrogenated using e. g, Pd on carbon or Pt on carbon as catalyst. This reduction is carried under pressure of hydrogen (preferably 5–60 psi). The compounds $A_{27a}$ and $A_{27b}$ are prepared by hydrolysis of the resulting ester using e.g., 1 N NaOH in alcoholic solvents such as ethanol.

EXAMPLE 1

3-[[3-(2-pyridinylamino)propoxy]phenyl]propanoic acid

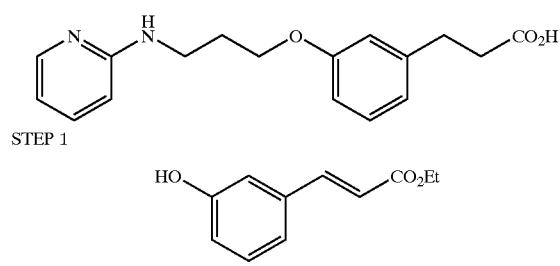

STEP 1

3-hydroxycinnamic acid (4.0 g) was dissolved in saturated HCl/EtOH (60 mL) and stirred overnight at room temperature. The mixture was concentrated under reduced pressure to give a yellow solid (4.6 g). $^1$H NMR was consistent with the proposed structure.

STEP 2

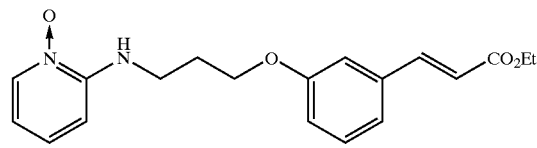

The product of Step 1 (1.0 g, 5.2 mmol) was dissolved in THF (20 mL). $PPh_3$ (6.2 mmol) and 2-(3-hydroxypropyl amino)pyridine N-oxide (5.2 mmol) were added, followed by a dropwise addition of DEAD (5.3 mmol). The reaction was stirred overnight at room temperature. The mixture was then concentrated in vacuo and purified by silica gel chromatography (eluents: 1:1 ethyl acetate/hexane; 94:5:1 $CH_2Cl_2$, MeOH, $NH_4OH$) to obtain a yellow oil (1.02 g). $^1$H NMR was consistent with the desired product.

Step 3

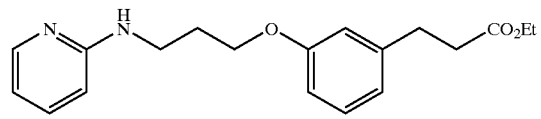

The yellow oil from Step 2 (300 mg) was dissolved in isopropyl alcohol under Ar. 10% Pd/C (240 mgs) was added, followed by 2.4 mL of cyclohexene. The reaction mixture was heated to reflux and stirred overnight. The mixture was then cooled and filtered through a plug of celite. The filtrate was concentrated to give a colorless oil (248 mg). $^1$H NMR was consistent with the desired product.

Step 4

The product from Step 3 was dissolved in MeOH (25 mL) and treated with 1 N NaOH (25 mL). After stirring overnight at room temperature, the reaction was concentrated in vacuo and purified by reverse phase HPLC ($H_2O/CH_3CN$). 90 mg of a colorless oil were obtained. $^1$H NMR, MS, and elemental analysis were consistent with the desired product.

Elemental analysis calculated for $C_{17}H_{20}N_2O_3 \cdot 1.0$ TFA, .0.8 $H_2O$: C, 53.22; H, 5.31; N, 6.53. Found: C, 53.30; H, 5.14; N, 6.42.

EXAMPLE 2

3-[[4-(2-pyridinylamino)butoxy]phenyl]propanoic acid

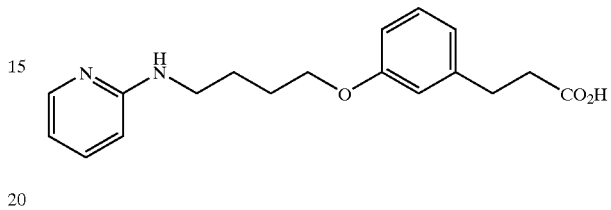

This compound was prepared in the same manner as described in Example 1, substituting 2-(4-hydroxybutylamino)pyridine N-oxide for 2-(3-hydroxypropylamino)pyridine N-oxide. $^1$H NMR, MS, and analytical analysis were consistent with the proposed structure.

Elemental analysis calculated for $C_{18}H_{22}N_2O_3 \cdot 1.5$ TFA,. 0.2 $H_2O$, 0.1 $CH_3CN$: C, 51.64; H, 4.95; N, 5.96. Found: C, 51.70; H, 5.25; N, 5.96.

EXAMPLE 3

3-[[5-(2-pyridinylamino)pentoxy]phenyl]propanoic acid

STEP 1

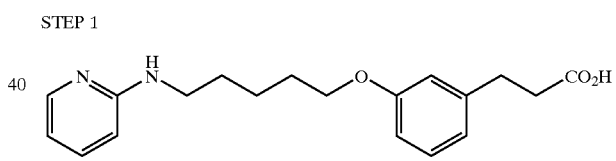

2-(5-hydroxypentylamino)pyridine N-oxide was prepared dissolving 2-chloropyridine N-oxide·HCl (18.07 mmol), 5-amino-1-pentanol (36.14 mmol), and $NaHCO_3$ (90.36 mmol) in tert-amyl alcohol (20 mL), then refluxing overnight under Ar. After cooling, the reaction was filtered and concentrated to a green oil. Purification by silica gel chromatography (eluent: 94:5:1 $CH_2Cl_2$, MeOH, $NH_4OH$) yielded a yellow solid (3.07 g). $^1$H NMR was consistent with the desired product.

Step 2

The title compound was prepared in the same manner as described in Steps 2, 3, and 4 of Example 1, substituting 2-(5-hydroxypentylamino) pyridine N-oxide for 2-(3-hydroxypropylamino)pyridine N-oxide. $^1$H NMR, MS, and analytical analysis were consistent with the proposed structure.

Elemental analysis calculated for $C_{19}H_{24}N_2O_3 \cdot 1.1$ TFA, .0.4 $H_2O$: C, 55.23; H, 5.66; N, 6.08. Found: C, 55.29; H, 5.62; N, 6.08.

EXAMPLE 4

3-Phenyl-4-[3-[3-(pyridin-2-yl)amino-1-propyloxy]phenyl] butanoic acid

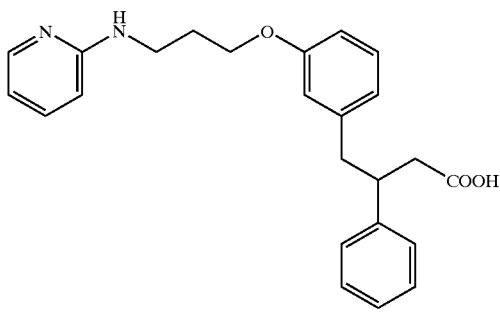

STEP 1

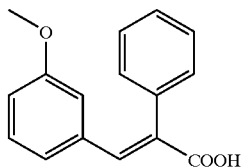

2-Phenyl-m-methoxycinnamic acid

A mixture of m-anisaldehyde (29.37 g, 21.57 mmol) and phenylacetic acid (29.37 g, 21.57 mmol) in acetic anhydride (200 mL) was stirred with triethylamine (30 mL). The reaction mixture was heated at reflux for 4 hours, then cooled to 80–90° C., then water (500 mL) was added slowly. An oil separated, which upon stirring and cooling produced a light orange solid. The solid was filtered, washed with water and dried to afford the desired product (35 g, 64% yield). NMR was consistent with the structure.

STEP 2

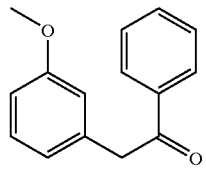

Triethylamine (17 mL) was added to a mixture of 2-phenyl-m-methoxycinnamic acid (30.0 g, 118.0 mmol) and diphenylphosphorylazide (28 mL) in toluene (200 mL) at 0° C. After the reaction had been complete (3 hours), the reaction mixture was quenched with concentrated HCl (20 mL) and extracted with ether (200 mL). The organic layer was concentrated and the residue was stirred further with concentrated HCl (100 mL) and dioxane (100 mL) for 24 hours. The reaction mixture was diluted with water (400 mL) and was extracted with ether (3×300 mL). The ether layer was dried and concentrated to afford the desired product (10 g, 38% yield). $^1$H NMR was consistent with the structure.

STEP 3

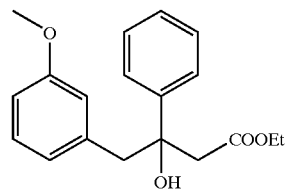

Ethyl 4-(m-methoxyphenyl)-3-phenyl-3-hydroxybutyrate

Lithium hexamethyldisilazane (88.5 mL, 88.5 mmol) was added to THF (150 mL) at –78° C. After 15 minutes, ethyl acetate (7.79 g, 88.5 mmol) was added over 10 minutes and stirred at –78° C. for 30 minutes. The m-methoxybenzyl phenyl ketone in (10.0 g, 44.25 mmol) THF (100 mL) was added over 15 minutes and kept at that temperature for 3 hours. The reaction mixture was quenched at that temperature with saturated ammonium chloride (15 mL). The reaction mixture was diluted with ether (200 mL) and the organic layer was washed with brine, (100 mL), dried and concentrated to afford the desired product (12 g, 86% yield). NMR was consistent with the desired structure.

STEP 4

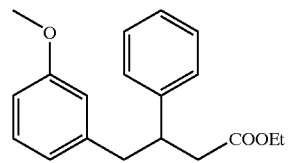

Ethyl 4-(m-methoxyphenyl)-3-phenyl butyrate

A mixture of ethyl 4-(m-methoxyphenyl)-3-phenyl-3-hydroxybutyrate (4.39 g, 13.98 mmol), palladium/carbon (10%, 2.5 g) hydrochloric acid (1.2 mL) in acetic acid (150 mL) was subjected to hydrogenation (50 psi) for 24 hours. The catalyst was filtered, and the filtrate was concentrated to afford the desired product (1.89 g; 45% yield). $^1$H NMR was consistent with the desired product.

STEP 5

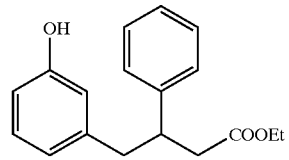

Ethyl 4-(m-hydroxyphenyl)-3-phenylbutyrate

Aluminum chloride (4.1 g. 30.75 mmol) was added to a cooled solution of ethyl 4-(m-methoxyphenyl)-3-phenylbutyrate(1.83 g, 6.14 mmol) and ethyl mercaptan (2.3 mL) in dichloromethane (50 mL) at 0° C. After stirring for 3 hours at room temperature. The reaction mixture was cooled to 0° C., and was slowly quenched with hydrochloric acid (3N, 50 mL). The organic layer was separated, washed with brine, dried and was concentrated. The residue was chromatographed (hexane: ethyl acetate, 3:1) to afford the desired product as an oil (1.56 g; 90% yield). $^1$H NMR was consistent with the desired product.

Step 6

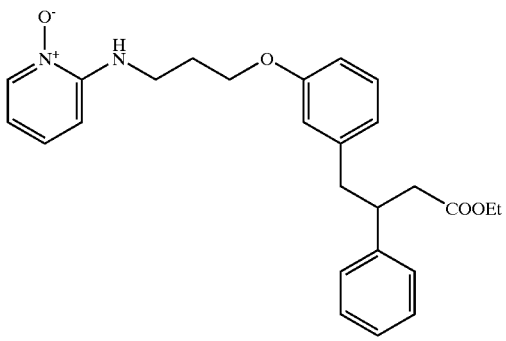

Ethyl 3-phenyl-4-[3-{3-(1-oxopyridin-2-yl)amino-1-propyloxy}phenyl]-butanoate

A solution of DEAD (1.91 g) and N-(2-pyridyl-N-oxide)-3-aminopropanol (1.84 g,) in DMF (10 mL) was added to a solution of ethyl 4-(m-hydroxy-phenyl)-3-phenylbutyrate (1.56 g, 5.49 mmol) and triphenyl-phosphine (2.876 g) in DMF (15 mL) over a period of 5 minutes. The reaction mixture was stirred for 24 hours. DMF was removed in vacuo and the residue was purified by hplc (reverse phase C18, 10%–100% gradient of acetonitrile in water containing 0.05% TFA) to afford the desired product as an oil (1.40 g, 59% yield). $^1$H NMR was consistent with the desired product.

STEP 7

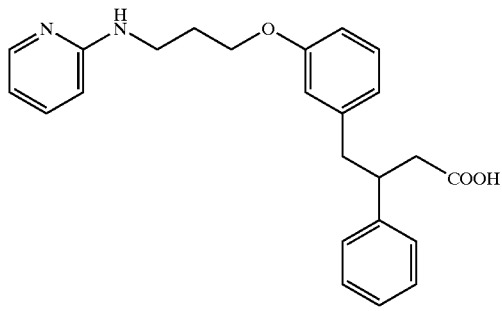

3-Phenyl-4-[3-[3-(pyridin-2-yl)amino-1-propyloxy]phenyl]butanoic acid

A mixture of ethyl 3-phenyl-4-[3-[3-(1-oxopyridin-2-yl)amino-1-propyloxy]-phenyl]butanoate (1.30 g, 2.98 mmol), palladium/C (0.30 g), cyclohexene (2.5 mL) in ethanol (25 mL) was heated at reflux over 24 hours. The reaction mixture was filtered, and the residue was washed with an additional amount of ethanol (100 mL). The combined filtrates were concentrated. The residue was added to ethanol (5 mL) and sodium hydroxide (5 mL, 2.5 N) and stirred for 8 hours. The reaction mixture was concentrated and the residue was dissolved in water (5 mL) and the pH was adjusted to 2 by the addition of TFA. This was purified by hplc (reverse phase C18, 10%–100% gradient of acetonitrile in water containing 0.05% TFA). The desired product was obtained as its HCl (after treatment with diluted HCl) salt (0.90 g, 71% yield). $^1$H NMR and mass spectra were consistent with the desired product.

EXAMPLE 5

3-[3-(2-pyridinylamino)propoxy]phenyl-3-methylbutanoic acid

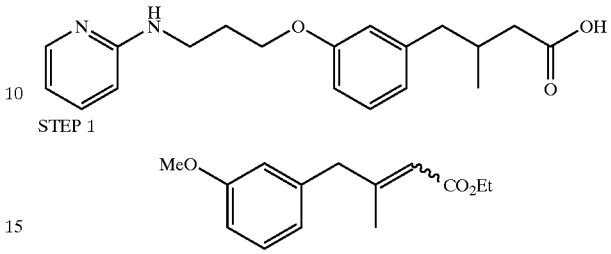

STEP 1

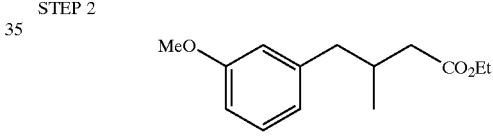

To a suspension of sodium hydride (505 mg, 21.0 mmol) in dry THF (50 mL) at 0° C. was added triethyl phophonoacetate (4.7 g, 21.0 mmol) in THF (5 mL). The reaction mixture was stirred at 0° C. for 30 minutes. To this solution was added a solution of 3-methoxyphenylacetone (3.0 g, 18.3 mmol) in THF (5 mL). The reaction was stirred at 0° C. for 30 minutes and then at ambient temperature for 17 hours. The reaction mixture was partitioned between 1M aqueous HCl and ether. The aqueous solution was extracted with ether. The combined organic solution was washed with brine, dried (Na$_2$SO$_4$) and concentrated in vacuo. The residue was purified by chromatography (9:1 hexane:ethyl acetate) to give the desired product, (2.6 g, 53% yield).

STEP 2

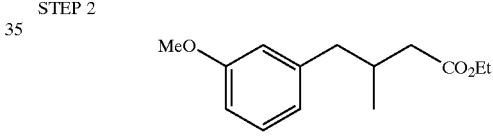

The product from Step 1(2.6 g, 11.1 mmol) and 5% Pd/C in ethanol at ambient temperature and 60 psi was hydrogenated for 1 hour. The catalyst was removed by filtration and the reaction solution was concentrated in vacuo to give the desired product, (2.4 g, 92% yield).

STEP 3

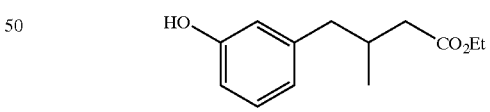

To a solution of the product from Step 2(2.4 g, 10.2 mmol) in CH$_2$Cl$_2$ at −10° C. was added boron tribromide (20.4 mL of a 1M solution in CH$_2$Cl$_2$). The reaction mixture was warmed to 10° C. over 1 hour. Ethanol (10 mL) was added and the mixture stirred for 1 hour. The mixture was concentrated in vacuo, dissolved in ethyl acetate and washed with 10% aqueous sodium bicarbonate solution. The aqueous solution was extracted with ethyl acetate. The combined organic solution was dried (Na$_2$SO$_4$) and concentrated. The residue was purified by chromatography (5:1 hexane:ethyl acetate) to give the desired product, (1.5 g, 66% yield).

STEP 4

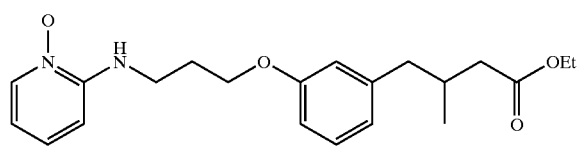

To a solution of the product from Step 3 (750 mg, 3.37 mmol) in DMF (9 mL) was added triphenylphosphine (885 mg, 3.37 mmol). The reaction solution was kept at ambient temperature for 30 minutes. To this solution was added a solution of 2-(3-hydroxypropylamino)pyridine N-oxide (567 mg, 3.37 mmol) and diethyl azodicarboxylate (0.53 mL, 3.37 mmol) in DMF (5 mL). The reaction solution was kept at room temperature for 17 hours and concentrated in vacuo. The residue was dissolved in ethyl acetate and washed with water. The aqueous solution was back extracted with ethyl acetate. The combined organic solution was washed with brine, dried ($Na_2SO_4$) and concentrated in vacuo. The residue was purified by chromatography (99.5:0.25:0.25 $CH_2Cl_2$:MeOH:$NH_4OH$) to give the desired product, (350 mg, 28% yield).

STEP 5

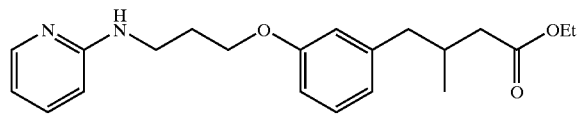

To a solution of the product from Step 4 (350 mg, 0.94 mmol) in isopropanol (12 mL) was added cyclohexene (0.95 mL, 9.4 mmol) and 10% Pd/C (10 mg). The reaction mixture was heated at reflux for 18 hours. Additional cyclohexene (0.95 mL) and Pd/C (10 mg) were added and the mixture heated at reflux for 8 hours. This addition and heating were repeated two more times to consume all the starting material. The mixture was cooled, filtered through a pad of Celite and the Celite pad washed with isopropanol. The organic solution was concentrated in vacuo to give the desired product, (330 mg, 99% yield).

STEP 6

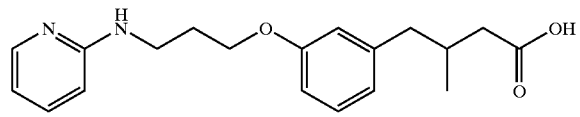

3-[3-(2-pyridinylamino)propoxy]phenyl-3-methylbutanoic acid

To a mixture of the product from Step 5 (330 mg, 0.92 mmol) in 1M aqueous NaOH solution (5 mL) was added methanol (3 mL) and THF (3 mL). The reaction solution was kept at room temperature for 4 hours. Volatiles were removed in vacuo and the aqueous solution was acidified to pH 3 with TFA. The aqueous solution was purified by RP HPLC (starting gradient 80:20 H2O/TFA:MeCN, retention time 14 minutes) to give the desired product, (300 mg, 70% yield). Microanalytical: calcd for $C_{19}H_{24}N_2O_3$+1.2 TFA: C, 55.25; H, 5.46; N, 6.02. Found: C, 55.29; H, 5.75; N, 6.24.

EXAMPLE 6

3-[4-(2-pyridinylamino)butoxy]phenyl-3-methylbutanoic acid

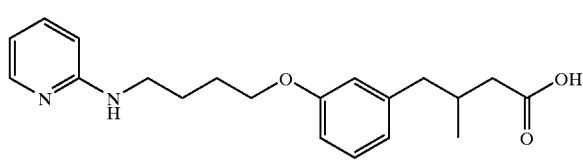

STEP 1

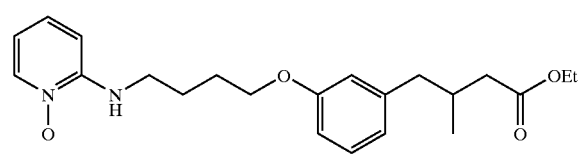

To a solution of the product from Example 5, Step 3 (720 mg, 3.24 mmol) in DMF (9 mL) was added triphenylphosphine (850 mg, 3.24 mmol). The reaction solution was kept at ambient temperature for 1 hour and a solution of 2-(4-hydroxybutylamino)pyridine N-oxide (590 mg, 3.24 mmol) and diethyl azodicarboxylate (0.51 mL, 3.24 mmol) in DMF (5 mL) was added. The reaction solution was kept at room temperature for 18 hours and concentrated in vacuo. The residue was dissolved in ethyl acetate and washed with water. The aqueous solution was back extracted with ethyl acetate. The combined organic solution was washed with brine, dried ($Na_2SO_4$) and concentrated in vacuo. The residue was purified by chromatography (98:1:1 $CH_2Cl_2$:MeOH:$NH_4OH$) to give the desired product, (560 mg, 45% yield).

STEP 2

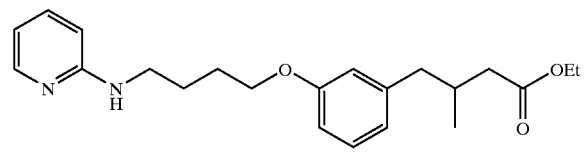

To a solution of the product from Step 1 (560 mg 1.45 mmol) in isopropanol (16 mL) was added cyclohexene (1.5 mL, 14.5 mmol) and 10% Pd/C (15 mg). The reaction mixture was heated at reflux for 18 hours. Additional cyclohexene (1.5 mL) and Pd/C (15 mg) were added and the mixture heated at reflux for 8 hours. This addition and heating were repeated two more times to consume all the starting material. The mixture was cooled, filtered through a pad of Celite and the Celite pad washed with isopropanol. The organic solution was concentrated in vacuo to give the desired product, (515 mg, 96% yield).

STEP 3

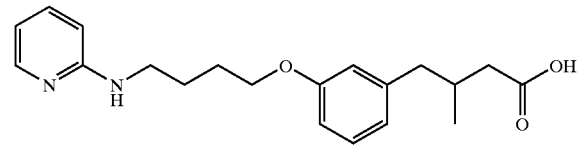

3-[4-(2-pyridinylamino)butoxy]phenyl-3-methylbutanoic acid

To a mixture of the product from Step 2 (500 mg, 1.35 mmol) in 1 M aqueous NaOH solution (7 mL) was added methanol (4 mL) and THF (4 mL). The reaction solution was kept at room temperature for 5 hours. Volatiles were removed in vacuo and the aqueous solution was acidified to pH 4 with TFA. The aqueous solution was purified by RP HPLC (starting gradient 80:20 H2O/TFA:MeCN, retention time 15 min) to give the desired product, (385mg, 57% yield). Microanalytical: calcd for $C_{20}H_{26}N_2O_3 \cdot 1.4$ TFA: C, 54.54; H, 5.50; N. 5.58. Found: C, 54.53; H, 5.85; N, 5.67.

EXAMPLE 7

β-[[[3-[3-(2-pyridinylamino)propoxy]phenyl]sulfonyl]amino]benzenpropanoic acid

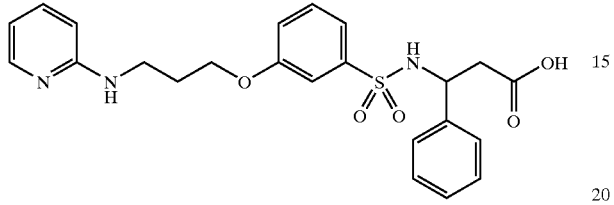

STEP 1

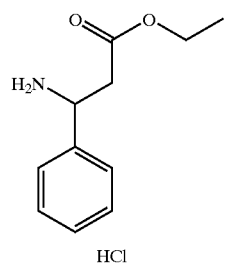

HCl

Ethyl β-aminobenzenepropanoate, monohydrochloride

DL-3-amino-3-phenylpropionic acid (5.4 g, 0.032 moles) was added to saturated HCl (100 ml) in ethanol. The reaction mixture was stirred for 4 hours at room temperature under nitrogen. HCl in ethanol was removed under vacuum to afford a residue. The concentrated residue was triturated with ethyl acetate. The ethyl acetate was then removed in vacuum and the procedure was repeated twice. The resulting residue was dried under high vacuum to give a yellow solid (7.4 g, 98.6% yield). $^1$H NMR (400 MHz, CD$_3$OD) δ 7.46–7.41 (m, 5H), 4.70 (m, 1H), 4.16–4.11 (m, 2H), 3.11–2.96 (m, 2H), 1.19 (t, 3H, 7.18 Hz). HRMS (M+H) calculated for $C_{11}H_{15}N_1O_2$ 194.1176, found 194.1210.

STEP 2

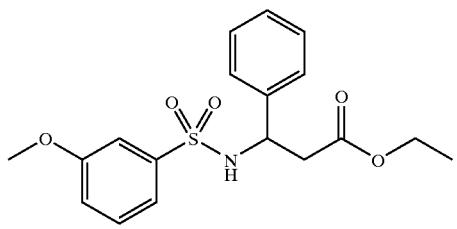

ethyl β-[[(3-methoxypheyl)sulfonyl]amino]benzenepropanoate

3-Methoxybenzenesulfonyl chloride (3.03 g, 14.7 mmol) and the product of Step 1 (3.37 g, 14.7 mmol) were dissolved in DMF (50 ml). Triethylamine (2.97 g, 29 mmol) was added to the solution at room temperature. The reaction mixture was stirred for 18 hours at room temperature. A solid formed which was filtered and washed with DMF. The filtrate was concentrated. The concentrated residue was purified by flash chromatography (silica gel, 60% ethyl acetate/hexane) to give a solid (4.12 g, 77.3% yield). $^1$H NMR (400 MHz, CD$_3$OD) δ 7.26–7.20 (m, 2H), 7.12–7.06 (m, 5H), 6.98–6.95 (m, 1H), 4.79–4.73 (m, 1H), 4.01–3.95 (m, 2H), 3.71 (s, 3H), 2.78–2.64 (m, 2H), 1.12 (t, 3H, J=7.05 Hz). HRMS (M+H) calculated for $C_{18}H_{21}N_1O_5S_1$ 364.1213, found 364.1201.

STEP 3

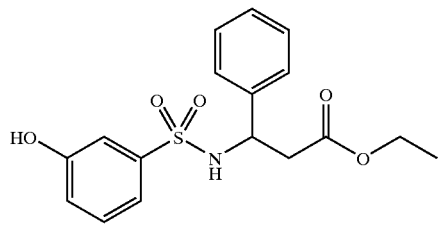

β-[[(3-(hydroxypheyl)sulfonyl]amino]benzenepropanoate

A mixture of the product of Step 2 (4 g, 11 mmol) and ethanethiol (3.4 g, 55 mmol) in methylene chloride (100 ml) was cooled in ice-bath. Aluminum chloride (7.3 g, 55 mmol) was added. The reaction mixture was stirred at room temperature for 4 hours. The reaction mixture was quenched with 3N HCl (100 ml). The organic layer was separated. The aqueous layer was extracted with methylene chloride (2×100 ml). The combined organic extracts were concentrated and dried to give a white solid (3.3 g, 85.9% yield). The material was used in the next reaction without further purification. $^1$H NMR (400 MHz, CD$_3$OD) δ 7.16–7.04 (m, 8H), 6.84–6.82 (m, 1H), 4.72 (t, 1H, J=7.56 Hz), 4.01–3.94 (m, 2H), 2.77–2.63 (m, 2H), 1.11 (t, 3H, J=7.18 Hz). Mass spectrometry: 350.1 (M+H)$^+$.

STEP 4

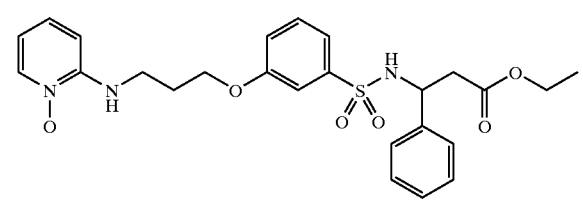

ethyl β-[[[3-(3-[(1-oxido-2-pyridinyl)amino]propoxy]phenyl]sulfonyl]amino]benzenepropanoate, mono (trifluoroacetate)

The product produced in Step 3 (1 g, 2.86 mmol) and triphenylphosphine (1.5 g, 5.73 mmol) were dissolved in DMF (10 ml). 2-[(3-Hydroxy-1-propyl)amino]pyridine-N-oxide (0.97 g, 5.73 mmol) and diethyl azodicarboxylate (1 g, 5.73 mmol) were dissolved in DMF then added to above solution at room temperature. The reaction mixture was stirred 18 hours at room temperature. The solvent was removed. The crude reaction mixture was purified by reversed phase HPLG. Appropriate fractions were collected to give a brown color oil (1.97 g) which contain the desired compound. Mass spectrometry: 500.4 (M+H)$^+$.

STEP 5

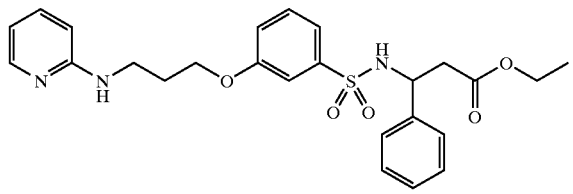

ethyl β-[[[3-(3-[(2-pyridinylamino)propoxy]phenyl] sulfonyl]amino]benzenepropanoate, mono(trifluoroacetate): 5% Pd/C (0.4g) was added to a solution of the product produced in Step 4 (0.42 g, 0.68 mmol) and cyclohexene (2 ml) in absolute EtOH (12 mL). The mixture was heated to reflux. After 16 hours, the reaction mixture was filtered through celite and the filtrate was concentrated. The concentrated residue was purified by reverse phase HPLC to give a yellow oil (50mg, 12.5% yield). $^1$H NMR (400 MHz, CD$_3$OD) δ 8.33 (d, 1H, J=8.72 Hz), 7.84–7.79 (m, 2H), 7.23–6.92 (m, 10H), 6.77 (t, 1H, J=6.28 Hz), 4.61 (m, 1H), 3.95 (t, 2H, J=6.02 Hz), 3.88–3.83 (m, 2H), 3.46–3.36 (m, 3H), 2.66—2.54 (m, 2H), 2.00 (t, 2H, J=6.28 Hz), 100 (t, 3H, J=7.05 Hz). HRMS (M+H) calculated for C$_{25}$H$_{29}$N$_3$O$_5$S$_1$ 484.1906, found 484.1922.

STEP 6

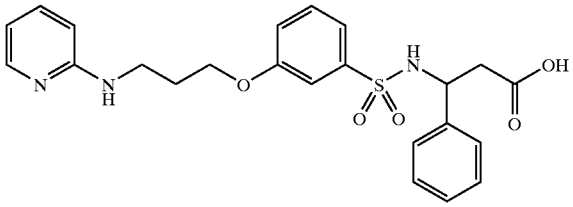

β-[[[3-[3-[(2-pyridinylamino)propoxy]phenyl]sulfonyl] amino]benzene-propanoic acid, mono(trifluoroacetate)

Lithium hydroxide (15 mg, 0.38 mol) was added to the product of Step 5 in 1:1/acetonitrile:water (4 ml). The reaction mixture was stirred several hours at room temperature then purified by 18C reverse phase HPLC to give the desired compound (40mg, 55.5% yield). $^1$H NMR (400 MHz, CD$_3$OD) δ 7.90–7.85 (m, 1H), 7.79 (d, 1H), 7.29–7.23 (m, 2H), 7.10–6.98 (m 8H), 6.86 (t, 1H, J=6.79 Hz), 4.74 (t, 1H, J=7.43 Hz), 4.05 (t, 2H, J=5.90 Hz), 3.55 (t, 2H, J=6.79 Hz), 2.76–2.63 (m, 2H), 2.19–2.13 (m, 2H). HRMS (M+H) calculated for C$_{23}$H$_{25}$N$_3$O$_5$S$_1$ 456.1593, found 456.1581.

EXAMPLE 8

β-[[[3-[4-(2-pyridinylamino)butoxy]phenyl]sulfonyl] amino]benzene propanoic acid

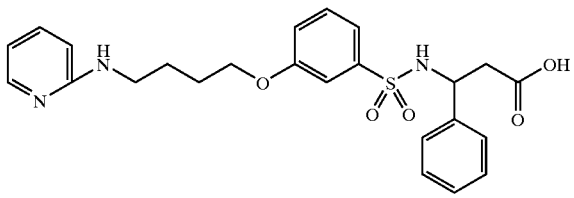

The product produced in Step 3 of Example 7 (0.2 g, 0.55 mmol) and triphenylphosphine (0.15 g, 0.55 mmol) were dissolved in DMF (5 ml). 2-[(4-Hydroxy-1-butyl)amino] pyridine-N-oxide (0.1 g, 0.55 mmol) was added to above solution neat then followed by adding diethylazodicarboxylate (0.1 g, 0.55 mmol) at room temperature. The reaction mixture was stirred at room temperature for 3 hours. The reaction mixture was purified by reversed phase HPLC. The appropriate fractions were collected to give an oil (0.3 g) which contained the desired compound (M+H: 514.3). The oil was dissolved in 5 ml ethanol and then 5% Pd/C (0.3 g) and cyclohexene (2 ml) were added. The reaction mixture was heated at 70° C. for 18 hours. The Pd/C was filtered through celite and the filtrate was concentrated under reduced vacuum. The concentrated residue was dissolved in 1:1/acetonitrile water (2 ml) with lithium hydroxide (50 mg). The reaction mixture was stirred at room temperature for 3 hours. The reaction mixture was acidified by adding TFA and then purified by reversed phase HPLC to give a white solid (20 mg, 6.2% yield). M+H: 470.05. NMR (400 MHz, CD$_3$OD) δ 1.11 (t, 2 H, J=7.18 Hz), 1.83 ((m, 4 H), 2.64–2.77 (m, 2 H), 3.48 (t, 2H, J=6.53 Hz), 3.92–4.01 (m, 4 H), 4.75 (t, 1 H, J=7.56 Hz), 6.79–6.83 (m, 1 H), 6.95–6.98 (m, 1H), 7.05–7.16 (m, 7 H), 7.21–7.27 (m, 2 H), 7.70–7.74 (m, 1 H), 8.15–8.17 (m, 1 H).

EXAMPLE 9

3-[3-(2-pyridinyl)amino]-1-propyloxyphenylsulfonyl)-3-(3-pyridyl)aminopropanoic acid

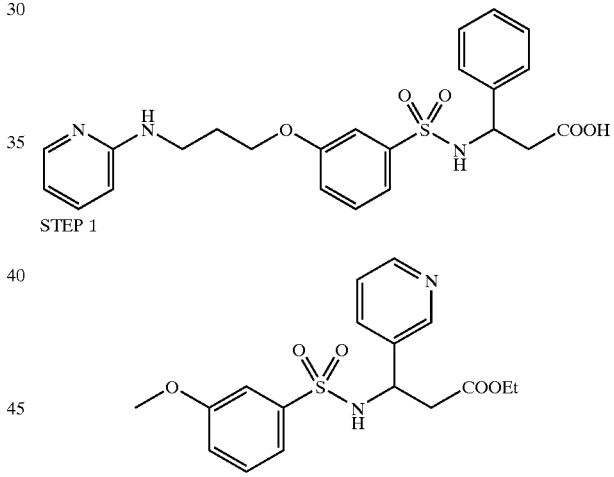

STEP 1

Ethyl 3-N-(3-metoxyphenylsulfonyl)-3-(3-pyridyl) aminopropionate

Triethylamine (6.8 mL) was added to a solution of m-methoxybenzenesulfonyl chloride (10.0 g, 48.40 mmol) and ethyl 3-amino-3-(3-pyridyl)propionate (12.91 g, 48.40 mmol) in dimethylacetamide (600 mL) and the reaction mixture was stirred for 18 h at rt. The solvent was removed in vacuo. The residue was partitioned between ethyl acetate (500 mL) and sodium bicarbonate (saturated, 400 mL). The organic layer was washed with brine (400 mL) and dried (MgSO4) and was concentrated to afford 9.67 g (55%) of the desired product. $^1$H NMR (CDCl$_3$) δ 9.01 (s, 1H), 8.63 (d, 1H, J=5.5 Hz), 8.31 (d, 1H, J=7.8 Hz), 8.00 (d, 1H, J=8.6 Hz), 7.62 (m, 1H), 7.48 (m, 1H), 7.2–7.33 (m, 2H), 6.95–6.97 (m, 1H), 4.91 (m, 1H), 3.75–3.94 (m, 2H), 3.76 (s, 3H), 2.95 (m, 2H), 1.08 (t, 3H, J=7 Hz).

Step 2

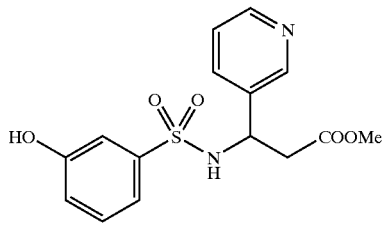

Methyl 3-N-(3-hydroxyphenylsulfonyl)-3-(3-pyridyl)aminopropionate

Boron tribromide (13.22 g, 5 mL, 52.72 mmol) was added to a solution of ethyl 3-N-(3-metoxyphenylsulfonyl)-3-(3-pyridyl)aminopropionate (9.60 g, 26.36 mmol) in dichloromethane (100 mL) at rt. The reaction mixture was stirred for 18 h and was quenched with methanol and was concentrated. The residue was dissolved in ethyl acetate (200 mL) and was washed with sodium bicarbonate (200 mL), dried and was concentrated to afford 7 g (80%) of the desired product. $^1$H NMR (CD$_3$OD) δ 8.29 (m, 2H), 7.57 (d, 1H, J=7.9 Hz), 7.11–7.16 (m, 3H), 6.99 (m, 1H), 6.85 (m, 1H), 4.74 (m, 1H), 3.53 (s, 3H), 2.74 (m, 2H). Anal Calcd for C$_{15}$H$_{16}$N$_2$O$_5$S: Mol. Wt. 337.0858 (M+H). Found: Mol. Wt, 337.0852 (M+H, HRFABMS).

STEP 3

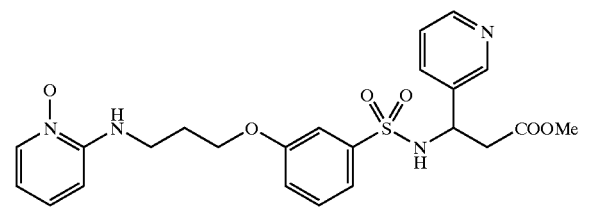

Methyl 3-N-[3-(2-N-oxypyridyl)amino]-1-propyloxyphenylsulfonyl)-3-(3-pyridyl)aminopropionate A solution of DEAD (1.03 g, 5.95 mmol) and N-(2-pyridyl-N-oxide)-3-aminopropanol (1.0 g, 5.95) in DMF (10 mL) was added to a solution of methyl 3-N-(3-hydroxyphenylsulfonyl)-3-(3-pyridyl)amino-propionate (1.0 g, 2.975 mmol) and triphenylphosphine (1.64 g, 6.26 mmol) in DMF (10 mL) over a period of 1 min (mildly exothermic reaction) and the reaction mixture was stirred for 24 h. DMF was removed in vacuo and the residue was purified by hplc (reverse phase C18, 10%–100% gradient of acetonitrile in water containing 0.05% TFA) to afford 0.77 g of the desired product as its TFA salt as oil. 1H NMR is consistent with the desired product. $^1$H NMR (CD$_3$OD) δ 8.52–8.58 (m, 2H), 8.14–8.17 (m, 2H), 7.62–7.66 (m, 2H), 7.1–7.4 (m, 5H), 6.77–6.81 (m, 1H), 4.92 (m, 1H), 4.10 (m, 2H), 3.61–3.80 (m, 2H), 3.53 (s, 3H), 2.83 (m, 2H), 2.16 (m, 2H).

STEP 4

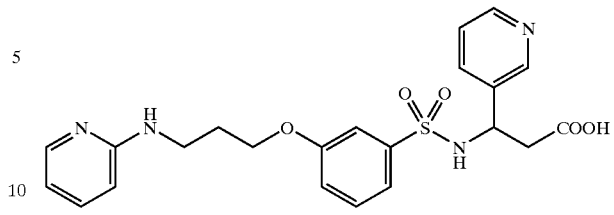

3-[3-(2-pyridinyl)amino]-1-propyloxyphenylsulfonyl)-3-(3-pyridyl)aminopropionic acid A mixture of methyl 3-[3-(2-N-oxypyridyl)amino]-1-propyloxyphenyl-3-(3-pyridyl)propionate(0.77 g), palladium/C (0.5 g), cyclohexene (2 mL) in ethyl alcohol (25 mL) was heated at reflux over 24 h. The reaction mixture was filtered, and the residue was washed with additional amount of ethyl alcohol (10 mL). The combined filtrates were concentrated. The residue was added ethanol (10 mL) and water (5 mL) and lithium hydroxide was added till the solution was slightly basic (pH 11) and stirred for 8 h. The reaction mixture was concentrated and the residue was dissolved in water (5 mL) and the pH was adjusted to 2 by the addition of TFA. This was purified by hplc (reverse phase C18, 10%–100% gradient of acetonitrile in water containing 0.05% TFA) and the pure fractions were combined and lyophilized to afford 0.50 g of the desired product as its TFA salt. 1H NMR and mass spectra are consistent with the desired product. $^1$H NMR (CD$_3$OD) δ 8.68 (s, 1H), 8.60 (d, 1 H, J=5.1 Hz), 8.31 (d, 1H, J=7.8 Hz), 7.75–7.89 (m, 3H), 7.05–7.37 (m, 5H), 6.86 (t, 1H, J=6.6 Hz), 4.91 (m, 1H), 4.13 (m, 2H), 3.58 (m, 2H), 2.82 (m, 2H), 2.18 (m, 2H).

EXAMPLE 10

3-[4-(2-pyridinyl)amino]-1-butyloxyphenylsulfonyl)-3-(3-pyridyl)aminopropionic acid

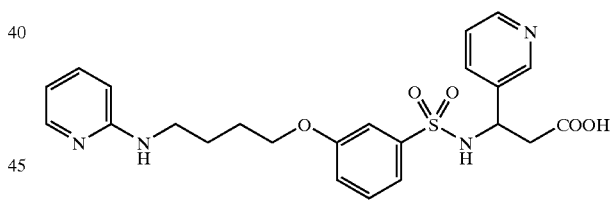

STEP 1

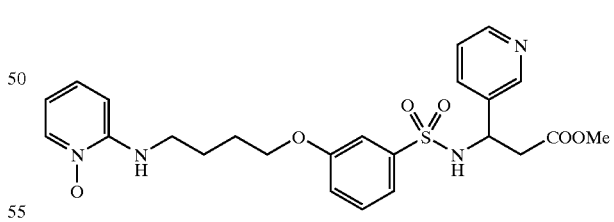

Methyl 3-N-[4-(2-N-oxypyridyl)amino]-1-butyloxyphenylsulfonyl)-3-(3-pyridyl)aminopropionate A solution of DEAD (1.54 g, 8.92 mmol) and N-(2-pyridyl-N-oxide)-3-aminobutanol (1.62 g, 8.92 mmol) in DMF (10 mL) was added to a solution of methyl 3-N-(3-hydroxyphenylsulfonyl)-3-(3-pyridyl)aminopropionate (1.5 g, 4.46 mmol) and triphenylphosphine (2.46 g, 9.38 mmol) in DMF (10 mL) over a period of 1 min (mildly exothermic reaction) and the reaction mixture was stirred for 24 h. DMF was removed in vacuo and the residue was purified by hplc (reverse phase C18, 10%–100% gradient of acetonitrile in water containing 0.05% TFA) to afford 0.55 g of the desired product as its TFA salt as an oil. $^1$H NMR (CD$_3$OD) δ 8.72 (s, 1H), 8.64 (d, 1H, J=5.5 Hz), 8.39 (d, 1H, J=8.2 Hz), 8.18 (d, 1H, J=6.6 Hz), 7.75–7.84 (m, 2H), 7.04–7.35 (m, 5H), 6.82 (t, 1H, J=7.0 Hz), 4.98 (t, 1H, J=6.6 Hz), 4.02 (m, 2H), 3.51 (s, 3H), 3.48 (m, 2H), 2.86 (m, 2H), 1.86 (m, 4H).

STEP 2

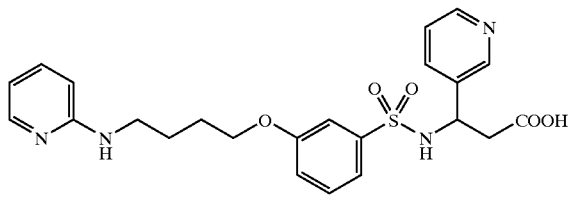

3-[4-(2-pyridinyl)amino]-1-butyloxyphenylsulfonyl)-3-(3-pyridyl)aminopropionic acid A mixture of Methyl 3-N-[4-(2-N-oxypyridyl)amino]-1-butyloxyphenyl-sulfonyl)-3-(3-pyridyl)aminopropionate (0.50 g,), palladium/C (0.5 g), cyclohexene (2 mL) in ethyl alcohol (25 mL) was heated at reflux over 24 h. The reaction mixture was filtered, and the residue was washed with additional amount of ethyl alcohol (10 mL). The combined filtrates were concentrated. The residue was added ethanol (10 mL) and water (5 mL) and lithium hydroxide was added till the solution was slightly basic (pH 11) and stirred for 8 h. The reaction mixture was concentrated and the residue was dissolved in water (5 mL) and the pH was adjusted to 2 by the addition of TFA. This was purified by hplc (reverse phase C18, 10%–100% gradient of acetonitrile in water containing 0.05% TFA) and the pure fractions were combined and lyophilized to afford 0.40 g of the desired product as its TFA salt. $^1$H NMR (CD$_3$OD) δ 8.81 (s, 1H), 8.71 (d, 1H, J=5.9 Hz), 8.57 (d, 1H, J=8.2 Hz), 7.83–7.96 (m, 3H), 7.04–7.35 (m, 5H), 6.86 (m, 1H), 4.98 (m, 1H), 4.06 (m, 2H), 3.48 (m, 2H), 2.90 (m, 2H), 1.92 (m, 4H).

EXAMPLE 11
3-(4-(2-Tetrahydropyrimidinyl)aminobutyloxyphenylsulfonyl)-3-(3-pyridyl)aminopropionic acid

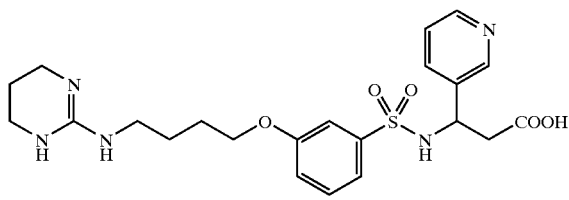

STEP 1

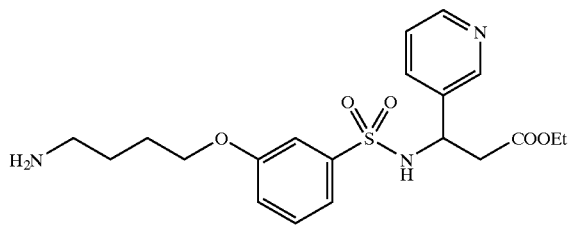

Ethyl 3-N-(4-amino-1-butyloxyphenylsulfonyl)-3-(3-pyridyl)aminopropionate

A solution of DEAD (2.92 g, 16.78 mmol) and 4-N-Boc-aminobutanol (3.36 g, 16.78 mmol) in DMF (25 mL) was added to a solution of ethyl 3-N-(3-hydroxyphenylsulfonyl)-3-(3-pyridyl)aminopropionate (2.82 g, 8.39 mmol) and triphenylphosphine (4.62 g, 8.39 mmol) in DMF (25 mL) over a period of 1 min (mildly exothermic reaction) and the reaction mixture was stirred for 24 h. DMF was removed in vacuo and the residue was treated with saturated ethanolic HCl and was stirred for 6 h amd was concentrated and the residue purified by hplc (reverse phase C18, 10%–100% gradient of acetonitrile in water containing 0.05% TFA) to afford 2.5 g (73%)of the desired product as an oil as its TFA salt. $^1$H NMR (CD$_3$OD) δ? 8.71 (s, 1H), 8.65 (d, 1H, J=5.5 Hz), 8.38 (d, 1H, J=8.6 Hz), 7.83 (m, 1H), 7.05–7.50 (m, 4H), 4.98 (m, 1H), 3.92–4.08 (m, 4H), 3.00 (m, 2H), 2.84 (m, 2H), 1.86 (m, 4H), 1.12 (m, 3H).

Step 2

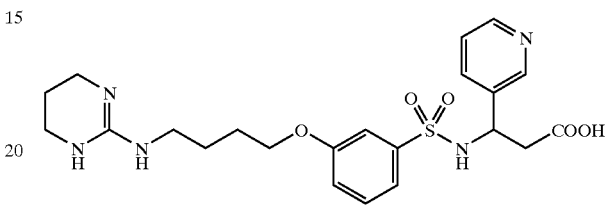

3-(4-(2-Tetrahydropyrimidinyl)aminobutyloxyphenylsulfonyl)-3-(3-pyridyl)aminopropionic acid A mixture of ethyl 3-(N-4-amino-1-butyloxyphenylsulfonyl)-3-(3-pyridyl)aminopropionate (0.50 g, 0.96 mmol), 2-thiomethyltetrahydropyrimidine hydroiodide (0.495 g, 1.93 mmol) and triethylamine (0.27 mL) in acetonitrile (10 mL) was heated at reflux for 24 h. The reaction mixture was concentrated and the residue was dissolved in water (5 mL) and the pH was adjusted to 2 by the addition of TFA. This was purified by hplc (reverse phase C18, 10%–100% gradient of acetonitrile in water containing 0.05% TFA) and the pure fractions were combined and concentrated to afford a residue. The residue was dissolved in ethanol (10 mL) and water and added lithium hydroxide to pH 11 and was stirred for 18 h. The reaction mixture was concentrated and the residue was dissolved in water (5 mL) and the pH was adjusted to 2 by the addition of TFA. This was purified by hplc (reverse phase C18, 10%–100% gradient of acetonitrile in water containing 0.05% TFA) and the pure fractions were combined and lyophilized to afford 0.110 g of the desired product as its TFA salt. $^1$H NMR (CD$_3$OD) δ 8.56–8.62 (m, 2H), 8.23 (d, 1H, J=8.0 Hz), 7.70 (m, 1H), 7.04–7.35 (m, 4H), 4.91 (m, 1H), 3.98–4.01 (m, 2H), 3.29–3.35 (m, 4H), 3.16–3.20 (m, 2H), 2.82 (m, 2H), 1.70–1.95 (m, 6H).

EXAMPLE 11
3-(4-(2-(5-hydroxy-tetrahydropyrimidinyl)aminobutyloxyphenyl-sulfonyl))-3-(3-pyridyl)aminopropionic acid

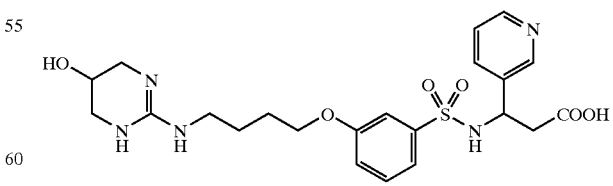

3-(4-(2-(5-hydroxy-tetrahydropyrimidinyl)aminobutyloxyphenyl-sulfonyl))-3-(3pyridyl)aminopropionic acid A mixture of ethyl 3-N-(4-amino-1-butyloxyphenylsulfonyl)-3-(3-pyridyl)aminopropionate (0.50 g, 0.96 mmol), 2-thiomethyl-5-hydroxy-tetrahydropyrimidine hydroiodide (0.495 g, 1.93 mmol) and triethylamine (0.27 mL) in acetonitrile (10 mL) was heated at reflux for 24 h. The reaction mixture was concentrated and the residue was dissolved in water (5 mL) and the pH was adjusted to 2 by the addition of TFA. This was purified by hplc (reverse phase C18, 10%–100% gradient of acetonitrile in water containing 0.05% TFA) and the pure fractions were combined and concentrated to afford a residue. The residue was dissolved in ethanol (10 mL) and water and added lithium hydroxide to pH 11 and was stirred for 18 h. The reaction mixture was concentrated and the residue was dissolved in water (5 mL) and the pH was adjusted to 2 by the addition of TFA. This was purified by hplc using reverse phase C18 column and 10%–100% gradient of acetonitrile in water containing 0.05% TFA. The pure fractions were combined and lyophilized to afford 0.110 g of the desired product as its TFA salt. $^1$H NMR (CD$_3$OD) δ 8.54–8.60 (m, 2H), 8.20 (d, 1H, J=7.8 Hz), 7.67 (m, 1H), 7.04–7.35 (m, 4H), 4.91 (m, 1H), 4.17 (m, 1H), 3.98–4.00 (m, 2H), 3.19–3.41 (m, 6H), 2.81 (m, 2H), 1.73–1.87 (m, 4H).

EXAMPLE 12

3-[4-(2-Pyridinyl)amino]-1-butyloxyphenylsulfonyl)-3-(3,5-dichlorophenyl)aminopropionic acid

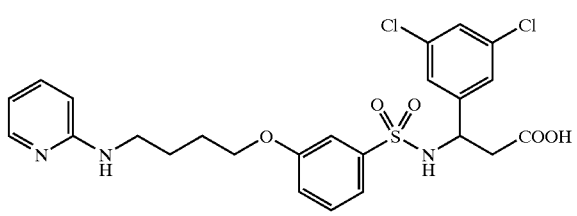

STEP 1

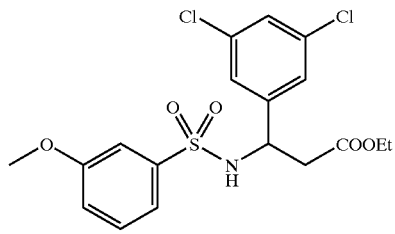

Ethyl 3-N-(3-metoxyphenylsulfonyl)-3-(3,5-dichlorophenyl)aminopropionate

Triethylamine (13.5 mL) was added to a solution of m-methoxybenzenesulfonyl chloride (10.0 g, 48.40 mmol) and ethyl 3-amino-3-(3,5-dichlorophenyl)propionate hydrochloride (14.63 g, 48.40 mmol) in dimethylacetamide (300 mL) and the reaction mixture was stirred for 18 h at room temperature. The solvent was removed in vacuo. The residue was partitioned between ethyl acetate (500 mL) and sodium bicarbonate (saturated, 400 mL). The organic layer was washed with brine (400 mL) and dried (MgSO4) and was concentrated to afford 16.8 g (80%) of the desired product. 1H NMR is consistent with the desired product. $^1$H NMR (CD$_3$OD) δ 6.93–7.41 (m, 7H), 4.72 (m, 1H), 4.03 (m, 2H), 3.74 (s, 3H), 2.65 (m, 2H), 1.15 (m, 3H).

Step 2

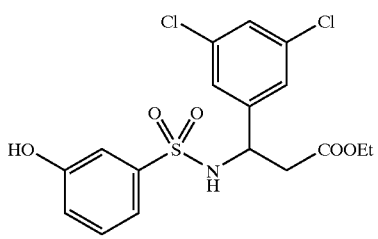

Ethyl 3-N-(3-hydroxyphenylsulfonyl)-3-(3,5-dichlorophenyl)aminopropionate

Boron tribromide (13.22 g, 5 mL, 52.72 mmol) was added to a solution of ethyl 3-N-(3-metoxyphenylsulfonyl)-3-(3,5-dichlorophenyl)aminopropionate (13.6 g, 31.18 mmol) in dichloromethane (200 mL) at rt. The reaction mixture was stirred for 18 h and was quenched with ethanol and was concentrated. The residue was dissolved in ethyl acetate (200 mL) and was washed with sodium bicarbonate (200 mL), dried and was concentrated to afford 11.8 g (90%) of the desired product. $^1$H NMR (CD$_3$OD) δ 6.83–7.36 (m, 7H), 4.71 (m, 1H), 4.0 (m, 2H), 2.68 (m, 2H), 1.14 (m, 3H).

STEP 3

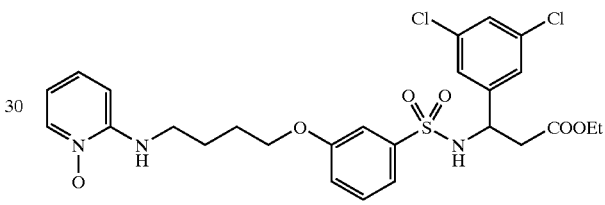

Ethyl 3-N-[4-(2-N-oxypyridyl)amino]-1-butyloxyphenylsulfonyl)-3-(3,5-dichlorophenyl) aminopropionate A solution of DEAD (1.65 g, 9.48 mmol) and N-(2-pyridyl-N-oxide)-3-aminobutanol (1.72 g, 9.48 mmol) in DMF (15 mL) was added to a solution of methyl 3-N-(3-hydroxyphenylsulfonyl)-3-(3,5-dichlorophenyl) aminopropionate (2.0 g, 4.74 mmol) and triphenylphosphine (2.61 g, 9.954 mmol) in DMF (10 mL) over a period of 1 min (mildly exothermic reaction) and the reaction mixture was stirred for 24 h. DMF was removed in vacuo and the residue was purified by hplc (reverse phase C18, 10%–100% gradient of acetonitrile in water containing 0.05% TFA) to afford 0.9 g (33%) of the desired product as its TFA salt as solid. $^1$H NMR (CD$_3$OD) δ 8.16 (d, 1H, J=6.6 Hz), 7.74 (m, 1H), 6.8–7.32 (m, 9H), 4.73 (m, 1H), 3.9–4.1 (m, 4H), 3.5 (m, 2H), 2.68 (m, 2H), 1.87–1.88 (m, 4H), 1.15 (m, 3H).

STEP 4

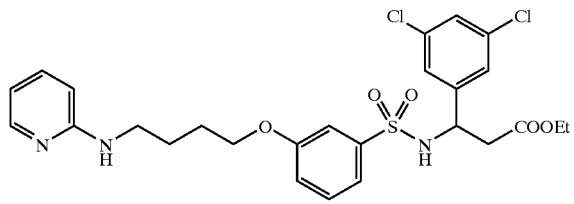

Ethyl 3-N-[4-(2-N-pyridyl)amino]-1-butyloxyphenylsulfonyl)-3-(3,5-dichlorophenyl) aminopropionate A mixture of ethyl 3-N-[4-(2-N-oxypyridyl)amino]-1-butyloxyphenylsulfonyl)-3-(3,5-dichlorophenyl)

aminopropionate (0.580 g, 0.99 mmol), triphenylphosphine (0.260 g, 0.99 mmol) and iron powder (0.083 g, 1.5 mmol) in acetic acid was heated at reflux for 1 h. The reaction mixture was concentrated and was purified by hplc to afford 0.35 g (62%) of the desired product. $^1$H NMR (CD$_3$OD) δ 7.79–7.89 (m, 2H), 6.85–7.30 (m, 9H), 4.73 (m, 1H), 3.96–4.1 (m, 4H), 3.42 (m, 2H), 2.68 (m, 2H), 1.90–1.92 (m, 4H), 1.15 (m, 3H).

STEP 5

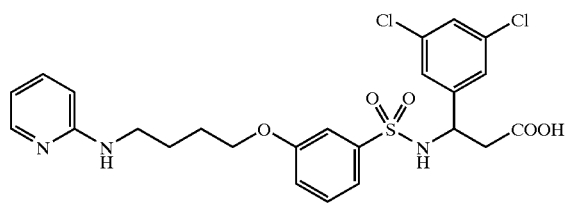

3-[4-(2-Pyridinyl)amino]-1-butyloxyphenylsulfonyl)-3-(3,5-dichlorophenyl)aminopropionic acid A solution of ethyl 3-N-[4-(2-N-pyridyl)amino]-1-butyloxyphenylsulfonyl)-3-(3,5-dichlorophenyl)aminopropionate (0.35 g) in ethanol/water (12 mL) was added lithium hydroxide (0.050 g) and after the reaction has been completed, the reaction mixture was concentrated and the residue was purified by hplc to afford 0.265 g of the desired product as solid. $^1$H NMR (CD$_3$OD) δ 7.79–7.89 (m, 2H), 6.84–7.30 (m, 9H), 4.71 (m, 1H), 3.96–4.1 (m, 2H), 3.42 (m, 2H), 2.71 (m, 2H), 1.89 (m, 4H). Anal. Calcd for $C_{24}H_{25}N_3SO_5Cl_2$: Mol. Wt, 538.0970(M+H). Found: Mol. Wt, 538.0971 (M+H, HRFABMS).

EXAMPLE 13

3-[4-(2-pyridinyl)amino]-1-butyloxyphenylsulfonyl)-3-(3-pyridyl)aminopropionic acid

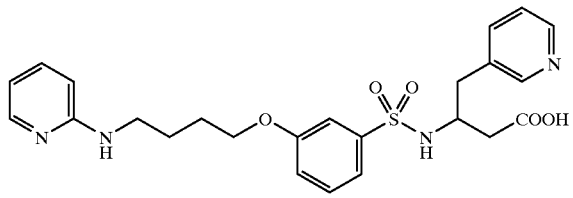

STEP 1

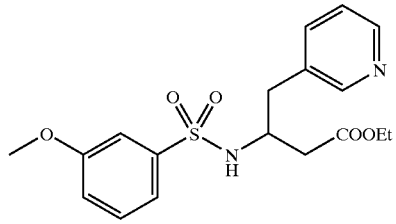

Ethyl 3-N-(3-methoxyphenylsulfonyl)-4-(3-pyridyl)aminobutanoate

Triethylamine (3.19 mL) was added to a solution of m-methoxybenzenesulfonyl chloride (1.57 g, 7.62 mmol) and ethyl 3-amino-4-(3-pyridyl)butanoate hydrochloride (2.14 g, 7.62 mmol) in dimethylformamide (20 mL) and the reaction mixture was stirred for 18 h at rt. The solvent was removed in vacuo. The residue was partitioned between ethyl acetate (200 mL) and sodium bicarbonate (saturated, 100 mL). The organic layer was washed with brine (100 mL) and dried (MgSO$_4$) and was concentrated to afford 2.1 g (73%) of the desired product. $^1$H NMR (CD$_3$OD) δ ?8.2–8.35 (m, 2H), 7.04–7.42 (m, 6H), 3.79–4.11 (m, 6H), 2.45–2.90 (m, 4H), 1.2–1.4 (m, 3H).

STEP 2

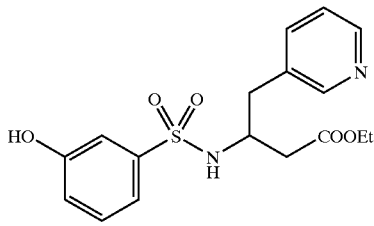

Ethyl 3-N-(3-hydroxyphenylsulfonyl)-4-(3-pyridyl)aminobutanoate

Boron tribromide (1 mL) was added to a solution of ethyl 3-N-(3-methoxyphenylsulfonyl)-4-(3-pyridyl)aminobutanoate (2.0 g, 5.29 mmol) in dichloromethane (20 mL) at rt. The reaction mixture was stirred for 18 h and was quenched with ethanol and was concentrated. The residue was dissolved in ethyl acetate (100 mL) and was washed with sodium bicarbonate (100 mL), dried and was concentrated to afford 1.40 g (73%) of the desired product. $^1$H NMR (CD$_3$OD) δ 6.8–8.35 (m, 8H), 3.79–4.11 (m, 3H), 2.45–2.90 (m, 4H), 1.16–1.2 (m, 3H).

STEP 3

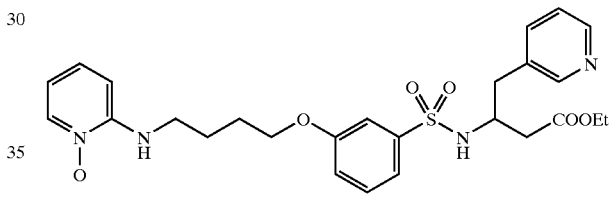

Ethyl 3-N-[4-(2-N-oxypyridyl)amino]-1-butyloxyphenylsulfonyl)-4-(3-pyridyl)aminobutanoate A solution of DEAD (1.34 g, 7.701 mmol) and N-(2-pyridyl-N-oxide)-3-aminobutanol (1.40 g, 7.69 mmol) in DMF (15 mL) was added to a solution of methyl 3-N-(3-hydroxyphenylsulfonyl)-4-(3-pyridyl)aminobutanoate (1.4 g, 3.846 mmol) and triphenylphosphine (2.12 g, 8.09 mmol) in DMF (10 mL) over a period of 1 min (mildly exothermic reaction) and the reaction mixture was stirred for 24 h. DMF was removed in vacuo and the residue was purified by hplc (reverse phase C18, 10%–100% gradient of acetonitrile in water containing 0.05% TFA) to afford 0.9 g (33%) of the desired product as its TFA salt as solid. $^1$H NMR (CD$_3$OD) δ 8.64 (m, 1H), 8.35 (m, 1H), 8.15 (m, 1H), 7.87 (m, 1H), 7.69 (m, 1H), 7.35 (m, 1H), 7.08–7.22 (m, 3H), 6.79 (m, 1H), 3.82–4.16 (m, 6H), 3.48 (m, 3H), 2.8–3.15 (m, 2H), 2.35–2.60 (m, 2H), 1.8–2.0 (m, 4H), 1.2–1.45 (m, 3H).

STEP 4

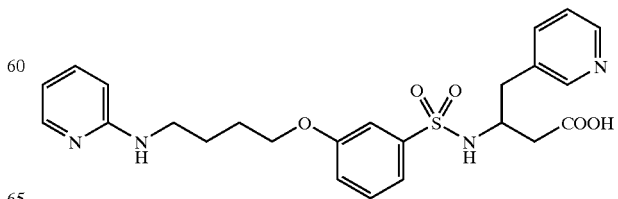

3-[4-(2-pyridinyl)amino]-1-butyloxyphenylsulfonyl)-3-(3-pyridyl)aminobutanoic acid A mixture of Ethyl 3-N-[4-(2-N-pyridyl)amino]-1-butyloxyphenylsulfonyl)-4-(3-pyridyl)aminobutanoate (1.0 g,), palladium/C (0.2 g), cyclohexene (2 mL) in ethyl alcohol (25 mL) was heated at reflux over 24 h. The reaction mixture was filtered, and the residue was washed with additional amount of ethyl alcohol (10 mL). The combined filtrates were concentrated. The residue was added ethanol (10 mL) and water (5 mL) and lithium hydroxide was added till the solution was slightly basic (pH 11) and stirred for 8 h. The reaction mixture was concentrated and the residue was dissolved in water (5 mL) and the pH was adjusted to 2 by the addition of TFA. This was purified by hplc (reverse phase C18, 10%–100% gradient of acetonitrile in water containing 0.05% TFA) and the pure fractions were combined and lyophilized to afford 0.29 g of the desired product as its TFA salt. $^1$H NMR (CD$_3$OD) δ 8.60–8.62 (m, 2H), 8.30 (m, 1H), 7.80–7.88 (m, 3H), 6.8–7.4 (m, 6H), 3.82–4.16 (m, 3H), 3.43 (m, 2H), 3.1–3.2 (m, 1H), 2.8–2.9 (m, 1H), 2.35–2.60 (m, 2H), 1.8–2.0 (m, 4H). Anal. Calcd for C$_{24}$H$_{28}$N$_4$SO$_5$: Mol. Wt, 485.1859 (M+H). Found: Mol. Wt, 485.1865 (M+H, HRFABMS).

EXAMPLE 14

3-[3-(2-pyridinyl)amino]-1-butyloxyphenylsulfonyl)-3-(phenethyl)aminopropionic acid

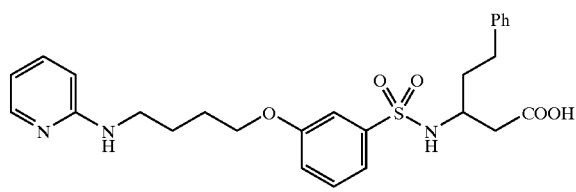

STEP 1

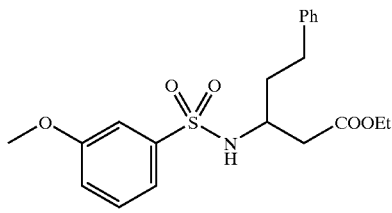

Ethyl 3-N-(3-metoxyphenylsulfonyl)-3-(phenethyl)aminopropionate

Triethylamine (4.68 mL) was added to a solution of m-methoxybenzenesulfonyl chloride (3.46 g, 16.76 mmol) and ethyl 3-amino-3-(phenethyl)propionate hydrochloride (4.0 g, 16.76 mmol) in dimethylacetamide (30 mL) and the reaction mixture was stirred for 18 h at rt. The solvent was removed in vacuo. The residue was partitioned between ethyl acetate (200 mL) and sodium bicarbonate (saturated, 200 mL). The organic layer was washed with brine (200 mL) and dried (MgSO4) and was concentrated to afford 4.2 g (64%) of the desired product. $^1$H NMR (CD$_3$OD) δ 6.97–7.46 (m, 9H), 3.9–4.1 (m, 2H), 3.83 (s, 3H), 3.6 (m, 1H), 2.3–2.6 (m, 4H), 1.6–1.8 (m, 2H), 1.1–1.2 (m, 3H).

STEP 2

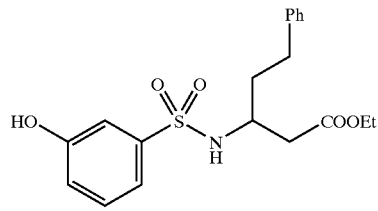

Ethyl 3-N -(3-hydroxyphenylsulfonyl)-3-(phenethyl)aminopropionate

Boron tribromide (4 mL) was added to a solution of ethyl 3-N-(3-methoxyphenylsulfonyl)-3-(phenethyl)aminopropionate (3.80 g, 9.38 mmol) in dichloromethane (75 mL) at rt. The reaction mixture was stirred for 18 h and was quenched with ethanol and was concentrated. The residue was dissolved in ethyl acetate (200 mL) and was washed with sodium bicarbonate (200 mL), dried and was concentrated to afford 1.68 g (46%) of the desired product. $^1$H NMR (CD$_3$OD) δ 6.95–7.36 (m, 9H), 3.9–4.1 (m, 2H), 3.59 (m, 1H), 2.3–2.6 (m, 4H), 1.6–1.8 (m. 2H), 1.1–1.2 (m, 3H).

STEP 3

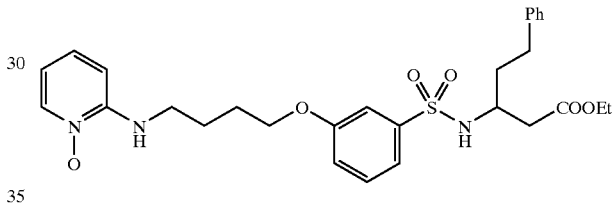

Ethyl 3-N-[4-(2-N-oxypyridyl)amino]-1-butyloxyphenylsulfonyl)-3-(phenethyl)aminopropionate A solution of DEAD (0.89 g, 5.114 mmol) and N-(2-pyridyl-N-oxide)-3-aminobutanol (0.931 g, 5.114 mmol) in DMF (15 mL) was added to a solution of methyl 3-N-(3-hydroxyphenylsulfonyl)-3-(phenethyl)aminopropionate (1.0 g, 2.557 mmol) and triphenylphosphine (1.41 g, 5.37 mmol) in DMF (10 mL) over a period of 1 min (mildly exothermic reaction) and the reaction mixture was stirred for 24 h. DMF was removed in vacuo and the residue was purified by hplc (reverse phase C18, 10%–100% gradient of acetonitrile in water containing 0.05% TFA) to afford 0.8 g (56%) of the desired product as its TFA salt as a solid. $^1$H NMR (CD$_3$OD) δ 8.14 (m, 1H), 7.61–7.70 (m, 1H), 7.34–7.46 (m, 3H), 6.75–7.20 (m, 8H), 3.9–4.1 (m, 4H), 3.59 (m, 1H), 3.4–3.5 (m, 2H), 2.3–2.6 (m, 4H), 1.5–2.0 (m, 6H), 1.1–1.2(m, 3H).

Step 4

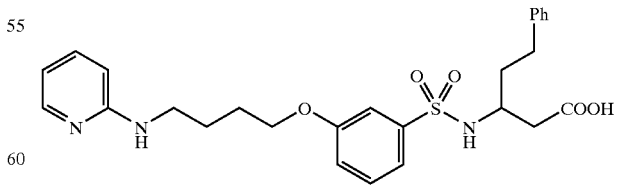

3-[3-(2-pyridinyl)amino]-1-butyloxyphenylsulfonyl)-3-(phenethyl)aminopropionic acid A mixture of methyl 3-[3-(2-N-oxypyridyl)amino]-1-butyloxy-phenyl-3-(phenethyl)aminopropionate (0.77 g,), palladium/C (0.2 g), cyclohexene (2 mL) in ethyl alcohol (25 mL) was heated at reflux over 24 h. The reaction mixture was filtered, and the residue was washed with additional amount of ethyl alcohol (10 mL). The combined filtrates were concentrated. The residue was added ethanol (10 mL) and water (5 mL) and lithium hydroxide was added till the solution was slightly basic (pH 11) and stirred for 8 h. The reaction mixture was concentrated and the residue was dissolved in water (5 mL) and the pH was adjusted to 2 by the addition of TFA. This was purified by hplc (reverse phase C18, 10%–100% gradient of acetonitrile in water containing 0.05% TFA) and the pure fractions were combined and lyophilized to afford 0.20 g of the desired product as its TFA salt. $^1$H NMR (CD$_3$OD) δ 7.6–7.8 (m, 2H), 7.2–7.35 (m, 3H), 6.7–7.10 (m, 8H), 3.9–4.1 (m, 2H), 3.40 (m, 1H), 3.26–3.3 (m, 2H), 2.2–2.5 (m, 4H), 1.5–2.0 (m. 6H. Anal. Calcd for C$_{26}$H$_{31}$N$_3$SO$_5$: Mol. Wt, 498.2063 (M+H). Found: 498.2081 (M+H, HRFABMS).

EXAMPLE 15

β-[[[3-[3-(2-pyridinylamino)butoxy]phenyl]sulfonyl]methyl]benzenepropanoic acid

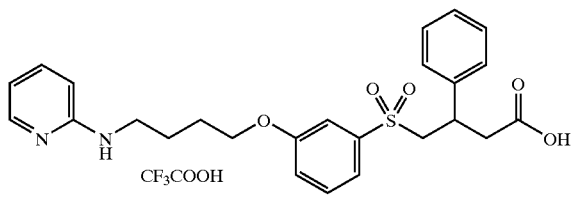

STEP A

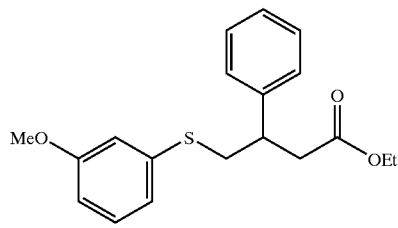

β-[[(3-methoxyphenyl)thio]methyl]benzenepropanoic acid, ethyl ester

To a solution of 3-methoxy-thiophenol (1.4 g, 0.01 mol) and 2-phenylbutyrolactone 2a (1.5 g, 0.0093 mol, (Tetrahedron 47, (8) 1525–40, 1991) in DMF (10.0 mL) were added potassium carbonate (1.4 g, 0.01 mol) and 18-crown-C (0.05 g), and the mixture was heated at 75° C. for 12 h under an atmosphere of argon. The reaction mixture was cooled, and partioned between 5% citric acid (25 mL) and ethylacetate (50 mL). The organic phase was washed with water (2×25 mL), dried dried (Na$_2$SO$_4$) and concentrated under reduced pressure to give a yellow syrup. This was purified by silica gel flash chromatography using 20% EtOAc in hexane. Fractions containing the desired acid as monitored by ES mass spectrometry, [m/z=303 (M+H)] were combined and concentrated. This material was dissolved in EtOH (5 mL), added 4N HCl/dioxane (5.0 mL) and stirred at room temperature for 1 h, and at 70° C. for 1 h. The resulting solution was concentrated to dryness and the residue was purified by silica gel flash chromatography using 20% EtOAc in hexane to give 1.2 g (40%) of the desired ester as a pale yellow liquid: $^1$H-NMR (400 Mz, CDCl$_3$) δ 7.35–7.15 (m, 5H), 6.87 (m, m 1H), 6.85 (m, 1H), 6.70(m, 1H), 4.02 (m, 2H), 3.77 (m, 3H), 3.18 (d, 2H, J=7.2 Hz), 2.92 (dd, 1H, J=6.4 Hz), 2.65 (dd, 1H, J=8.0 Hz), and 1.11 (t, 3H, J=6.8 Hz); ES-MS m/z 331 (M+H)+; HR-MS Calcd C$_{19}$H$_{23}$O$_3$S 331.1100, found 331.1377.

STEP 2

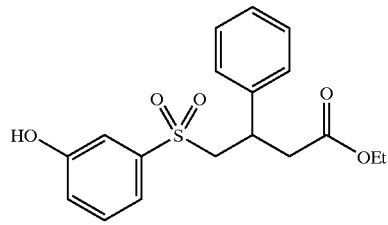

β-[[(3-hydroxyphenyl)sulfonyl]methyl]benzenepropanoic acid ethyl ester

A mixture of the product from step A (0.66 g, 0.002 mol) and oxone (2.5 g) in ethanol (12.0 mL) and water (3.0 mL) was stirred at room temperature for 3 h and filtered. The filtrate was concentrated to dryness under reduced pressure and the residue was purified by silica gel flash chromatography to afford the sulphone (0.55 g, 76%) as a colorless syrup: $^1$H-NMR (400 Mz, CDCl$_3$) δ 7.37 (m, 2H), 7.19 (m, 4H), 7.08 (m 3H), 3.99 (m, 2H), 3.81 (s, 3H), 3.73 (m 1H), 3.54 (dd, 1H), 3.43 (dd, 1H, J=5.6 Hz), 2.98 (dd, 1H, J=5.6 Hz), 2.69 (dd, 1H, J=8.8 Hz),and 1.11 (t, 3H, J=6.8 Hz); ES-MS m/z 363 (M+H)+. This material was dissolved in dichloromethane and added with boron-tribromide (0.3 mL), and the mixture was stirred for 30 min. It was then stirred at room temperature for another 30 min. The reaction mixture was cooled, added cold EtOH (1.0 mL) and concentrated to dryness. The residue was treated with an additional 5 mL of ethanol and concentrated to dryness under reduced pressure. The resulting substance was purified by silica gel flash chromatography using 40% EtOAc in hexane to furnish 0.42 g (87%) of the desired phenol as a white solid: $^1$H-NMR (400 Mz, CDCl$_3$) δ 7.33 (m, 2H), 7.24–7.12 m, 4H), 7.07 (m, 3H), 6.27 (s, 1H), 3.75 (m 2H), 3.46 (m, 1H), 3.33 (dd, 1H, J=7.6 Hz), 3.19 (d, 1H, J=6.4 Hz), 2.73 (dd, 1H, J=6.0 Hz), 2.46 (dd, 1H, J=8.4 Hz), 1.1 (t, 3H, J=7.2 Hz); ES-MS m/z 366 (M+NH4)+; HR-MS calcd C$_{18}$H$_{21}$O$_5$S 366.1375, found 366.1378.

STEP 3

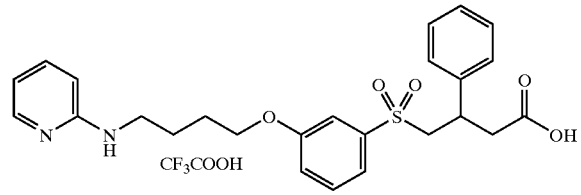

β-[[[3-[3-(2-pyridinylamino)butoxy]phenyl]-sulfonyl]methyl]benzenepropanoic acid To a solution of the product from step B (0.4 g, 0.00115 mol) in THF at 0° C., was added triphenylphosphine (0.45 g, 0.0017 mol) and stirred under an atmosphere of argon. After 15 min, added diisopropylazodicarboxylate (0.3 mL) and stirred for 10 min. To this mixture, was added a solution of 3c (0.3 g, 0.0017 mol) in DMF (3.0 mL) and the mixture was stirred at room temperature for 16 h. The solvents were distilled in vacuo, and the residue was purified by reverse-phase HPLC using 10–90% acetonitrile/water gradient (30 min) at a flow rate of 70 mL/min. The appropriate fractions as revealed by ES mass spectrometry (m/z=513) were combined and freeze dried to give 0.27 g of the desired product. This was dissloved in ethanol (10.0 mL), cyclohexene (0.3 mL)and Pd/C (10%, 0.3 g) were added and the mixture was heated to reflux for 3 h. The reaction mixture was filtered through a pad of celite, and the filtrate was concentrated. The resulting residue was suspended in acetonitrile (0.5 mL), added 1 M LiOH (1.5 mL) and the mixture was heated at 70° C. for 45 min. It was then cooled, diluted with water (1 mL), acidified with trifluoroacetic acid, and the product was isolated by reverse-phase HPLC using 10–90% acetonitrile/water gradient (30 min) at a flow rate of 70 mL/min. The appropriate fractions as revealed by ES mass spectrometry (m/z=469) were combined and freeze dried to give 0.09 g of the desired product: $^1$H-NMR (400 Mz, $CD_3$ OD) δ 7.85 (m, 1H), 7.8 m, 1H), 7.37 (m, 1H), 7.15 (m, 1H), 7.18–7.0 (m, 8H), 6.86 (t, 1H), 4.05 (m, 2H), 3.68 (d, 2H, J=1.2 Hz), 3.58 (m, 1H), 3.42 (m, 2H), 2.84 (dd, 1H), 2.6 (dd, 1H), 1.92 (br s, 4H);ES-MS m/z 469 (M+H)$^+$ HR-MS Calcd $C_{25}H_{29}N_2O_5S$ (M+H)$^+$ 469.1797, found 469.1806.

EXAMPLE 16

β-[[[3-[3-(2-pyridinylamino)butoxy]phenyl]sulfonyl]methyl]-4-fluorobenzenepropanoic acid

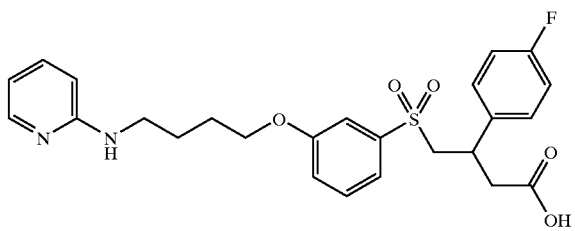

STEP 1

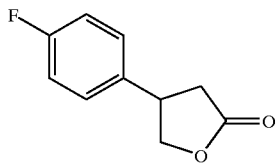

β-4-fluoro-phenylbutyrolactone

A mixture of commercially available 1-fluoro-4-iodobenzene (10.22 g, 0.046 mol), 2-butene-1,4-diol (6.07 g, 0.069 mol), $K_2CO_3$ (15.9 g, 0.115 mol) and $(BU)_4NCl$ (12.79 g, 0.046 mol) in anhydrous DMF (56 mL) was added to a Fisher-Porter bottle. The bottle was sealed, evacuated and purged three times with nitrogen. Pd(OAc)$_2$ (0.31 g, 0.0014 mol), was added and bottle was resealed, evacuated and charged with nitrogen (10 psi). The mixture was heated in an oil bath at 70° C. under nitrogen atmosphere. After 3 h of heating, it was cooled and filtered through a pad of celite. The filtrate was extracted with EtOAc (4×125 mL), the combined organic extracts were washed with water (2×150 mL), and dried over anhydrous $Na_2SO_4$. The organic extracts were concentrated and purified by silica gel flash chromatography using 30% EtOAc in hexane to afford the desired β-4-fluoro-phenylbutyrolactol intermediate 6.5 g (78%). To a solution of lactol (2.96 g, 0.016 mol) in anhydrous toluene (82 mL) was added $Ag_2CO_3$ (18.02 g, 0.065 mol) and the suspension was heated in oil bath at 85° C. under nitrogen atmosphere. After 1 h of heating the reaction was cooled and filtered through a pad of celite. The filtrate was concentrated and purified by silica gel flash chromatography using 30% EtOAc in hexane to afford the desired lactone, as a yellow syrup, 2.8 g (95%). This was used as such in step B. MS and 1H-NMR were consistent with the desired structure. GC-MS: (m/z) (MH)$^+$=181; $^1$H-NMR (CD$_3$OD, 400 Hz) δ 7.0 (m, 2H), 4.6 (t, 1H), 4.2 (t, 1H), 3.8 (m, 1H), 2.9 (dd, 1H), 2.7 (dd, 1H).

STEP 2

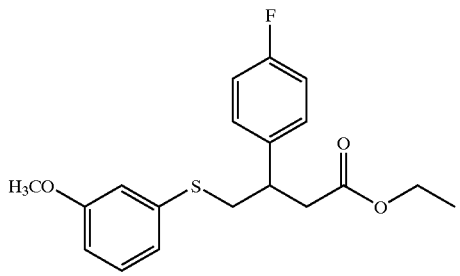

To a solution of lactone, (2b), (2.0 g, 0.011 mol) and 3-methoxy thiophenol (2.3 g, 0.016 mol, see Ref. *Tetrahedron* 47 (8)1525–40, 1991) in anhydrous DMF (20 mL) were added potassium carbonate (2.3 g, 0.016 mol) and 18-crown-6 (0.20 g). The mixture was heated at 80° C. for 3 h under anhydrous conditions (CaSO$_4$ dry tube). The reaction mixture was cooled and partitioned between acetic acid (2 eq) and EtOAc (50 mL). Organic extracts were combined and concentrated under reduced pressure. The residue was rinsed with ethanol (20 mL), cooled and filtered. The filtrate was concentrated, dried and used as is. MS, m/z(M+NH4)=342. To a chilled solution (0° C.) of this crude material (2.67 g) in ethanol (15 mL) was added 4N HCl/dioxane (5 mL) and stirred at RT for 15 min. The reaction mixture was heated at 80° C. for 1.5 h and monitored by TLC for completion (25% EtOAc in hexane). The resulting solution was cooled and extracted with EtOAc and water. The organic extracts were dried over Na2SO4 and concentrated to dryness. The yellow residue was purified by silica gel flash chromatography using 25% EtOAc in hexane to afford desired ester, (4b), 2.4 g (63%). MS and $^1$H-NMR were consistent with the desired structure. $^1$H-NMR (CD$_3$OD, 400 Hz) δ 7.1 (m, 3H), 6.9 (t, 2H), 6.84 (m, 2H), 6.72 (dd, 1H), 3.9 (q, 2H), 3.75 (s, 3H), 3.28 (m, 3H), 2.8 (dd, 1H) 2.6 (dd, 1H), 1.07 (t, 3H). HR-MS (ES) m/z calcd $C_{19}H_{21}O_3SF$ (MH)$^+$ 349.1274, found 349.1248.

STEP 3

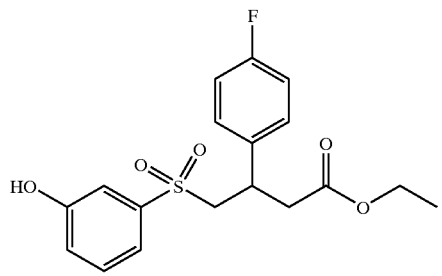

β-[[(3-hydroxyphenyl)sulfonyl]methyl]-4-fluorobenzenepropanoic acid ethyl ester

A mixture of the ester (1.12 g 0.0032 mol) and oxone (2.96 g, 0.0048 mol) in ethanol (16 mL)/water (4 mL) was stirred in an ice bath for 3 h. It was then filtered and the filtrate was concentrated to dryness under reduced pressure. The milky yellow residue was purified by silica gel flash chromatography using 30% EtOAc in hexane to afford the sulfone, β-[[(3-methoxyphenyl)sulfonyl]methyl]-4-fluorobenzenepropanoic acid ethyl ester 0.98 g (80%): $^1$H-NMR (CD$_3$OD, 400 Hz) 7.4 (m, 1H), 7.3 (m, 1H), 7.1 (m, 4H), 6.85 (t, 2H), 4.0 (q, 2H), 3.8 (s, 3H), 3.65 (m, 3H), 2.85 (dd, 1H) 2.6 (dd, 1H), 1.07 (t, 3H) HR-MS (ES) m/z calcd $C_{19}H_{21}O_5SF$ (MH)$^+$ 381.1172, found 381.1197. This material was used as such in the following step. To a cold solution of the sulphone, β-[[(3-methoxyphenyl)sulfonyl] methyl]-4-fluorobenzenepropanoic acid, ethyl ester (0.98 g. 0.0025 mol) in dichloromethane (10 ml) was added borontribromide (0.5 mL) and stirred for 1 h at 0° C. The reaction mixture was then stirred at RT for 1.5 h and monitored by ES mass spectrometry for completion (M+H m/z=367). The reaction mixture was cooled and quenched with EtOH (10 mL). The solution was diluted with dichloromethane and washed with water. The organic extracts were dried over $Na_2SO_4$ and concentrated to dryness under reduced pressure. The residue was purified by silica gel flash chromatography using 50% EtOAc in hexane to afford the desired phenol, (5b), 0.667 g (70%): $^1$H-NMR (CD$_3$OD, 400 Hz) δ 7.3 (m, 1H), 7.1 (m, 5H), 6.85 (m, 2H), 3.9 (q, 2H), 3.6 (m, 3H), 2.8 (dd, 1H) 2.6 (dd, 1H), 1.07 (t, 3H); HR-MS (ES) m/z calcd $C_{18}H_{19}O_5SF$ (MH)$^+$ 367.1015, found 367.1052.

STEP 5

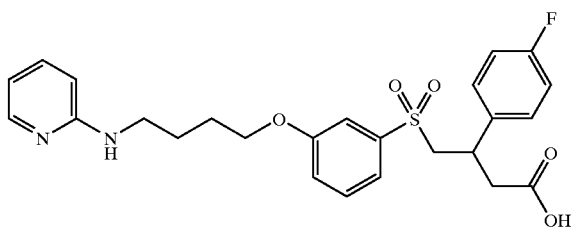

β-[[3-[3-(2-pyridinylamino)butoxy]phenyl]sulfonyl] methyl]-4-fluorobenzenepropanoic acid To a cold solution of the phenol, (5b), (0.355 g, 0.093 mol) in anhydrous DMF (5 mL) was added triphenylphosphine (0.383 g, 0.00146 mol) and stirred at 0° C. under an atmosphere of nitrogen. After 5 minutes, diisopropylazodicarboxylate (0.27 g, 0.00136 mol) was added dropwise and stirred for 15 min. Then added a cold solution of the pyridine N-oxide (0.266 g, 0.00146 mol) in anhydrous DMF (5 mL) and stirred at 0° C. for 30 min and at RT overnight. The solvent was distilled in vacuo and the residue was purified by reverse phase HPLC using 5–95% acetontrile/water to 50-50% acetonitrile/water gradient (30 min) at a flow rate of 70 mL/min. The appropriate fractions were combined according to ES mass spectrometry (M+H=531) and freeze dried to give 0.54 g of the desired product. This was used as such in the following step. The product was dissolved in ethanol (10 mL), cyclohexene (0.39 g, 0.0048 mol) and Pd/C (10%, 0.5 g). The reaction mixture was heated to reflux (80° C.) for 3.5 h. The reaction was monitored by ES mass spectrometry for completion (M+H m/z=515 and M+H m/z=279). The mixture was cooled, filtered through a pad of celite, and the filtrate was concentrated. The residue, 0.493 g, was suspended in 1 M LiOH (5 mL) and heated for 1 h at 80° C. The reaction was monitored by ES mass spectrometry for completion (M−H=485 M+H=279). The reaction mixture was cooled and extracted with dichloromethane and water to remove triphenylphosphinoxide. The aqueous layer (M−H=485) was concentrated and acidified with TFA. The product was isolated by reverse phase HPLC using 5–95% acetonitrile/water to 50-50% acetonitrile/water gradient (30 min) at a flow rate of 70 mL/min. The appropriate fractions were combined according to ES mass spectrometry (M+H=487) and freeze dried to afford the desired acid, (5.3 mg): $^1$H-NMR (CD$_3$OD, 400 Hz) δ (7.82 (m, 2H), 7.38 (m, 2H), 7.1(m, 4H), 6.8 (m, 2H), 4.0 (m, 2H), 3.6 (m, 3H), 3.4 (m, 2H), 2.8 (dd, 2H), 2.58 (m, 2H), 1.91 (s, 4H). HR-MS (ES) m/z calcd $C_{25}H_{27}N_2O_5SF$ (MH)$^+$ 487.1703, found 487.1722.

EXAMPLE 17

(3S)-3-[({3-[4-(Pyridin-2-ylamino)butoxy]phenyl}sulfonyl)amino]pent-4-ynoic acid

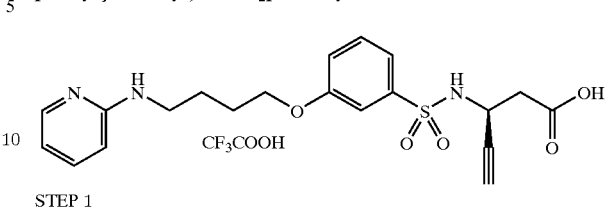

STEP 1

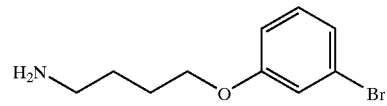

4-(3-Bromophenoxy)butan-1-amine

To a solution of 4-bromobutylphthalimide (Aldrich, 20 g) and 3-bromomphenol (Aldrich, 12.3 g) in acetone (125 mL) was added potassium carbonate (Aldrich, 11 g). The mixture was stirred and heated to reflux for 16 hours. The mixture was filtered and the filtrate concentrated in vacuo. The residue was extracted with ethyl acetate and water. The organic phase was dried over MgSO$_4$ and concentrated in vacuo to provide a colorless solid (27 g). The solid was dissolved in hot ethanol (300 mL). Hydrazine (Aldrich, 98%, 25 mL) and water (10 mL) were added to the solution. The mixture was allowed to stand at room temperature for 16 hours. The precipitated solid was filtered and the filtrate concentrated in vacuo. The residue was extracted with ethyl acetate and 50% aqueous potassium carbonate. The organic phase was dried over MgSO$_4$ and concentrated in vacuo to provide the title compound (12.5 g). $^1$H (CDCl$_3$); δ 7.12 (1H, t); 7.06 (1H, dt); 7.04 (1H, m); 6.82 (1H, ddd); 3.95 (2H, t); 2.76 (2H, t); 1.81 (2H, p); 1.60 (2H, p); 1.30 (2H, br. s).

STEP 2

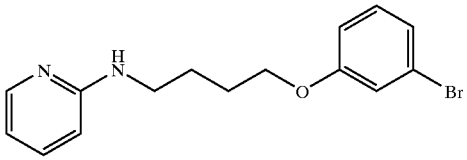

N-[4-(3-Bromophenoxy)butyl]pyridin-2-amine

A mixture of the product of Example-1 (12.5 g), 2-fluoropyridine (Aldrich, 100 mL) and N,N-diisopropylethylamine (Aldrich, 9 mL) was heated to reflux for 48 hours. The volatiles were removed in vacuo. The residue was extracted with ethyl acetate and water. The organic extract was washed with saturated aqueous sodium bicarbonate solution, dried over MgSO$_4$ and concentrated in vacuo. The residue was triturated with ether and hexane to provide the title compound as a colorless solid. $^1$H (CDCl$_3$) :□ 8.07 (1H, ddd); 7.39 (1H, ddd); 7.10 (1H, t); 7.05 (1H, dt); 7.03 (1H, t); 6.80 (1H, ddd); 6.54 (1H, ddd); 6.35 (1H, dt); 4.74 (1H, br. t); 3.93 (2H, t); 3.32 (2H, q); 1.86 (2H, p); 1.77 (2H, p).

STEP 3

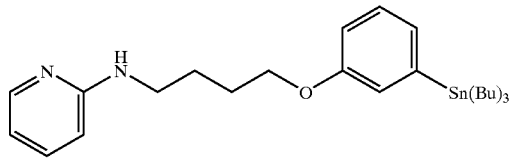

N-{4-[3-(Tributylstannyl)phenoxy]butyl}pyridin-2-amine

Potassium hydride (Aldrich, 3.5 g of a 35% mineral oil suspension) was washed with pentane and suspended in THF (85 mL) at 0° C. The product of Example-2 (8.4 g) was added as a solid all at once. The cooling bath was removed and the mixture stirred for 20 minutes. The mixture was cooled to −78° C. and tert.butyl lithium (Aldrich, 46 mL, 1.7 molar in hexane) was added over 2 minutes. After 10 minutes tributyltin chloride (Aldrich, 15 mL) was added over 2 minutes. The mixture was stirred at −780 C for 20 minutes, 0° C. for 4 h and at 23° C. for 1 h. Aqueous saturated ammonium chloride (12 mL) was added. The mixture was extracted with ethyl acetate and water. The organic phase was washed with water, dried over $MgSO_4$ and concentrated in vacuo. The residue was purified by chromatography to give the title product as a colorless oil. $^1H$ (CDCl$_3$): δ 8.08 (1H, ddd); 7.41 (1H, ddd); 7.24 (1H, dd); 7.03 (1H, t); 7.00 (1H, d); 6.82 (1H, ddd); 6.56 (1H, ddd); 6.37 (1H, dt); 4.53 (1H, br. t); 4.01 (2H, t); 3.36 (2H, q); 1.91 (2H, p); 1.82 (2H, p); 1.53 (6H, p); 1.33 (6H, h); 1.04 (6H, t); 0.88 (9H, t).

STEP 4

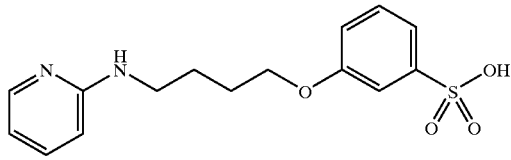

3-[4-(Pyridin-2-ylamino)butoxy]benzenesulfonic acid

To a stirred solution of trimethylsilyl chlorosulfonate (Aldrich, 11.1 mL) in carbon tetrachloride (Aldrich, 150 mL) at 0° C., was added the product of Example-3 (19 g) over 3 minutes. The cooling bath was removed after 1 hour and stirring continued for another 30 minutes. Saturated aqueous sodium bicarbonate (630 mL) was added to the reaction mixture and stirring continued for 30 minutes. The reaction mixture was extracted with ether and water. The aqueous phase was concentrated in vacuo. The residue was digested with boiling ethanol (2×150 mL) and filtered while hot. The filtrate was concentrated in vacuo and the residue was triturated with ether and filtered to give the sodium salt of the title product (6.6 g). The sodium salt was suspended in aqueous ethanol (50%, 100 mL) and shirred at 23° C. The mixture was acidified with concentrated hydrochloric acid to pH 4. The precipitated white solid was filtered and washed with aqueous ethanol (50%, 100 mL) followed by ether (100 mL) to provide the title product as a colorless solid. $^1H$ (DMSO-d$_8$); δ 7.92 (1H, d); 7.38 (1H, t); 7.29 (1H, t); 7.21 (1H, d); 7.17 (1H, s); 6.93 (1H, d); 6.49 (2H, m); 4.01 (2H, t); 3.27 (2H, t); 1.80 (2H, p); 1.67 (2H, p).

STEP 5

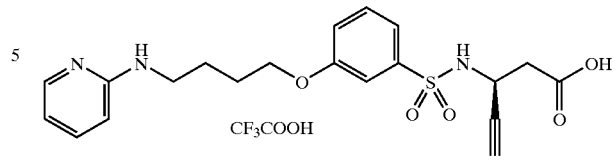

(3S)-3-[({3-[4-(Pyridin-2-ylamino)butoxy[phenyl}sulfonyl)amino]pent-4-ynoic acid trifluoroacetate To a stirred suspension of the product of Example-4 (0.52 g), bromo-trispyrrolidino-phosphonium hexafluorophosphate (0.75 g) and ethyl (3S)-3-aminopent-4-ynoate hydrochloride (Ref: WO 9802410, 0.285 g) in dimethyl ace amide (Aldrich, 4 mL) was added diisoproylethylamine (0.86 mL). After 16 h at 23° C., the solution was heated on a steam bath for 16 hours. The mixture was extracted with ethyl acetate and water. The organic phase was washed with water, saturated solution of NaHCO$_3$, dried over MgSO$_4$ and concentrated in vacuo. The residue was heated with 4N hydrochloric acid (5 mL) heated on a steam bath for 16 hours. The solution was concentrated in vacuo and the residue was purified by HPLC to provide the title product as a gum. $^1H$ (DMSO-d$_6$):δ 8.78(1H, br. s); 8.34 (1H, d); 7.92 (1H, d); 7.88 (1H, t); 7.48 (1H, t); 7.37 (1H, d); 7.32 (1H, br. s); 7.19 (1H, dd); 7.04 (1H, d); 6.84 (1H, t); 4.27 (1H, qd); 4.09 (2H, t); 3.38 (2H, br. t); 3.07 (1H, d); 2.56 (2H, d); 1.85 (2H, p); 1.76 (2H, p).

EXAMPLE 18

(3S)-5-Phenyl-3-[({3-[4-(pyridin-2-ylamino)butoxy]phenyl}sulfonyl)amino]pent-4-ynoic acid

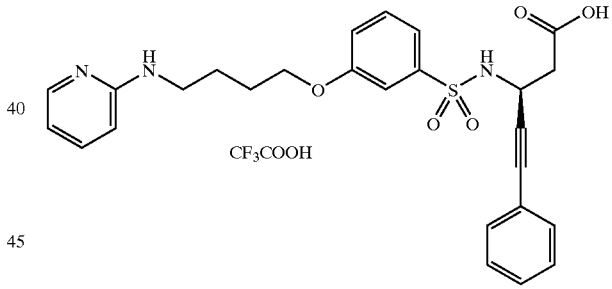

To a stirred solution of ethyl (3S)-3-aminopent-4-ynoate hydrochloride (Ref: WO 9802410, 20 g) in water (200 mL) at 23° C. was added sodium bicarbonate (20 g). Then ether (100 mL) and di-tert-butyl dicarbonate (Aldrich, 25 g) were added. After 16 hours, the mixture was extracted with ether and water. The organic extract was washed with aqueous potassium hydrogen sulfate (0.5N, 200 mL), dried over MgSO$_4$ and concentrated in vacuo to provide ethyl (3S)-3-[(tert-butoxycarbonyl)amino]pent-4-ynoate as a clear liquid. A mixture of this product (3.6 g), iodobenzene (Aldrich, 2.041 g) and dichlorobis(triphenylphosphine)palladium (II) (Aldrich, 70 mg), copper(I) iodide (Aldrich, 10 mg) and diethylamine (Aldrich, 60 mL) in a pressure bottle was purged with nitrogen and heated to 65° C. for 4 hours. The mixture was concentrated in vacuo. The residue was extracted with ethyl acetate and water. The organic extract was dried over MgSO$_4$ and concentrated in vacuo. The residue was purified by chromatography to provide the tert-butoxycarbonyl derivative of ethyl (3S)-3-amino-5- phenylpent-4-ynoate. This material was dissolved in 4 N HCL dioxane (Aldrich, 10 mL) and allowed to stand at 23° C. for 30 minutes. The volatiles were removed in vacuo to provide ethyl (3S)-3-amino-5-phenylpent-4-ynoate hydrochloride as colorless solid. $^1$H (DMSO-d$_6$): δ 7.43 (5H, m); 4.61 1 h, q); 4.13 (2H, q); 3.18 (1H, dd), 2.92 (1H, dd): 1.21 (3H, t). To a stirred suspension of this product (0.41 g) and the product of EXAMPLE 1, STEP 3 (0.52 g), bromotrispyrrolidino-phosphonium hexafluorophosphate (0.75 g) in dimethyl acetamide (Aldrich, 4 mL) was added diisoproylethylamine (0.86 mL). After 16 h at 23° C., the solution was heated on a steam bath for 16 hours. The mixture was extracted with ethyl acetate and water. The organic phase was washed with water, saturated solution of NaHCO$_3$, dried over MgSO$_4$ and concentrated in vacuo. The residue was heated with 4N hydrochloric acid (5 mL) heated on a steam bath for 16 hours. The solution was concentrated in vacuo and the residue was purified by HPLC to provide the title product as a gum. $^1$H (CD$_3$OD): δ 7.87 (1H, t); 7.81 (1H, d); 7.50 (1H, d); 7.42 (2H, m); 7.22 (3H, m); 7.08 (1H, d); 7.02 (3H, m); 6.87 (1H, t); 4.67 (1H, t); 4.00 (2H, t); 3.37 (2H, t); 2.77 (2H, d); 1.83 (4H, m).

EXAMPLE 19
(3S)-5-[3,5-Bis(trifluoromethyl)phenyl]-3-[({3-[4-(pyridin-2-ylamino)butoxy]-phenyl}sulfonyl)amino]pent-4-ynoic acid

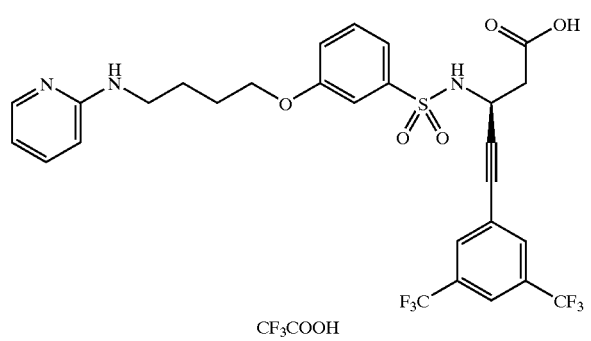

CF$_3$COOH

The procedure for the preparation of the product of EXAMPLE 18 was repeated using 1-iodo-3,5-bistrifluoromethyl)benzene (Aldrich) in the place of iodobenzene to provide the title product. $^1$H (CD$_3$OD): δ 7.90 (1H, s); 7.88 (1H, t); 7.82 (1H, d); 7.54 (2H, s); 7.52 (1H, d); 7.45 (1H, s); 7.42 (1H, t); 7.03 (2H, d); 6.87 (1H, t); 4.72 (1H, t); 4.02 (2H, br. t); 3.40 (2H, br. t); 2.82 (2H, d); 1.86 (4H, m).

EXAMPLE 20
(3S)-5-(3,5-Dichlorophenyl)-3-[({3-[4-(pyridin-2-ylamino)butoxy]phenyl}-sulfonyl)amino]pent-4-ynoic acid

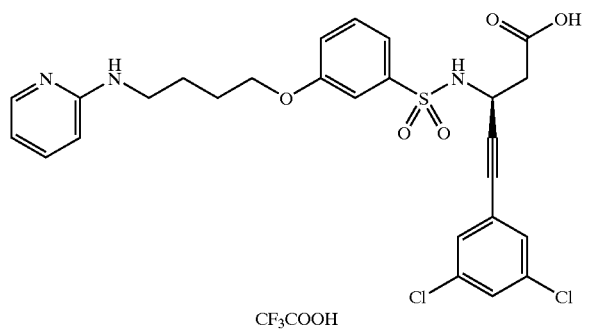

CF$_3$COOH

The procedure for the preparation of the product of EXAMPLE 18 was repeated using 1,3-dichloro-5-iodobenzene (Aldrich) in the place of iodobenzene to provide the title product. $^1$H (CD$_3$OD): δ 7.88 (1H, t); 7.82 (1H, d); 7.50 (1H, d); 7.45 (1H, t); 7.43 (1H, s); 7.36 (1H, s); 7.10 (1H, d); 7.03 (1H, d); 6.91 (2H, s); 6.88 (1H, t); 4.68 (1H, t); 4.04 (2H, t); 3.40 (2H, t); 2.78 (2H, d); 1.87 (4H, m).

EXAMPLE 21
(3S)-5-[2-(Aminosulfonyl)phenyl]-3-[({3-[4-(pyridin-2-ylamino)butoxy]-phenyl}sulfonyl)amino]pent-4-ynoic acid

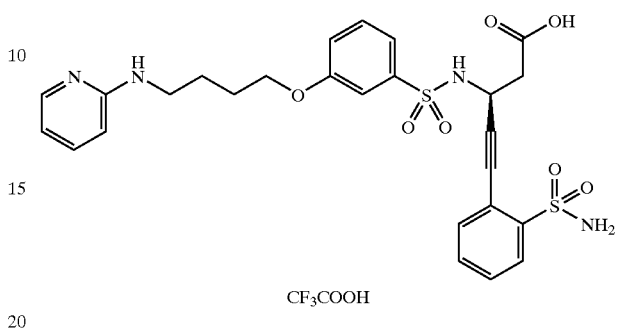

CF$_3$COOH

The procedure for the preparation of the product of EXAMPLE 18 was repeated using 2-iodobenzene-1-sulfonamide (Maybridge) in the place of iodobenzene to provide the title product. $^1$H (CD$_3$OD): δ 7.88 (2H, m); 7.81 (1H, d); 7.52 (1H, d); 7.44 (4H, m); 7.11 (1H, d); 7.05 (2H, m); 6.87 (1H, t); 4.68 (1H, t); 4.01 (2H, m); 3.37 (2H, m); 2.84 (2H, m); 1.82 (4H, m).

EXAMPLE 22
1-({3-[4-Pyridin-2-ylamino)butoxy]phenyl}sulfonyl)piperidine-3-carboxylic acid

CF$_3$COOH

The procedure for the preparation of the product of EXAMPLE 17 was repeated using ethyl nipecotate (Aldrich) in the place of ethyl (3S)-3-aminopent-4-ynoate hydrochloride to provide the title product. $^1$H (CD$_3$OD): δ 7.88 (1H, t); 7.82 (1H, d); 7.52 (1H, t); 7.33 (1H, d); 7.24 (1H, s); 7.22 (1H, d); 7.06 (1H, d); 6.87 (1H, t); 4.13 (2H, t); 3.69 (1H, d); 3.47 (3H, m); 2.57 (2H, m); 2.45 (1H, t); 1.94 (5H, m); 1.80 (1H, br. d); 1.60 (1H, br. q); 1.41 (1H, br. q).

EXAMPLE 23
1-({3-[4-(Pyridin-2-ylamino)butoxy]phenyl}sulfonyl)piperidine-4-carboxylic acid

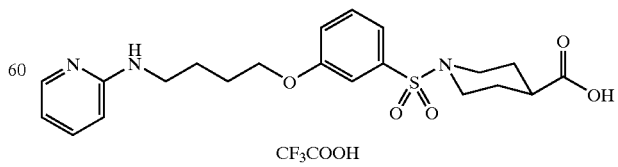

CF$_3$COOH

The procedure for the preparation of the product of EXAMPLE 17 was repeated using methyl isonipecotate (Aldrich) in the place of ethyl (3S)-3-aminopent-4-ynoate hydrochloride to provide the title product. $^1$H (CD3OD): δ 7.86 (1H, d); 7.61 (1H, t); 7.49 (1H, t); 7.32 (1H, d); 7.24 (1H, s); 7.20 (1H, d); 6.74 (1H, d); 6.66 (1H, t); 4.12 (2H, t); 3.57 (2H, br. d); 3.37 (2H, t); 2.52 (2H, t); 2.27 (1H, tt); 1.94 (4H, m); 1.84 (2H, p); 1.71 (2H, br. q).

EXAMPLE 24
N-({3-[4-(Pyridin-2-ylamino)butoxy]phenyl}sulfonyl)-L-aspartic acid

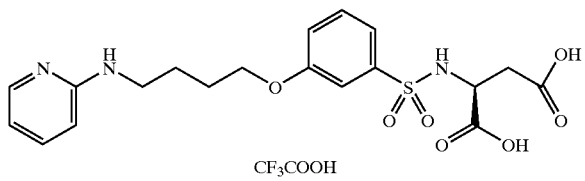

The procedure for the preparation of the product of EXAMPLE 17 was repeated using L-aspartic acid dimethyl ester hydrochloride (Aldrich) in the place of ethyl (3S)-3-aminopent-4-ynoate hydrochloride to provide the title product. $^1$H (CD$_3$OD): δ 7.88 (1H, t); 7.82 (1 H, d); 7.42 (3H, m); 7.13 (1H, m); 7.05 (1H, d); 6.87 (1H, t); 4.20 (1H, t); 4.12 (2H, t); 3.44 (2H, t); 2.71 (2H, m); 1.93 (4H, m).

EXAMPLE 25
2,2-Difluoro-3-phenyl-3-[({3-[4-(pyridin-2-ylamino)butoxy]phenyl}sulfonyl)amino]propanoic acid

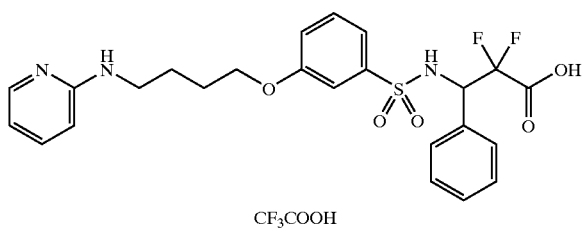

The procedure for the preparation of the product of EXAMPLE 17 was repeated using 3-amino-2,2-difluoro-3-phenyl-propionic acid ethyl ester (Ref: Chem.Pharm.Bull.; EN; 45; 11; 1997; 1793–1804) in the place of ethyl (3S)-3-aminopent-4-ynoate hydrochloride to provide the title product. $^1$H (CD$_3$OD): δ 7.90 (1H, t); 7.75 (1H, d); 7.27 (3H, m); 7.18 (5H, m); 7.05 (1H, d); 6.84 (2H, m); 5.10 (1H, t, J=13.5 Hz); 4.03 (2H, t); 3.44 (2H, t); 1.91 (4H, m).

EXAMPLE 26
N-({3-[4-(pyridin-2-ylamino)butoxy]phenyl}sulfonyl)-beta-alanine

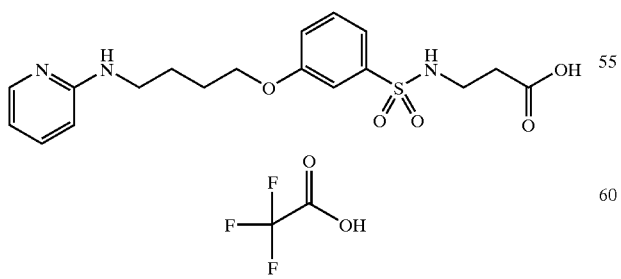

The title compound was prepared according to the method described for the preparation of EXAMPLE 17. 1H NMR (400 MHz, CD3OD) δ 7.88 (t, 1 H), 7.84 (d, 1 H), 7.49 (t, 1 H), 7.43 (d, 1 H), 7.38 (s, 1 H), 7.20 (d, 1 H), 7.04 (d, 1 H), 6.88 (t, 1 H), 4.14 (t, 2 H), 3.47 (t, 2 H), 3.11 (t, 2 H), 2.48 (t, 2 H), 1.98 (m, 4 H); MS (ESI+) for m/z394 (M+H)$^+$.

EXAMPLE 27
4-methyl-3-[({3-[4-(pyridin-2-ylamino)butoxy]phenyl}sulfonyl)amino]pentanoic acid

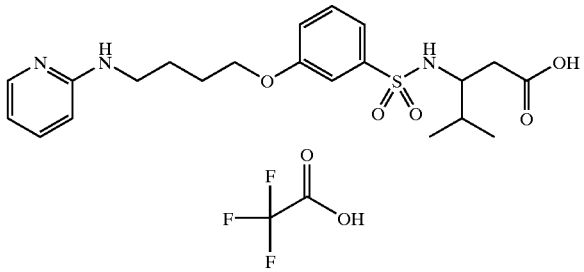

The title compound was prepared according to the method described for the preparation of EXAMPLE 17. 1H NMR (400 MHz, CD3OD) δ 7.92 (t, 1 H), 7.84 (d, 1 H), 7.46 (m, 2 H), 7.40 (s, 1 H), 7.17 (m, 1 H), 7.08 (d, 1 H), 6.90 (t, 1 H), 4.14 (t, 2 H), 3.52 (m, 1 H), 3.46 (t, 2 H), 2.38 (dd, 1 H), 2.14 (dd, 1 H), 1.97 (m, 4 H), 1.77 (m, 1 H), 0.87 (t, 6 H);MS (ESI+) for m/z 436 (M+H)$^+$.

EXAMPLE 28
3-cyclohexyl-3-[({3-[4-(pyridin-2-ylamino)butoxy]phenyl}sulfonyl)amino]propanoic acid

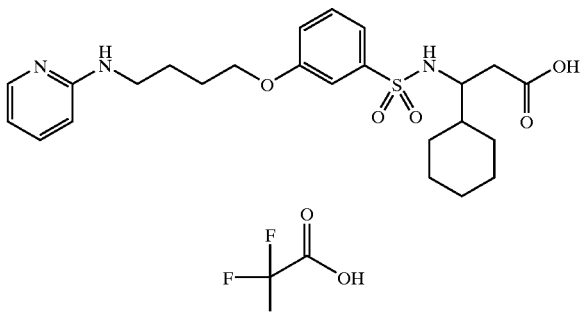

The title compound was prepared according to the method described for the preparation of EXAMPLE 17. $^1$H NMR (400 MHz, CD3OD) δ 7.91 (t, 1 H), 7.84 (d, 1 H), 7.46 (m, 2 H), 7.39 (s, 1 H), 7.16 (m, 1 H), 7.07 (d, 1 H), 6.89 (t, 1 H), 4.15 (m, 2 H), 3.53 (m, 1 H), 3.47 (t, 2 H), 2.40 (dd, 1 H), 2.16 (dd, 1 H), 1.98 (m, 4 H), 1.72 (m, 4 H), 1.63 (m, 1 H), 1.58 (m, 1 H), 1.40 (m, 1 H), 1.15 (m, 2 H), 1.08 (m, 1 H), 0.89 (m, 1 H); MS (ESI+) for m/z 476 (M+H)$^+$.

EXAMPLE 29
3-(4-methylphenyl)-3-[({3-[4-(pyridin-2-ylamino)butoxy]phenyl}sulfonyl)amino]propanoic acid
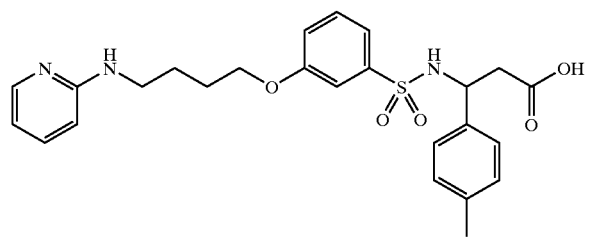
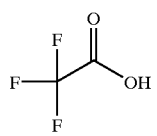
The compound was prepared according to the method described for the preparation of EXAMPLE 17. $^1$H NMR (400 MHz, CD3OD) δ 7.91 (t, 1 H), 7.85 (d, 1 H), 7.23 (m, 2 H), 7.06 (m, 2 H), 7.03–6.89 (m, 6 H), 4.72 (t, 1 H), 3.99 (m, 2 H), 3.47 (m, 2 H), 3.24 (m, 1 H), 2.75 (dd, 1 H), 2.67 (dd, 1 H), 2.22 (s, 3 H), 1.93 (m, 4 H); MS (ESI+) for m/z 484 (M+H)$^+$.
EXAMPLE 30
β-[[[3-[4-[(1,4,5,6-tetrahydro-2-pyrimidinyl)amino]butoxy]phenyl]sulfonyl]amino]benzenepropanoic acid
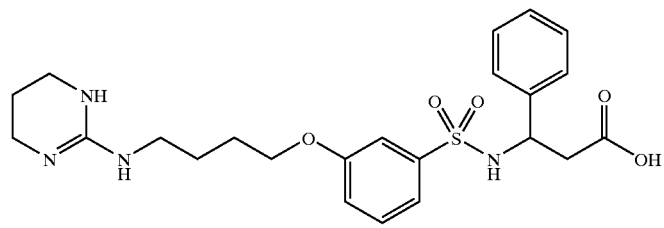
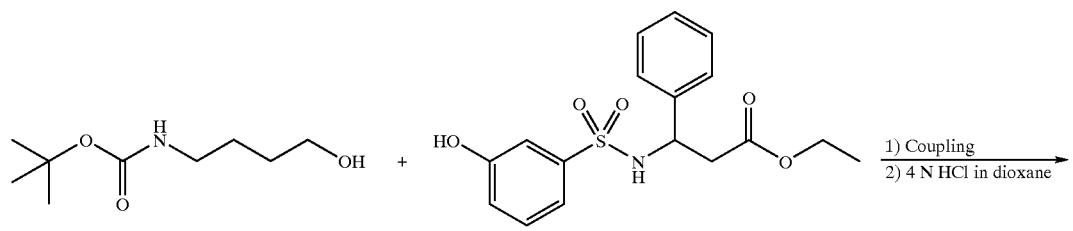
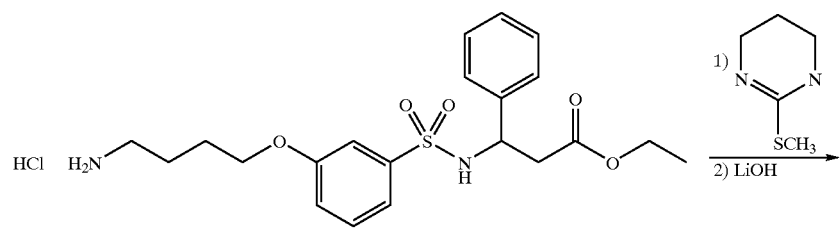
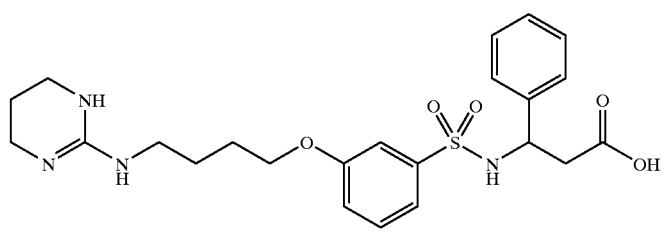

Step 1

β-[[[3-(4-aminobutoxy)phenyl]sulfonyl]amino]benzene-propanoic acid, ethyl ester, monohydrochloride

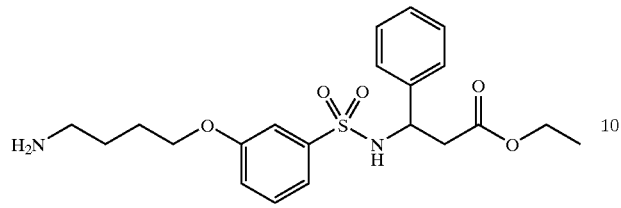

To a solution of ethyl β-[[(3-hydroxyphenyl)sulfonyl]amino]benzenepropanoate (1 g, 2.86 mmol) and PPh₃ polymer (1 g, ~3 mmol PPh₃/g resin) in dry THF (10 mL) was added 4-(BOC-amino)-1-butanol (0.54 g , 2.86 mmol) and diisopropyl azodicarboxylate (0.85 ml, 4.3 mmol) at room temperature. The mixture was stirred at room temperature for 24 hours. Solid was filtered out. Filtrate was concentrated then treated with 4 N HCl in dioxane (10 mL). After 3 hours, the mixture was concentrated under reduced pessure. The residue was purified on reverse phase HPLC to give the title compound (0.6 g, 39%). MS (ES) m/e 421.24 (M+H)⁺. NMR (400 MHz, CD₃OD) δ 7.22–7.28 (m, 2 H), 7.06–7.14 (m, 6 H), 6.96–6.98 (m, 1 H), 4.75 (t, 1 H, J=7.56 Hz), 3.95–4.01 (m, 2H), 3.92 (t, 2H, J=5.51 Hz), 2.99 (t, 2H, J=6.66 Hz), 2.64–2.78 (m, 2H), 1.81–1.85 (m, 4 H), 1.12 ((t, 3 H, J=7.18 Hz).

Step 2

β-[[[3-[4-[(1,4,5,6-tetrahydro-2-pyrimidinyl)amino]butoxy]phenyl]sulfonyl]amino]benzenepropanoic acid To 2-methylthio-2-pyrimidin hydroiodide (0.58 g, 2.2 mmol) and β-[[[3-(4-aminobutoxy)phenyl]sulfonyl]amino]benzenepropanoic acid, ethyl ester, monohydrochloride (0.6 g, 1.1 mmol) in DMF (5 mL) was added triethylamine (0.34 g, 3.4 mmol). The reaction was refluxed overnight. The solution was concentrated and purified on reverse phase HPLC to give ethyl ester (0.19 g, 14%) of the title compound. The ethyl ester was dissolved in 50% acetonitrile in water (4 mL) and treated with LiOH (90 mg). The reaction was stirred at room temperature for 3 hours then purified on reverse phase HPLC to give TFA salt (40 mg, 22%) of the title compound. HRMS: (MH+)=475.2002. NMR (400 MHz, DMSO/TFA) δ 1.55–160 (m, 2 H), 1.64–1.69 (m, 2 H), 1.74–1.77 (m, 2 H), 2.48–2.61 (m, 2 H), 3.08 (q, 2H, J=6.51 Hz), 3.18–3.20 (m, 4 H) 3.83 (t, 2H, J=6.17 Hz), 4.59–4.61 (m, 1 H), 6.85–6.95 (m, 2 H), 7.01–7.24 (m, 8 H), 7.62 (bs, 2 H), 8.25 (d, 1 H, J=8.73 Hz).

EXAMPLE 31

3-[[[3-[4-[(2-pyridinylamino)butoxy]phenyl]sulfonyl]amino]-3-butanoic acid

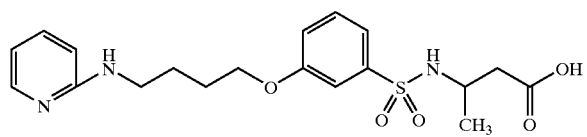

Step 1

3-[[(3-methoxyphenyl)sulfonyl]amino]-butanoic acid, ethyl ester

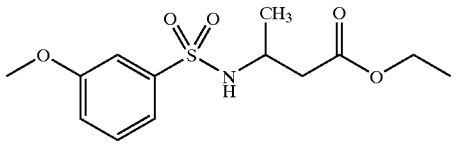

To a solution of 3-Methoxybenzynesulfonyl chloride (4.94 g, 23.9 mmol) and ethyl-3-aminobutylate (3.29 g, 25 mmol) in DMF (50 ml) was added triethylamine (3.5 ml, 25 mmol) at room temperature. The reaction mixture was stirred 48 hours at room temperature. Solid was filtered and washed with DMF. Filtrate was concentrated and brought up to ethylacetate (300 ml). The organic solution was washed with 5% citric acid, water and brine. The organic solution was dried over Na₂SO₄ and concentrated to dryness to give the title compound (8 g). The concentrated residue was used without further purification. ¹H NMR (400 MHz, CDCL₃) δ 1.140 ((d, 3H, J=6.66 Hz), 1.20 (t, 3H, J=7.05 Hz), 2.39 (d, 2H, J=5.38 Hz), 3.65–3.74 (m, 1H), 3.84 (s, 3H), 4.01–4.13 (m, 2H), 5.28 (d, 1H, J=8.23 Hz), 7.05–7.08 (m, 1H), 7.37–7.45 (m, 3 H).

Step 2

3-[[(3-hydroxyphenyl)sulfonyl]amino]-butanoic acid, ethyl ester

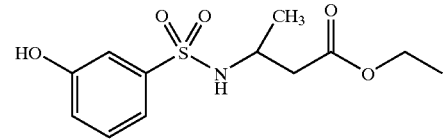

A mixture of β-[[(3-methoxypheyl)sulfonyl]amino]-butanoic acid, ethyl ester (7.8 g, 25.7 mmol) and ethanethiol (8 g, 0.13 mol) in methylenechloride (200 ml) was cooled in ice-bath. Aluminum chloride (17.2 g, 0.13 mol) was added to above soultion. The reaction mixture was stirred at room temperature for 4 hours. The reaction mixture was quenched with 3N HCl (200 ml). Organic layer was separated. Aqueous layer was extracted with methylene chloride (2×100 ml). Combined organic solution was concentrated and dried to give the title compound (7 g, 94%). The material was used for the next reaction without further purification. ¹H NMR (300 MHz, CD₃OD) □|□d, 3H, J=6.73 Hz), 1.23 (t, 3H, J=7.11 Hz), 2.31–2.49 (m, 2H), 3.66–3.74 (m, 1H), 4.01–4.16 (m, 2H), 7.00–7.04 (m, 1H), 7.27–7.41 (m, 3H).

Step 3

3-[[[3-[4-[(1-oxido-2-pyridinyl)amino]butoxy]phenyl]sulfonyl]amino]-3-butanoic acid, ethyl ester

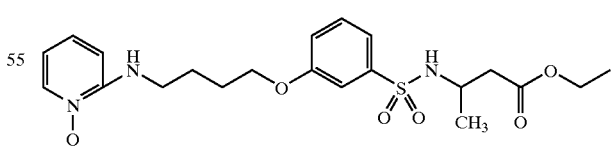

To a solution of β-[[(3-methoxypheyl)sulfonyl]amino]butanoic acid, ethyl ester (1 g, 3.4 mmol) and triphenylphosphine (0.9 g, 3.4 mmol) in DMF (10 ml) was added 2-[(3-Hydroxy-1-propyl)amino]pyridine-N-oxide (0.63 g, 3.4 mmol) followed by diethyl azodicarboxylate (0.6 g, 3.4 mmol) at room temperature. The reaction mixture was stirred 4 hours at room temperature. The crude reaction mixture was purified on reverse phase HPLC to give the TFA salt of the title compound (0.74 g, 49%). $^1$H NMR (300 MHz, CD$_3$OD) δ 1.06 (d, 3H, J=6.73 Hz), 1.21 (t, 3H, J=7.11 Hz), 1.89–1.98 (m, 4H), 2.32–2.49 (m, 2H), 3.51 (t, 2H, J=6.63 Hz), 3.66–3.73 (m,1 H), 3.99–4.08 (m, 2 H), 4.14 (t, 2 H, J=5.76 Hz), 6.76–6.81 (m, 1 H), 7.06–7.10 (m, 1H), 7.16–7.20 (m, 1H), 7.38–7.51 (m, 3 H), 7.59–7.65 (m, 1 H), 8.13–8.16 (m, 1H).

Step 4

3-[[[3-[4-[(2-pyridinylamino)butoxy]phenyl]sulfonyl]amino]-3-butanoic acid

To a solution of 3-[[[3-[4-[(1-oxido-2-pyridinyl)amino]butoxy]phenyl]sulfonyl]amino]-3-butanoic acid, ethyl ester (0.64 g, 0.15 mmol) in ethanol (10 ml) was added 5% Pd/C (0.4 g) and cyclohexene (2 ml). The reaction mixture was heated at 70° C. for 18 hours. Pd/C was filtered through celite and the filtrate was concentrated under reduced vacuum. The concentrated residue was dissolved in 2 ml of 1:1/acetonitrile:water with lithium hydroxide (0.18 g). The mixture was stirred at room temperature for 3 hours then purified on reverse phase HPLC to give the TFA salt of the title compound (0.3 g, 39%). $^1$H NMR (400 MHz, CD$_3$OD) δ 1.03 (δ, 3H, J=6.66 Hz), 1.89–2.01 (m, 4H), 2.24–2.45 (m, 2H), 3.42 (t, 2H, J=6.66 Hz), 3.60–3.65 (m,1 H), 4.12 (t, 2 H, J=5.64 Hz), 6.86(t, 1 H, J=6.66 Hz), 7.03(d, 1H, J=9.23 Hz), 7.12–7.15 (m, 1H), 7.35–7.47(m, 3 H), 7.79–7.80 (d, 1 H, J=6.41 Hz), 7.84–7.89 (m, 1 H). HRMS (M+H) calculated for C$_{19}$H$_{25}$N$_3$O$_5$S$_1$ 408.1593, found 408.1580.

EXAMPLE 32

3-[[[3-[4-[(1,4,5,6-tetrahydro-2-pyrimidinyl)amino]butoxy]phenyl]sulfonyl]amino]butanoic acid

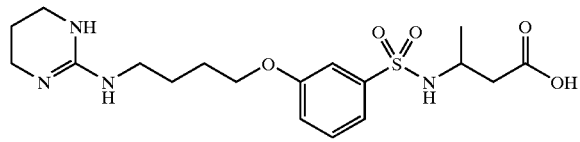

β-[[[3-(4-aminobutoxy)phenyl]sulfonyl]amino]butanoic acid, ethyl ester

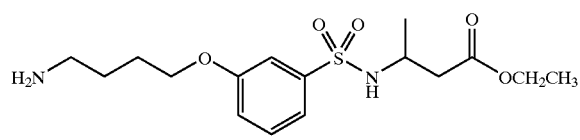

The above compound was prepared according to methodologh of example 3-F, substituting an equivalent amount of β-[[(3-hydroxyphenyl)sulfonyl]amino]butanoate for β-[[(3-hydroxyphenyl)sulfonyl]amino]benzenepropanoate. This afforded a TFA salt of the title compound (62%).

Step 2

3-[[[3-[4-[(1,4,5,6-tetrahydro-2-pyrimidinyl)amino]butoxy]phenyl]sulfonyl]amino]butanoic acid The title compound was prepared according to methodology of EXAMPLE 21, substituting an equivalent amount of β-[[[3-(4-aminobutoxy)phenyl]sulfonyl]amino]butanoic acid ethyl ester, monohydrochloride for ethyl β-[[(3-hydroxyphenyl)sulfonyl]amino]benzenepropanoate. $^1$H NMR (300 MHz, CD$_3$OD) δ 1.88 (bs, 4 H), 2.51–2.68 (m, 2 H), 2.72–2.80 (m, 1 H), 2.96–3.02 (m, 1H), 3.43 (bs, 2 H), 3.83–3.94 (m, 3 H), 6.74–6.77 (m, 1H), 6.87–6.90 (m, 1H), 6.92–7.17 (m, 5 H), 7.41–7.47 (m, 3 H), 7.59 (d, 1 H, J=8.45 Hz), 7.67–7.70 (m, 1 H), 7.75–7.81 (m, 1 H), 7.84–7.87 (m, 1 H), 7.90–7.93 (m, 1 H), HRMS (M+H) calculated for C$_{29}$H$_{31}$N$_3$O$_5$S$_1$ 534.2063, found 534.2065.

EXAMPLE 33

(3S)-3-[[[3-[4-(2-pyridinylamino)butoxy]phenyl]sulfonyl]amino]-5-hexynoic acid

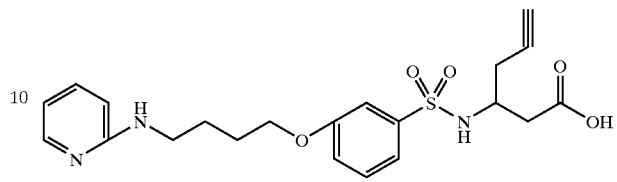

Step 1

3-amino-5-hexynoic acid, ethyl ester, monohydrochloride

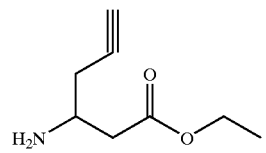

(S)-3-amino-5-hexynoic acid (1 g, 7.87 mmol) was dissolved in saturated HCl in ethanol (20 mL). The reaction mixture was stirred at room temperature overnight and concentrated under reduced pressure. Dried to give HCl salt of the title compound (1.5 g, 99%). NMR (400 MHz, CD$_3$OD) δ 1.22 (t, 3 H, J=7.18 Hz), 2.63–2.68 (m, 3H), 2.70–2.89 (m, 2H), 3.69–3.75 (m, 1H), 4.17–4.22 (m, 2 H).

Step 2

(3S)-3-[[(3-methoxyphenyl)sulfonyl]amino]-5-hexynoic acid, ethyl ester

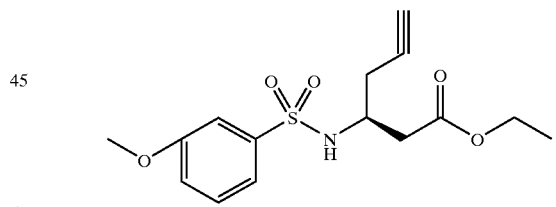

To a solution of 3-methoxybenzensulfonyl chloride (1.1 g, 5.2 mmol) and (S)-ethyl-3-amino-5-hexynoic ester (1 g, 5.2 mmol) in dry DMF (15 mL) was added triethylamine (1.4 mL, 10.3 mmol) at room temperature. The mixture was stirred at room temperature for 24 hours. DMF was removed under reduced pressure. The concentrated residue was brought up to ethyl acetate (150 mL) and washed with 5% citric acid (100 mL). The organic layer was separated and concentrated. The residue was purified by column chromatography (30% ethyl acetate in hexane) to give the title compound (1.6 g, 92.5%). FB$^+$=326.4 (M+H)$^+$. NMR (400 MHz, CD$_3$OD) δ 1.16 (t, 3 H, J=7.05 Hz), 1.22 (t, 1 H, J=7.05 Hz), 1.99–2.35 (m, 2H), 2.39–2.66 (m, 2H), 3.71–3.78 (m, 1H), 3.85 (s, 3H), 3.89–4.00 (m, 2H), 7.13–7.16 (m, 1 H), 7.36–7.46 (m, 3 H).

Step 3
(3S)-3-[[(3-hydroxyphenyl)sulfonyl]amino]-5-hexynoic acid, ethyl ester

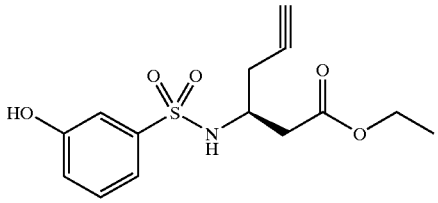

To a solution of methoxybenzensulfoamide (0.8 g, 2.5 mmol) in methylenechloride (20 mL) and ethane thiol (0.76 g, 12.3 mmol) in methylenechloride (20 mL) was added aluminum chloride (1.63 g, 12.2 mmol) at 0° C. The mixture was allowed to warm to RT and stirred at RT for 3 hours. The mixture was quenched with 3 N HCl (20 mL) at 0° C. slowly. The solution was extracted with methylenechloride (2×30 mL). Combined organic solution was washed with brine, dried over MgSO4 and concentrated to give the title compound (0.71 g). Compound was used for coupling reaction without further purification.

Step 4
(3S)-3-[[[3-[4-[(1-oxido-2-pyridinyl)amino]butoxy]phenyl]sulfonyl]amino]-5-hexynoic acid, ethyl ester

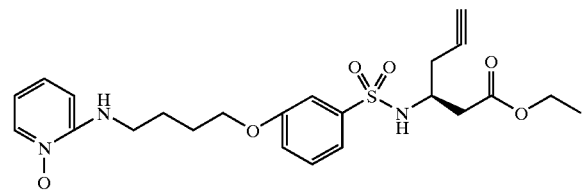

The hydroxyphenylsulfonamide compound (0.7 g, 2.2 mmol) and triphenylphosphine polymer 0.3 mmol per g (1.35 g) were dissolved in THF (10 ml). 2-[(3-Hydroxy-1-propyl)amino]pyridine-N-oxide (0.74 g, 4.06 mmol) and diethyl azodicarboxylate (0.8 mL, 4.06 mmol) were added to above solution at room temperature. The reaction mixture was stirred 48 hours at room temperature. Solid was filtered out and filtrate was concentrated. The residue was purified on reversed phase HPLC to give the title compound (0.6 g, 45%). $^1$H NMR (400 MHz, CD$_3$OD) δ 1.45 (t, 3H, J=7.18 Hz), 1.84–2.01 (m, 4H), 2.28–2.39 (m, 3 H), 2.41–2.65 (m, 2 H), 3.50 (t, 2 H, J=6.79 Hz), 3.71–3.90 (m, 1 H), 3.91–4.00 (m, 2H), 4.11 (t, 2 H, J=5.71 Hz), 6.79–6.83 (m, 1H), 7.13–7.18 (m, 2H), 7.35–7.40 (m,1 H), 7.40–7.46 (m, 2 H), 7.71–7.76 (m, 1 H), 8.15–8.18 (m, 1 H). HRMS (M+H) calculated for C$_{23}$H$_{29}$N$_3$O$_6$S$_1$ 476.1855, found 476.1830.

Step 5
(3S)-3-[[[3-[4-(2-pyridinylamino)butoxy]phenyl]sulfonyl]amino]-5-hexynoic acid, ethyl ester

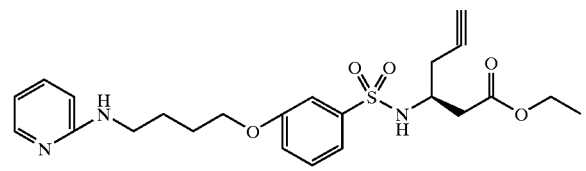

A mixture of N-oxide compound (0.2 g, 0.35 mmol), PPh3 (92 mg, 0.35 mmol) and iron (29 mg, 0.52 mmol) in acetic acid (8 mL) was refluxed for 2 hours. Iron was filtered out. Filtrate was concentrated. The concentrated residue was purified on reverse phase HPLC to give the title compound (30 mg, 16%). $^1$H NMR (300 MHz, CD$_3$OD) δ 1.16 (t, 3H, J=7.10 Hz), 1.94 (m, 4H), 2.29–2.67(m, 5 H), 3,44 (t, 2 H, J=6.51 Hz), 3.75 (t, 1 H, J=6.44 Hz), 3.90–4.03 (m, 2 H), 4.14 (t, 2H, J=5.56 Hz), 6.88 (t, 1H, J=6.73 Hz), 7.03 (d, 1H, J=9.08 Hz), 7.13–7.17 (m,1 H), 7.36 (d, 1 H, J=1.76 Hz), 7.41–7.48 (m, 2 H), 7.81 (d, 1 H, J=5.71 Hz), 7.85–7.91 (m, 1 H). HRMS (M+H) calculated for C$_{23}$H$_{29}$N$_3$O$_5$S$_1$ 460.1906, found 460.1905.

Step 6
(3S)-3-[[[3-[4-(2-pyridinylamino)butoxy]phenyl]sulfonyl]amino]-5-hexynoic acid To a solution of ethyl ester (30 mg, 0.04 mmol) of title compound in 30% water in acetonitrile (3 mL) was added LiOH (40 mg). The mixture was stirred one hour at room temperature. The solution was acidified by adding TFA in water then purified on reverse phase HPLC to give the TFA salt of the title compound (20 mg, 83%). $^1$H NMR (400 MHz, CD$_3$OD) □ 1.89–1.96 (m, 4H), 2.26 (t, 1 H, J=2.69 Hz), 2.35 (dd, 2 H, J=2.82 Hz), 2.38–2.62 (m, 2 H), 3.42 (t, 2 H, J=6.66 Hz), 3.71 (t, 1 H, J=6.28 Hz), 4.12 (t, 2H, J=5.77 Hz), 6.84–6.88 (m, 1H), 7.03 (d, 1H, J=9.22 Hz), 7.12–7.15 (m,1 H), 7.36–7.37 (m, 1 H), 7.41–7.44 (m, 2 H), 7.79 (d, 1 H, J=6.41 Hz), 7.85–7.89 (m, 1 H). HRMS (M+H) calculated for C$_{21}$H$_{25}$N$_3$O$_5$S$_1$ 432.1593, found 432.1581.

EXAMPLE 34

β-[[[3-[[5-(2-pyridinylamino)pentyl]oxy]phenyl]sulfonyl]amino]benzene-propanoic acid

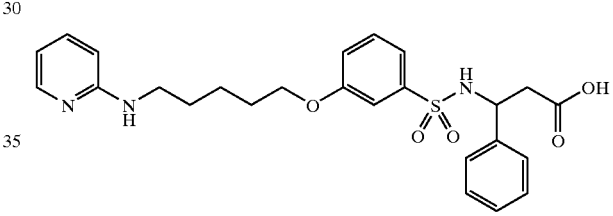

The title compound was prepared according to methodology of EXAMPLE 21, substituting an equivalent amount of 2-aminopyridine-pentanol for 2-aminopyridinebutanol to give the TFA salt of the title compound. $^1$H NMR (400 MHz, CD$_3$OD) δ 1.59–1.65 (m, 2H), 1.74–1.92 (m, 4 H), 2.62–2.77 (m, 2 H), 3.37 (t, 2 H, J=7.05 Hz), 3.92 (t, 2 H, J=6.15 Hz), 4.74 (t, 1H, J=7.43 Hz), 6.83–6.86 (m, 1H), 6.94–6.97 (d, 1H), 7.05–7.09 (m,7 H), 7.11–7.26 (m, 2 H), 7.78 (d, 1 H, J=6.41 Hz), 7.86 (t, 1 H, J=8.07 Hz). HRMS (M+H) calculated for C$_{25}$H$_{29}$N$_3$O$_5$S$_1$ 484,1906, found 494.1900.

EXAMPLE 35

(β$^2$S)-β-[[[3-[4-(2-pyridinylamino)butoxy]phenyl]sulfonyl]amino]-2-naphthalenebutanoic acid

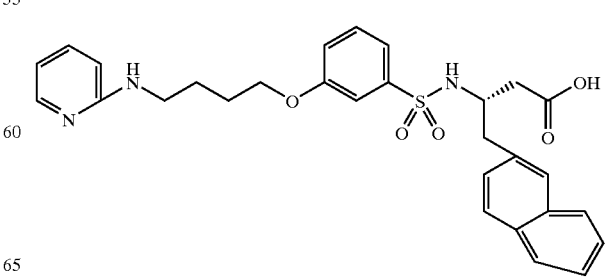

Step 1

(S)-ethyl-3-amino-4-(2-naphthyl)-butyrate, monohydrochloride

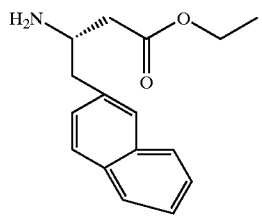

(S)-3-amino-4-(2-naphthyl)butyric acid (1 g, 4.4 moles) was dissolved in saturated HCl in ethanol (20 ml). The mixture was stirred for 4 hours at room temperature under nitrogen. Solution was concentrated under vacuum. Concentrated residue was triturated with ethyl acetate. Ethyl acetate was removed and the procedure was repeated twice. Dried under high vacuum to give the HCl salt of the title compound (1.2 g) as a white solid. $^1$H NMR (400 MHz, CD$_3$OD) δ 1.2(t, 3 H, J=7.18 Hz), 2.60–2.76 (m, 2 H), 3.07–3.20 (m, 2 H), 3.90–3.96 (m, 1 H), 4.02–4.14 (m, 2 H), 7.37–7.40 (m, 1 H), 7.45–7.51 (m, 2 H), 7.74 (s, 1 H), 7.82–7.89 (m, 3 H). HRMS (M+H) calculated for $C_{16}H_{19}N_1O_2$ 258.1494, found 258.1500.

Step 2

(3S)-3-[[3-(hydroxyphenyl)sulfonyl]amino]-2-naphthalenebutyric acid, ethyl ester

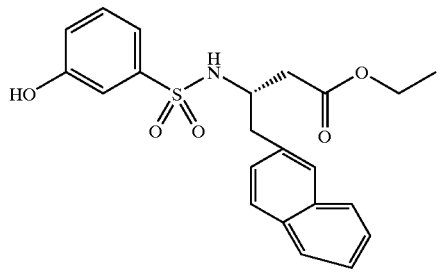

To a solution of 3-Methoxybenzynesulfonyl chloride (1.2 g, 3.9 mmol) and (S)-ethyl-3-amino-4-(2-naphthyl)-butyrate, monohydrochloride (1.15 g, 3.9 mmol) in DMF (10 ml) was added triethylamine (0.79 g, 7.8 mmol) at room temperature. The reaction mixture was stirred 18 hours at room temperature. Solid was filtered and washed with DMF. The filtrate was concentrated to dryness to leave brown oil (1.75 g). A solution of the above material (1.5 g, 3.5 mmol) in CH$_2$CL$_2$ (20 ml) was added ethanethiol (1.1 g, 17 mmol) followed by AlCl$_3$ (2.34 g, 17 mmol) at 0° C. The reaction mixture was warmed up to room temperature. After 5 hours, the mixture was quenched with 3 N HCl (50 ml) at 0° C. Organic layer was separated. Aqueous layer was extracted with methylene chloride (100 ml). Combined organic solution was concentrated and dried to give the title compound (1.8 g). The material was used for the next reaction without further purification. $^1$H NMR (300 MHz, CD$_3$OD) δ (1.2, t, 3H, J=7.11 Hz), 2.5 (d, 2H, J=6.53 Hz), 2.79–2.95 (m, 2H), 3.92–4.07 (m, 3H), 6.73–6.77 (m, 1H), 6.98–7.07 (m, 2H), 7.12–7.13 (m, 1H), 7.19–7.22 (m, 1 H), 7.41–7.50 (m, 3 H), 7.68–7.82 (m, 3 H). MS (ES) m/e 414.06 (M +H)$^+$.

Step 3

(β$^2$S)-β-[[[3-[4-(1-oxido-2-pyridinylamino)butoxy]phenyl]sulfonyl]amino]-2-naphthalenebutanoic acid, ethyl ester

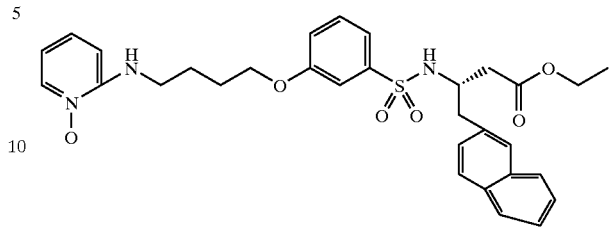

To a solution of (S)-ethyl β-[[3-(hydroxyphenyl)2-naphthalenebutyrate (0.5 g, 1.2 mmol) and triphenylphosphine polymer bound (0.5 g, 1.5 mmol) in THF (10 ml) was added 2-[(4-Hydroxy-1-butyl)amino]pyridine-N-oxide (0.27 g, 1.2 mmol)and azodicarboxylate (0.29 ml, 1.5 mmol) at room temperature. The reaction mixture was stirred at room temperature for 18 hours. Solid was filtered. The filtrate was concentrated and purified on reverse phase HPLC. Appropriate fractions were collected to give clear oil (0.21 g). NMR and mass spect are consistent with the structure.

Step 4

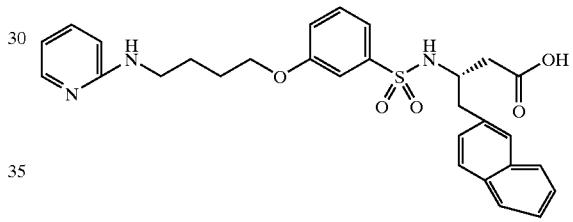

The above compound was prepared according to methodology of example 21, substituting an equivalent amount of (S)-ethyl β-[[3-(hydroxyphenyl)2-naphthalenebutyrate for ethyl β-[[(3-(hydroxypheyl)sulfonyl]amino] benzenepropanoate to give the TFA salt of the title compound. $^1$H NMR (300 MHz, CD$_3$OD) δ 1.88 (bs, 4 H), 2.51–2.68 (m, 2 H), 2.72–2.80 (m, 1 H), 2.96–3.02 (m, 1 H), 3.43 (bs, 2 H), 3.83–3.94 (m, 3 H), 6.74–6.77 (m, 1H), 6.87–6.90 (m, 1H), 6.92–7.17 (m,5 H), 7.41–7.47 (m, 3 H), 7.59 (d, 1 H, J=8.45 Hz), 7.67–7.70 (m, 1 H), 7.75–7.81 (m, 1 H), 7.84–7.87 (m, 1 H), 7.90–7.93 (m, 1 H). HRMS (M+H) calculated for $C_{29}H_{31}N_3O_5S_1$ 534.2063, found 534.2065.

EXAMPLE 36

(S) 3-[(3,5-dichloro-2-hydroxyphenyl)-3-(3-methoxyphenylsulfonylamino)]propionic acid

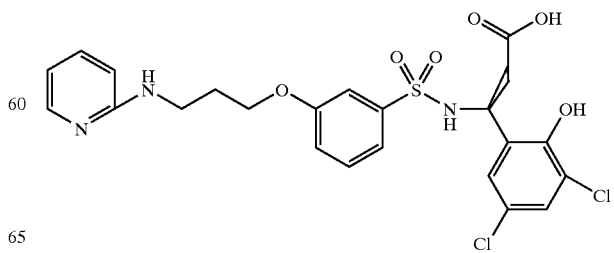

Step 1

(S) 3-[(3,5-dichloro-2-hydroxyphenyl)-3-(3-methoxyphenylsulfonylamino)]propionic acid ethyl ester

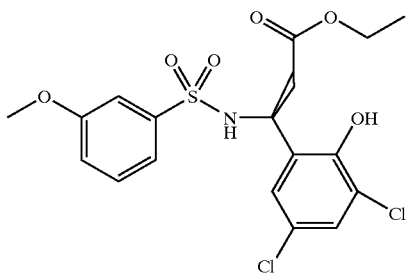

3-Methoxybenzenesulfonylchloride (2.21 g, 0.01 mol) and 3-(s)-amino-3-(2-hydroxy-3,5-dichloro)phenyl-propionic acid ethyl ester p-toluene sulfonate salt (4.68 g, 0.01 mol) were dissolved in DMA (30 mL). Triethyl amine (2.8 mL, 0.02 mol) was added. The reaction mixture was stirred 3 hours at room temperature and triethyl amine (1.4 mL, 0.01 mol) was added. The reaction was stirred 18 hours at room temperature. The reaction mixture was concentrated under reduced pressure. The concentrated residue was purified by 18C reverse phased HPLC to give the desired compound (0.8 g, 17.8% yield). The structure was confirmed by NMR.

Step 2

(S) 3-[(3,5-dichloro-2-hydroxyphenyl)-3-(3-methoxyphenylsulfonylamino)]propionic acid

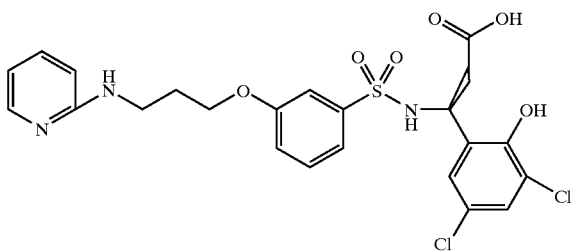

The compound is prepared using the methods described in Example 7.

EXAMPLE 37

3-Pheny-4-[3-{3-(pyridin-2-yl)amino-1-propyloxy}phenyl] butanoic acid

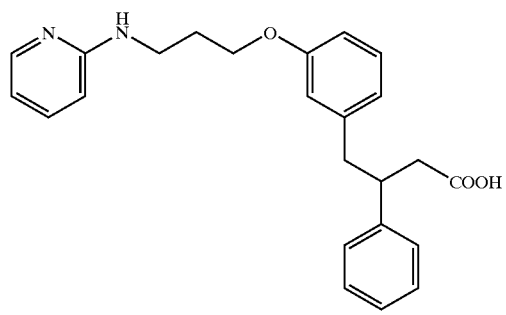

Step 1 m-Methoxybenzyl phenyl ketone

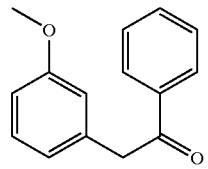

A mixture of m-anisaldehyde (29.37 g, 21.57 mmol) and phenylacetic acid (29.37 g, 21.57 mmol) in acetic anhydride (200 mL) was stirred with triethylamine (30 mL). The reaction mixture was heated at reflux for 4 h, then cooled to 80–90° C., then water (500 mL) was added slowly. Oil separated, which upon stirring and cooling produced a light orange solid. The solid was filtered, washed with water and dried to afford 35 g (64%) of the desired 2-phenyl-m-methoxycinnamic acid. Triethylamine (17 mL) was added to a mixture of 2-phenyl-m-methoxycinnamic acid (30.0 g, 118.0 mmol) and diphenylphosphorylazide (28 mL) in toluene (200 mL) at 0° C. After the reaction had been complete (3 h), the reaction mixture was quenched with concentrated HCl (20 mL) and extracted with ether (200 mL). The organic layer was concentrated and the residue was stirred further with Conc. HCl (100 mL) and dioxane (100 mL) for 24 h. The reaction mixture was diluted with water (400 mL) and was extracted with ether (3×300 mL). The ether layer was dried and concentrated to afford 10 g (38%) of the desired product. $^1$H NMR (CDCl$_3$) δ 7.99–8.01 (m, 2H), 7.42–7.54 (m, 5H), 6.77–6.85 (m, 3H), 4.24 (s, 2H), 3.77 (s, 3H).

Step 2

Ethyl 4-(m-methoxyphenyl)-3-phenyl-3-hydroxybutyrate

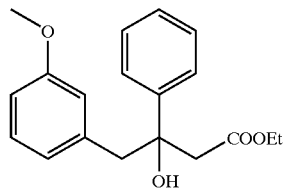

Lithium hexamethyldisilazane (88.5 mL, 88.5 mmol) was added to THF (150 mL) at −78° C. After 15 min, ethyl acetate (7.79 g, 88.5 mmol) was added over 10 min and stirred at −78° C. for 30 min. The m-methoxybenzyl phenyl ketone in (10.0 g, 44.25 mmol) THF (100 mL) was added over 15 min and kept at that temperature for 3 h. The reaction mixture was quenched at that temperature with saturated ammonium chloride (15 mL). The reaction mixture was diluted with ether (200 mL) and the organic layer was washed with brine, (100 mL), dried and was concentrated to afford 12 g (86%) of the desired product. $^1$H NMR (CDCl$_3$) δ 7.10–7.37 (m, 6H), 6.71–6.74 (m, 1 H), 6.60–6.62 (m, 1 H), 6.48 (s, 1 H), 3.95–4.00 (m, 2H), 3.67 (s, 3H), 2.72–3.07 (m, 4H), 1.06 (m, 3H).

Step 3

Ethyl 4-(m-methoxyphenyl)-3-phenylbutyrate

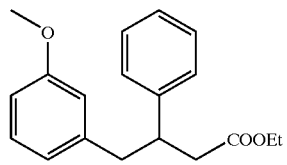

A mixture of ethyl 4-(m-methoxyphenyl)-3-phenyl-3-hydroxybutyrate (4.39 g, 13.98 mmol), palladium/carbon (10%, 2.5 g) hydrochloric acid (1.2 mL) in acetic acid (150 mL) was subjected to hydrogenation (50 psi) for 24 h. The catalyst was filtered, and the filtrate was concentrated to afford 1.89 g (45%) of the desired product. $^1$H NMR (CDCl$_3$) □ 7.10–7.27 (m, 6H), 6.63–6.70 (m, 2H), 6.55 (s, 1H), 3.95—4.05 (m, 2H), 3.70 (s, 3H), 3.39 (m, 1H), 2.83–2.89 (m, 2H), 2.56–2.68 (m, 2H), 1.10 (m, 3H).

Step 4

Ethyl 4-(m-hydroxyphenyl)-3-phenylbutyrate

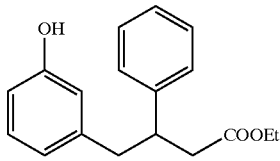

Aluminum chloride (4.1 g, 30.75 mmol) was added to a cooled solution of ethyl 4-(m-methoxyphenyl)-3-phenylbutyrate(1.83 g, 6.14 mmol) and ethyl mercaptan (2.3 mL) in dichloromethane (50 mL) at 0° C. After stirring for 3 h at room temperature. The reaction mixture was cooled to 0° C., and was slowly quenched with hydrochloric acid (3N, 50 mL). The reaction is very exothermic after an induction period of about 5 min. The organic layer was separated, washed with brine, dried and was concentrated. The residue was chromatographed (hexane:ethyl acetate, 3:1) to afford 1.56 g (90%) of the desired product as oil. $^1$H NMR (CDCl$_3$) δ 7.05–7.26 (m, 6H), 6.62 (m, 2H), 6.53 (s, 1H), 3.95–4.05 (m, 2H), 3.39 (m, 1H), 2.84–2.86 (m, 2H), 2.55–2.68 (m, 2H), 1.10 (m, 3H).

Step 5

Ethyl 3-pheny-4-[3-{3-(1-oxopyridin-2-yl)amino-1-propyloxy}phenyl]-butanoate

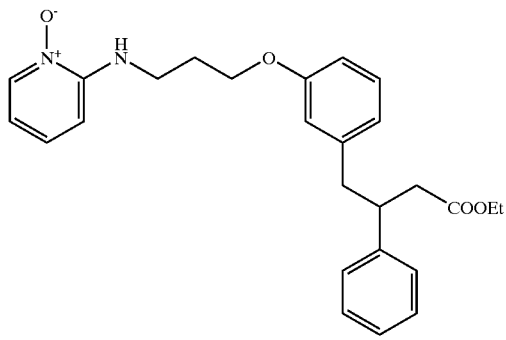

A solution of DEAD (1.91 g) and N-(2-pyridyl-N-oxide)-3-aminopropanol (1.84 g,) in DMF (10 mL) was added to a solution of ethyl 4-(m-hydroxyphenyl)-3-phenylbutyrate (1.56 g, 5.49 mmol) and triphenylphosphine (2.876 g) in DMF (15 mL) over a period of 5 min and the reaction mixture was stirred for 24 h. DMF was removed in vacuo and the residue was purified by hplc (reverse phase C18, 10%–100% gradient of acetonitrile in water containing 0.05% TFA) to afford 1.40 g (59%) of the desired product as oil. $^1$H NMR (CD$_3$OD) δ 8.16 (m, 1 H), 7.70 (m, 1 H), 7.05–7.21 (m, 7H), 6.80 (m, 1H), 6.63–6.69 (m, 2H), 6.58 (s, 1H), 3.89–3.98 (m, 2H), 3.59 (m, 1H), 3.28–3.34 9m, 2H), 2.83–2.87 (m, 2H), 2.61 (m, 2H), 2.07 (m, 2H), 1.04 (t, 3H, J=7.0 Hz).

Step 6

3-Pheny-4-[3-{3-(pyridin-2-yl)amino-1-propyloxy}phenyl]butanoic acid

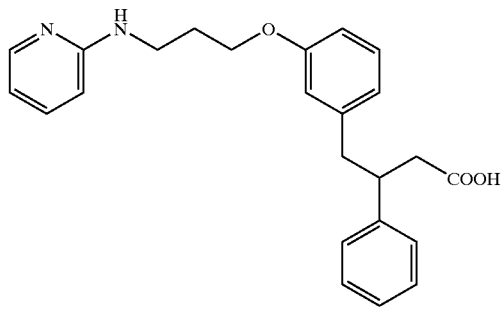

A mixture of ethyl 3-pheny-4-[3-{3-(1-oxopyridin-2-yl)amino-1-propyloxy}phenyl]butanoate (1.30 g, 2.98 mmol), palladium/C (0.30 g), cyclohexene (2.5 mL) in ethanol (25 mL) was heated at reflux over 24 h. The reaction mixture was filtered, and the residue was washed with additional amount of ethanol (100 mL). The combined filtrates were concentrated. The residue was added ethanol (5 mL) and sodium hydroxide (5 mL, 2.5 N) and stirred for 8 h. The reaction mixture was concentrated and the residue was dissolved in water (5 mL) and the pH was adjusted to 2 by the addition of TFA. This was purified by hplc (reverse phase C18, 10%–100% gradient of acetonitrile in water containing 0.05% TFA) and 0.90 g (71%) of the desired product was obtained as its HCl (after treatment with dil HCl) salt. $^1$H NMR (CD$_3$OD) δ 7.84–7.87 (m, 1 H), 7.83 (d, 1H, J=1.6 Hz), 7.02–7.22 (m, 7H), 6.84 (t, 1H, J=6.6 Hz), 6.66–6.69 (m, 1H), 6.62 (d, 1H, J=7.4 Hz), 6.56 (s, 1H), 3.98 (m, 2H), 3.54 (m, 1H), 2.86 (m, 2H), 2.6 (m, 2H), 2.11 (m, 2H). Anal. Calcd for C24H26N2O3: Mol. Wt, 391.2016 (M+H). Found: 391.2031 (M+H. HRMS).

The activity of the compounds of the present invention was tested in the following assays. Compounds of the present invention antagonize the $\alpha_v\beta_3$ integrin with an IC$_{50}$ of 0.1 nM to 100 μM in the 293-cell assay. Similarly these compounds also antagonized the $\alpha_v\beta_5$ integrin with an IC$_{50}$ of <50 μM in the cell adhesion assay.

Vitronectin Adhesion Assay

Materials

Human vitronectin receptors $\alpha_v\beta_3$ and $\alpha_v\beta_5$ were purified from human placenta as previously described [Pytela et al., *Methods in Enzymology*, 144:475–489 (1987)]. Human vitronectin was purified from fresh frozen plasma as previously described [Yatohgo et al., *Cell Structure and Function*, 13:281–292 (1988)]. Biotinylated human vitronectin was prepared by coupling NHS-biotin from Pierce Chemical Company (Rockford, Ill.) to purified vitronectin as previously described [Charo et al., *J. Biol. Chem.*, 266(3):1415–1421 (1991)]. Assay buffer, OPD substrate tablets, and RIA grade BSA were obtained from Sigma (St. Louis, Mo.). Anti-biotin antibody was obtained from Sigma (St. Louis, Mo.). Nalge Nunc-Immuno microtiter plates were obtained from Nalge Company (Rochester, N.Y.).

Methods

Solid Phase Receptor Assays

This assay was essentially the same as previously reported [Niiya et al., *Blood*, 70:475–483 (1987)]. The purified human vitronectin receptors $\alpha_v\beta_3$ and $\alpha_v\beta_5$ were diluted from stock solutions to 1.0 μg/mL in Tris-buffered saline containing 1.0 mM Ca$^{++}$, Mg$^{++}$, and Mn$^{++}$, pH 7.4 (TBS$^{+++}$). The diluted receptors were immediately transferred to Nalge Nunc-Immuno microtiter plates at 100 μl/well (100 ng receptor/well). The plates were sealed and incubated overnight at 4° C. to allow the receptors to bind to the wells. All remaining steps were at room temperature. The assay plates were emptied and 200 μL of 1% RIA grade BSA in TBS+++ (TBS+++/BSA) were added to block exposed plastic surfaces. Following a 2 hour incubation, the assay plates were washed with TBS+++ using a 96 well plate washer. Logarithmic serial dilution of the test compound and controls were made starting at a stock concentration of 2 mM and using 2 nM biotinylated vitronectin in TBS+++/BSA as the diluent. This premixing of labeled ligand with test (or control) ligand, and subsequent transfer of 50 μL aliquots to the assay plate was carried out with a CETUS Propette robot; the final concentration of the labeled ligand was 1 nM and the highest concentration of test compound was 1.0× $10^{-4}$ M. The competition occurred for two hours after which all wells were washed with a plate washer as before. Affinity purified horseradish peroxidase labeled goat anti-biotin antibody was diluted 1:2000 in TBS+++/BSA and 125 μL was added to each well. After 45 minutes, the plates were washed and incubated with OPD/$H_2O_2$ substrate in 100 mM/L Citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCEL spreadsheet program. The mean, standard deviation, and % CV were determined for duplicate concentrations. The mean $A_{450}$ values were normalized to the mean of four maximum-binding controls (no competitor added)(B-MAX). The normalized values were subjected to a four parameter curve fit algorithm [Rodbard et al., *Int. Atomic Energy Agency, Vienna*, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl] amino]-1-oxoethyl]amino]-3-pyridinepropanoic acid [U.S. Pat. No. 5,602,155 Example 1] which is a potent $α_vβ_3$ antagonist ($IC_{50}$ in the range 3–10 nM) was included on each plate as a positive control.

Purified IIb/IIIa Receptor Assay

Materials

Human fibrinogen receptor (IIb/IIIa) was purified from outdated platelets. (Pytela, R., Pierschbacher, M. D., Argraves, S., Suzuki, S., and Rouslahti, E. "Arginine-Glycine-Aspartic acid adhesion receptors", *Methods in Enzymology* 144(1987):475–489.) Human vitronectin was purified from fresh frozen plasma as described in Yatohgo, T., Izumi, M., Kashiwagi, H., and Hayashi, M., "Novel purification of vitronectin from human plasma by heparin affinity chromatography," *Cell Structure and Function* 13(1988):281–292. Biotinylated human vitronectin was prepared by coupling NHS-biotin from Pierce Chemical Company (Rockford, Ill.) to purified vitronectin as previously described. (Charo, I. F., Nannizzi, L., Phillips, D. R., Hsu, M. A., Scarborough, R. M., "Inhibition of fibrinogen binding to GP IIb/IIIa by a GP IIIa peptide", *J. Biol. Chem.* 266(3) (1991): 1415–1421.) Assay buffer, OPD substrate tablets, and RIA grade BSA were obtained from Sigma (St. Louis, Mo.). Anti-biotin antibody was obtained from Sigma (St. Louis, Mo.). Nalge Nunc-Immuno microtiter plates were obtained from (Rochester, N.Y.). ADP reagent was obtained from Sigma (St. Louis, Mo.).

Methods

Solid Phase Receptor Assays

This assay is essentially the same reported in Niiya, K., Hodson, E., Bader, R., Byers-Ward, V. Koziol, J. A., Plow, E. F. and Ruggeri, Z. M., "Increased surface expression of the membrane glycoprotein IIb/IIIa complex induced by platelet activation: Relationships to the binding of fibrinogen and platelet aggregation", *Blood* 70(1987):475–483. The purified human fibrinogen receptor (IIb/IIIa) was diluted from stock solutions to 1.0 μg/mL in Tris-buffered saline containing 1.0 mM $Ca^{++}$, $Mg^{++}$, and Mn++, pH 7.4 (TBS+++). The diluted receptor was immediately transferred to Nalge Nunc-Immuno microtiter plates at 100 μL/well (100 ng receptor/well). The plates were sealed and incubated overnight at 4° C. to allow the receptors to bind to the wells. All remaining steps were at room temperature. The assay plates were emptied and 200 μL of 1% RIA grade BSA in TBS+++ (TBS+++/BSA) were added to block exposed plastic surfaces. Following a 2 hour incubation, the assay plates were washed with TBS+++ using a 96 well plate washer. Logarithmic serial dilution of the test compound and controls were made starting at a stock concentration of 2 mM and using 2 nM biotinylated vitronectin in TBS+++/BSA as the diluent. This premixing of labeled ligand with test (or control) ligand, and subsequent transfer of 50 μL aliquots to the assay plate was carried out with a CETUS Propette robot; the final concentration of the labeled ligand was 1 nM and the highest concentration of test compound was 1.0× $10^{-4}$ M. The competition occurred for two hours after which all wells were washed with a plate washer as before. Affinity purified horseradish peroxidase labeled goat anti-biotin antibody was diluted 1:2000 in TBS+++/BSA and 125 μL were added to each well. After 45 minutes, the plates were washed and incubated with ODD/$H_2O_2$ substrate in 100 mM/L citrate buffer, pH 5.0. The plate was read with a microtiter plate reader at a wavelength of 450 nm and when the maximum-binding control wells reached an absorbance of about 1.0, the final $A_{450}$ were recorded for analysis. The data were analyzed using a macro written for use with the EXCELJ spreadsheet program. The mean, standard deviation, and % CV were determined for duplicate concentrations. The mean $A_{450}$ values were normalized to the mean of four maximum-binding controls (no competitor added)(B-MAX). The normalized values were subjected to a four parameter curve fit algorithm, [Robard et al., *Int. Atomic Energy Agency, Vienna*, pp 469 (1977)], plotted on a semi-log scale, and the computed concentration corresponding to inhibition of 50% of the maximum binding of biotinylated vitronectin ($IC_{50}$) and corresponding $R^2$ was reported for those compounds exhibiting greater than 50% inhibition at the highest concentration tested; otherwise the $IC_{50}$ is reported as being greater than the highest concentration tested. β-[[2-[[5-[(aminoiminomethyl)amino]-1-oxopentyl]amino]-1-oxoethyl]amino]-3-pyridinepropanoic acid [U.S. Pat. No. 5,602,155 Example 1] which is a potent $α_vβ_3$ antagonist ($IC_{50}$ in the range 3–10 nM) was included on each plate as a positive control.

Human Platelet Rich Plasma Assays

Healthy aspirin free donors were selected from a pool of volunteers. The harvesting of platelet rich plasma and subsequent ADP induced platelet aggregation assays were performed as described in Zucker, M. B., "Platelet Aggregation Measured by the Photometric Method", *Methods in Enzymology* 169(1989):117–133. Standard venipuncture techniques using a butterfly allowed the withdrawal of 45 mL of whole blood into a 60 mL syringe containing 5 mL of 3.8% trisodium citrate. Following thorough mixing in the syringe, the anti-coagulated whole blood was transferred to a 50 mL conical polyethylene tube. The blood was centrifuged at room temperature for 12 minutes at 200×g to sediment non-platelet cells. Platelet rich plasma was removed to a polyethylene tube and stored at room temperature until used. Platelet poor plasma was obtained from a second centrifugation of the remaining blood at 2000×g for 15 minutes. Platelet counts are typically 300,000 to 500,000 per microliter. Platelet rich plasma (0.45 mL) was aliquoted into siliconized cuvettes and stirred (1100 rpm) at 37° C. for 1 minute prior to adding 50 uL of pre-diluted test compound. After 1 minute of mixing, aggregation was initiated by the addition of 50 uL of 200 uM ADP. Aggregation was recorded for 3 minutes in a Payton dual channel aggregometer (Payton Scientific, Buffalo, N.Y.). The percent inhibition of maximal response (saline control) for a series of test compound dilutions was used to determine a dose response curve. All compounds were tested in duplicate and the concentration of half-maximal inhibition ($IC_{50}$) was calculated graphically from the dose response curve for those compounds which exhibited 50% or greater inhibition at the highest concentration tested; otherwise, the $IC_{50}$ is reported as being greater than the highest concentration tested.

What is claimed is:

1. A compound of the Formula:

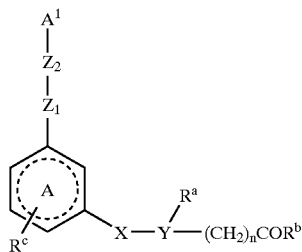

or a pharmaceutically acceptable salt thereof, wherein

is a phenyl ring, optionally substituted with one or more substituent selected from the group consisting of alkyl, haloalkyl, aryl, heteroaryl, halogen, alkoxyalkyl, aminoalkyl, hydroxy, nitro, alkoxy, hydroxyalkyl, thioalkyl, amino, alkylamino, arylamino, alkylsulfonamide, acyl, acylamino, sulfone, sulfonamide, allyl, alkenyl, methylenedioxy, ethylenedioxy, alkynyl, carboxamide, cyano, and —$(CH_2)_n$ COR wherein n is 0–2 and R is selected from the group consisting of hydroxy, alkoxy, alkyl and amino;

$A^1$ is a 5–9 membered monocyclic or 7–14 membered polycyclic heterocycle containing at least one nitrogen atom and optionally 1 to 4 heteroatoms or groups selected from O, N, S, $SO_2$ or CO; optionally saturated or unsaturated; optionally substituted by one or more $R^k$ selected from the group consisting of hydroxy, alkyl, alkoxy, alkoxyalkyl, thioalkyl, haloalkyl, cyano, amino, alkylamino, halogen, acylamino, sulfonamide and —COR wherein R is selected from hydroxy, alkoxy, alkyl and amino; or or $A^1$ is

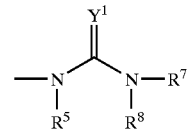

wherein $Y^1$ is selected from the group consisting of N—$R^2$, O, and S;

$R^2$ is selected from the group consisting of H; alkyl; aryl; hydroxy; alkoxy; cyano; alkenyl; alkynyl; amido; alkylcarbonyl; arylcarbonyl; alkoxycarbonyl; aryloxycarbonyl; haloalkylcarbonyl; haloalkoxycarbonyl; alkylthiocarbonyl; arylthiocarbonyl; acyloxymethoxycarbonyl;

$R^2$ taken together with $R^7$ forms a 4–12 membered dinitrogen containing heterocycle optionally substituted with one or more substituent selected from the group consisting of lower alkyl, thioalkyl, alkylamino, hydroxy, keto, alkoxy, halo, phenyl, amino, carboxyl or carboxyl ester, and fused phenyl;

$R^2$ taken together with $R^7$ forms a 5–9 membered heteroaromatic ring optionally substituted with one or more substituent selected from lower alkyl, phenyl, alkoxy and hydroxy;

$R^2$ taken together with $R^7$ forms a 5 membered heteroaromatic ring fused with a aryl or heteroaryl ring;

$R^7$ (when not taken together with $R^2$) and $R^8$ are independently selected from the group consisting of H; alkyl; alkenyl; alkynyl; aralkyl; amino; alkylamino; hydroxy; alkoxy; arylamino; amido, alkylcarbonyl, arylcarbonyl; alkoxycarbonyl; aryloxy; aryloxycarbonyl; haloalkylcarbonyl; haloalkoxycarbonyl; alkylthiocarbonyl; arylthiocarbonyl; acyloxymethoxycarbonyl; cycloalkyl; bicycloalkyl; aryl; acyl; benzoyl;

or $NR^7$ and $R^8$ taken together form a 4–12 membered mononitrogen containing monocyclic or bicyclic ring optionally substituted with one or more substituent selected from lower alkyl, carboxyl derivatives, aryl or hydroxy and wherein said ring optionally contains a heteroatom selected from the group consisting of O, N and S;

$R^5$ is selected from the group consisting of H and alkyl; or $A^1$ is

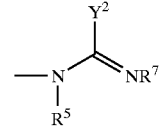

wherein $Y^2$ is selected from the group consisting of alkyl; cycloalkyl, bicycloalkyl; aryl; monocyclic heterocycles;

wherein $R^5$ and $R^7$ are defined above;

$Z_1$ is selected from the group consisting of $CH_2$, $CH_2O$, O, NH, CO, S, SO, CH(OH) and $SO_2$;

$Z_2$ is a 1–5 carbon linker optionally containing one or more heteroatom selected from the group consisting of O, S and N;

wherein the carbon and nitrogen atoms of $Z_1$–$Z_2$ are optionally substituted by a moiety selected from the group consisting of alkyl, alkoxy, thioalkyl, alkylsulfone, aryl, alkoxyalkyl, alkylamino, heteroaryl, alkenyl, alkynyl, carboxyalkyl, halogen, haloalky and acylamino;

n is an integer 0, 1 or 2;

$R^c$ is selected from the group consisting of hydrogen; alkyl; halogen, hydroxy, nitro, alkoxy, amino, haloalkyl, aryl, heteroaryl, alkoxyalkyl, aminoalkyl, hydroxyalkyl, thioalkyl, alkylamino, arylamino, alkylsulfonylamino, acyl, acylamino, sulfonyl, sulfonamide, allyl, alkenyl, methylenedioxy, ethylenedioxy, alkynyl, alkynylalkyl, carboxy, alkoxycarbonyl, carboxamido, cyano, and —$(CH_2)_n$COR wherein n is 0–2 and R is selected from hydroxy, alkoxy, alkyl and amino;

X is selected from the group consisting of —$CHR^e$—, —$NHR^f$—, —O—, —S—, —$SO_2$—, and CO wherein $R^e$ is selected from H, lower alkyl, alkoxy, cycloalkyl, alkoxyalkyl, hydroxy, alkynyl, alkenyl, haloalkyl, thioalkyl and aryl; wherein when $R^e$ is hydroxy the hydroxy optionally forms a lactone with the carboxylic acid function of the chain; wherein $R^f$ is selected from the group consisting of H, alkyl, aryl, benzyl and haloalkyl;

Y is selected from the group consisting of —$CR^g$— and —$N^g$— wherein $R^g$ is selected from the group consisting of H, alkyl, haloalkyl, alkoxyalkyl, alkynyl, aryl, heteroaryl, aralkyl, hydroxy, alkoxy, and carboxyalkyl;

$R^b$ is $X_2$—$R^h$ wherein $X_2$ is selected from the group consisting of O, S and $NR^j$ wherein $R^h$ and $R^j$ are independently selected from the group consisting of H, alkyl, aryl, aralkyl, acyl and alkoxyalkyl; and $R^a$ is selected from the group consisting of hydrogen, alkyl, alkenyl, alkoxyalkyl, hydroxyalkyl, alkynyl, alkynylalkyl, alkenylalkyl, haloalkyl, aryl, heteroaryl, aralkyl, heteroaralkyl, cycloalkyl, carboxyl, amino, alkylamine, alkoxycarbonyl, carboxamido, hydroxy, cyano, alkoxy, thioalkyl, acylamino, sulfonyl amino, alkylsulfonyl, and —$(CH_2)_n$ $COR^b$ wherein n is 0–2 and $R^b$ is as defined above.

2. The compound of claim 1, wherein $A^1$ is selected from the group consisting of:

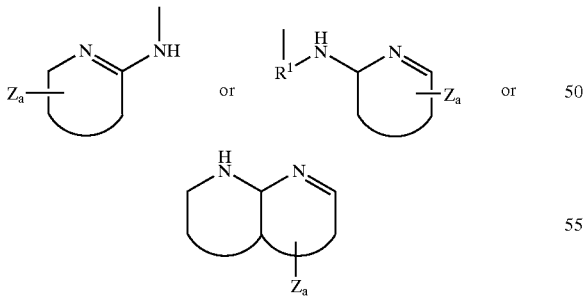

wherein $Z^a$ is selecting from the group consisting of H, alkyl, alkoxy, hydroxy, amine, alkylamine, dialkylamine, carboxyl, alkoxycarbonyl, hydroxyalkyl, halogen and haloalkyl; and $R^1$ is selected from the group consisting of H, alkyl, alkoxyalkyl, acyl, haloalkyl and alkoxycarbonyl.

3. A compound of claim 1 wherein $A^1$ is selected from the group consisting of:

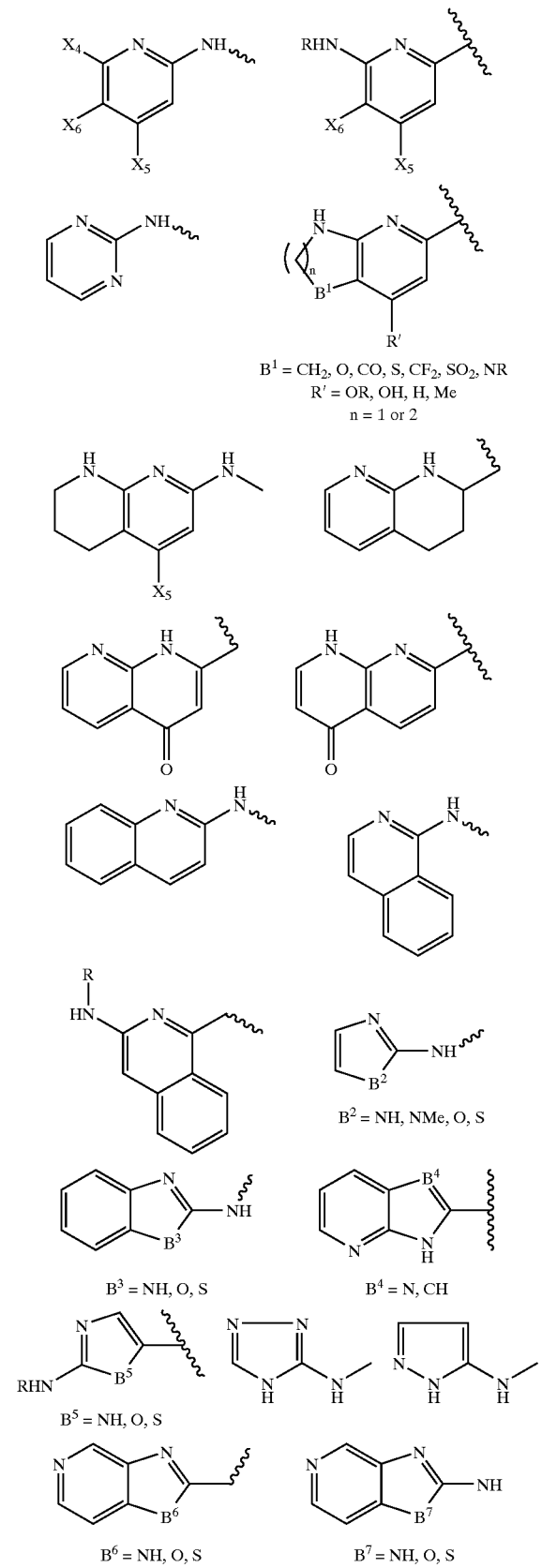

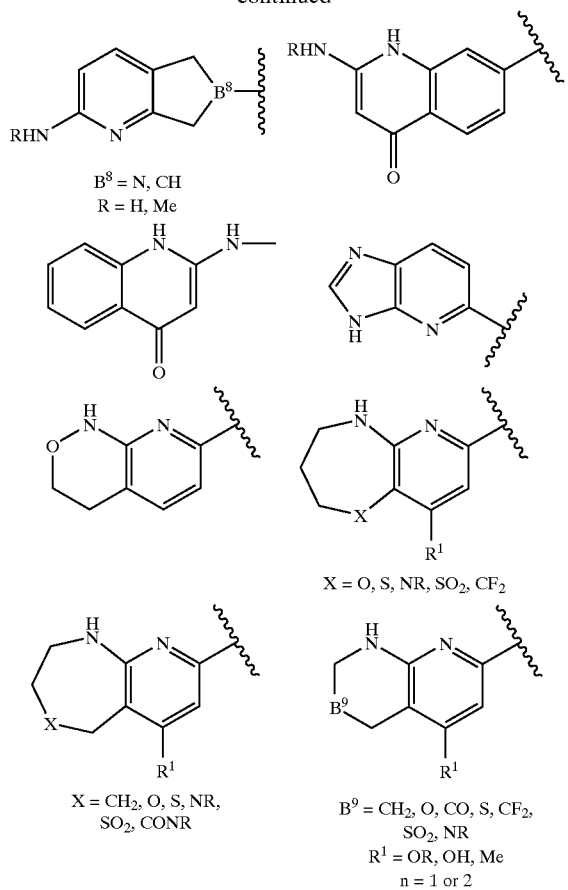
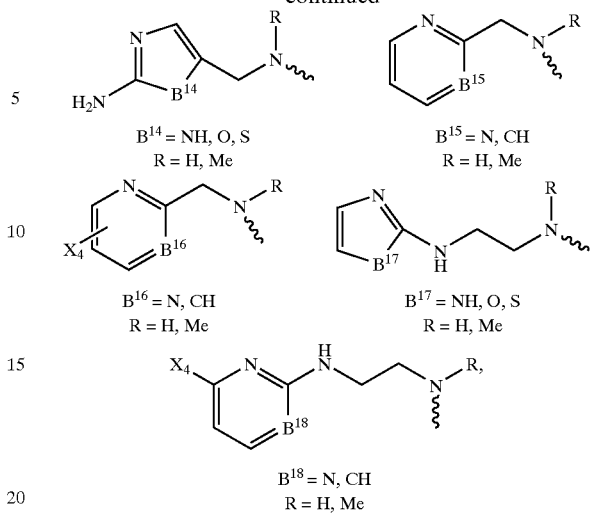

wherein
$X_4$ is selected from the group consisting of H, alkyl, branched alkyl, alkylamino, alkoxyalkylamino, haloalkyl, thioalkyl, halogen, amino, alkoxy, aryloxy, alkoxyalkyl, hydroxy, cyano and acylamino groups.

6. A compound according to claim 1 selected from the group consisting of

3-[[3-(2-pyridinylamino)propoxy]phenyl]propanoic acid;
3-[[4-(2-pyridinylamino)butoxy]phenyl]propanoic acid;
3-[[5-(2-pyridinylamino)pentoxy]phenyl]propanoic acid;
3-Phenyl-4-[3-[3-(pyridin-2-yl)amino-1-propyloxy]phenyl]butanoic acid;
3-[3-(2-pyridinylamino)propoxy]phenyl-3-methylbutanoic acid;
3-[4-(2-pyridinylamino)butoxy]phenyl-3-methylbutanoic acid;
β-[[[3-[3-(2-pyridinylamino)propoxy]phenyl]sulfonyl]amino]-benzenpropanoic acid;
β-[[[3-[4-(2-pyridinylamino)butoxy]phenyl]sulfonyl]amino]benzene propanoic acid;
3-[3-(2-pyridinyl)amino]-1-propyloxyphenylsulfonyl)-3-(3-pyridyl)aminopropanoic acid;
3-[4-(2-pyridinyl)amino]-1-butyloxyphenylsulfonyl)-3-(3-pyridyl)aminopropionic acid;
3-(4-(2-tetrahydropyrimidinyl)aminobutyloxyphenylsulfonyl)-3-(3-pyridyl)aminopropionic acid;
3-(4-(2-(5-hydroxy-tetrahydropyrimidinyl)aminobutyloxyphenyl-sulfonyl))-3-(3-pyridyl)aminopropionic acid;
3-[4-(2-pyridinyl)amino]-1-butyloxyphenylsulfonyl)-3-(3,5-dichloro-phenyl)aminopropionic acid;
3-[4-(2-pyridinyl)amino]-1-butyloxyphenylsulfonyl)-3-(3-pyridyl)aminopropionic acid;
3-[3-(2-pyridinyl)amino]-1-butyloxyphenyisulfonyl)-3-(phenethyl)-aminopropionic acid;
β-[[[3-[3-(2-pyridinylamino)butoxy]phenyl]sulfonyl]methyl]benzene-propanoic acid;
β-[[3-[3-(2-pyridinylamino)butoxy]phenyl]sulfonyl]methyl]4-fluorobenzenepropanoic acid;
N-({3-[4-(pyridin-2-ylamino)butoxy]phenyl}sulfonyl)-beta-alanine;
4-methyl-3-[({3-[4-(pyridin-2-ylamino)butoxy]phenyl}sulfonyl)amino]pentanoic acid;
3-cyclohexyl-3-[({3-[4-(pyridin-2-ylamino)butoxy]phenyl}sulfonyl)amino]propanoic acid;

3-(4-methylphenyl)-3-[({3-[4-(pyridin-2-ylamino)butoxy]
phenyl}sulfonyl)amino]propanoic acid;

β-[[[3-[4-[(1,4,5,6-tetrahydro-2-pyrimidinyl)amino]butoxy]
phenyl]-sulfonyl]amino]benzenepropanoic acid;

3-[[[3-[4-[(2-pyridinylamino)butoxy]phenyl]sulfonyl]
amino]-3-butanoic acid;

3-[[[3-[4-[(1,4,5,6-tetrahydro-2-pyrimidinyl)amino]butoxy]
phenyl]-sulfonyl]amino]butanoic acid;

(3S)-3-[[[[3-[4-(2-pyridinylamino)butoxy]phenyl]sulfonyl]
amino]-5-hexynoic acid;

β-[[[3-[[5-(2-pyridinylamino)pentyl]oxy]phenyl]sulfonyl]
amino]-benzenepropanoic acid;

($β^2$S)-☐-[[[3-[4-(2-pyridinylamino)butoxy]phenyl]
sulfonyl]amino]-2-naphthalenebutanoic acid;

(3S)-3-[({3-[4-(Pyridin-2-ylamino)butoxy]
phenyl}sulfonyl)amino]pent-4-ynoic acid;

(3S)-5-Phenyl-3-[({3-[4-(pyridin-2-ylamino)butoxy]
phenyl}sulfonyl)amino]pent-4-ynoic acid;

(3S)-5-[3,5-Bis(trifluoromethyl)phenyl]-3-[({3-[4-pyridin-
2-ylamino)butoxy]phenyl}sulfonyl)amino]pent-4-ynoic
acid;

(3S)-5-(3,5-Dichlorophenyl)-3-[({3-[4-(pyridin-2-ylamino)
butoxy]-phenyl}sulfonyl)amino]pent-4-ynoic acid;

(3S)-5-[2-(Aminosulfonyl)phenyl]-3-[({3-[4-(pyridin-2-
ylamino)butoxy]phenyl}sulfonyl)amino]pent-4-ynoic
acid;

1-({3-[4-(Pyridin-2-ylanino)butoxy]phenyl}sulfonyl)
piperidine-3-carboxylic acid;

N-({3-[4-(Pyridin-2-ylamino)butoxy]phenyl}sulfonyl)-L-
aspartic acid;

2,2-Difluoro-3-phenyl-3-[({3-[4-(pyridin-2-ylamino)
butoxy]-phenyl}sulfonyl)amino]propanoic acid;

(S) 3-[(3,5-dichloro-2-hydroxyphenyl)-3-(3-
methoxyphenylsulfonylamino)]propionic acid;

3-Pheny-4-[3-{3-(pyridin-2-yl)amino-1-propyloxy}phenyl]
butanoic acid.

7. A pharmaceutical composition comprising a therapeutically effective amount of a compound according to claim 1 and a pharmaceutically acceptable carrier.

8. A pharmaceutical composition comprising a therapeutically effective amount of a compound according to claim 6 and a pharmaceutically acceptable carrier.

9. A method for treating conditions mediated by the $α_vβ_3$ integrin in a mammal in need of such treatment comprising administering an effective $α_vβ_3$ inhibiting amount of a compound of claim 1.

10. A method for treating conditions mediated by the $α_vβ^3$ integrin in a mammal in need of such treatment comprising administering an effective $α_vβ_3$ inhibiting amount of a compound of claim 6.

11. The method according to claim 9 wherein the condition treated is selected from the group consisting of solid tumor growth, tumor metastasis, angiogenesis, osteoporosis, humoral hypercalcemia of malignancy, smooth muscle cell migration, restenosis, atheroscelorosis, macular degeneration, retinopathy, and arthritis.

12. The method according to claim 10 wherein the condition treated is selected from the group consisting of solid tumor growth, tumor metastasis, angiogenesis, osteoporosis, humoral hypercalcemia of malignancy, smooth muscle cell migration, restenosis, atheroscelorosis, macular degeneration, retinopathy, and arthritis.

13. A method for treating conditions mediated by the $α_vβ_5$ integrin in a mammal in need of such treatment comprising administering an effective $α_vβ_5$ inhibiting amount of a compound of claim 1.

14. A method for treating conditions mediated by the $α_vβ_5$ integrin in a mammal in need of such treatment comprising administering an effective $α_vβ_5$ inhibiting amount of a compound of claim 6.

15. The method according to claim 13 wherein the condition treated is selected from the group consisting of solid tumor growth, tumor metastasis, angiogenesis, osteoporosis, humoral hypercalcemia of malignancy, smooth muscle cell migration, restenosis, atheroscelorosis, macular degeneration, retinopathy, and arthritis.

16. The method according to claim 14 wherein the condition treated is selected from the group consisting of solid tumor growth, tumor metastasis, angiogenesis, osteoporosis, humoral hypercalcemia of malignancy, smooth muscle cell migration, restenosis, atheroscelorosis, macular degeneration, retinopathy, and arthritis.

* * * * *